US009556137B2

(12) United States Patent
Masuno et al.

(10) Patent No.: US 9,556,137 B2
(45) Date of Patent: Jan. 31, 2017

(54) METHODS FOR PREPARING ALKYLFURANS

(71) Applicants: MICROMIDAS, INC., West Sacramento, CA (US); THE REGENTS OF THE UNIVERSITY OF CALIFORNIA, Oakland, CA (US)

(72) Inventors: Makoto N. Masuno, Elk Grove, CA (US); Saikat Dutta, Dist. East Midnapur (IN); Mark Mascal, Sacramento, CA (US)

(73) Assignees: Micromidas, inc., West Sacramento, CA (US); The Regents Of The University of California, Oakland, CA (US)

( * ) Notice: Subject to any disclaimer, the term of this patent is extended or adjusted under 35 U.S.C. 154(b) by 0 days.

(21) Appl. No.: 14/852,134

(22) Filed: Sep. 11, 2015

(65) Prior Publication Data

US 2015/0376153 A1     Dec. 31, 2015

Related U.S. Application Data

(63) Continuation of application No. PCT/US2014/024981, filed on Mar. 12, 2014.
(60) Provisional application No. 61/792,021, filed on Mar. 15, 2013.

(51) Int. Cl.
*C07D 307/36* (2006.01)
*C07D 307/52* (2006.01)

(52) U.S. Cl.
CPC ........... *C07D 307/36* (2013.01); *C07D 307/52* (2013.01); *Y02P 20/582* (2015.11)

(58) Field of Classification Search
CPC ..... C07D 307/36; C07D 307/52; Y02P 20/582
See application file for complete search history.

(56) References Cited

U.S. PATENT DOCUMENTS

| | | | |
|---|---|---|---|
| 2,098,592 | A | 11/1937 | Perkins et al. |
| 2,175,585 | A | 10/1939 | Adkins et al. |
| 2,470,070 | A | 5/1949 | Heilbron et al. |
| 6,103,920 | A | 8/2000 | Johnson et al. |
| 6,410,768 | B1 | 6/2002 | Llatas et al. |
| 8,314,267 | B2 | 11/2012 | Brandvold |
| 2004/0087434 | A1 | 5/2004 | Llatas et al. |
| 2010/0145087 | A1 | 6/2010 | Mikhailine et al. |
| 2011/0263880 | A1 | 10/2011 | Rauchfuss et al. |

FOREIGN PATENT DOCUMENTS

| | | |
|---|---|---|
| CN | 1257468 A | 6/2000 |
| GB | 903615 A | 8/1962 |
| WO | 94/18188 A1 | 8/1994 |
| WO | 98/42643 A1 | 10/1998 |
| WO | 2012/064898 A1 | 5/2012 |

OTHER PUBLICATIONS

Malkov, A.V.,"Asymmetric Reduction of Imines with Trichlorosilane, Catalyzed by Sigamide, an Amino Acid-Derived Formamide: Scope and Limitations." The Journal of organic chemistry 74.16 (2009): 5839-5849.*
Braude et al., "Hydrogen Transfer. Part VIII. Metal-Catalysed Transfer-Hydrogenation of Miscellaneous Acceptors", J. Chem. Soc., 1954, pp. 3595-3598.
Burnette et al., "Production of 2-Methylfuran by Vapor-Phase Hydrogenation of Furfural", Ind. Eng. Chem., vol. 40, No. 3, Mar. 1948, pp. 502-505.
Chidambaram et al., "A Two-Step Approach for the Catalytic Conversion of Glucose to 2,5-Dimethylfuran in Ionic Liquids", Green Chemistry, vol. 12, 2010, pp. 1253-1262.
De et al., "One-Pot Conversions of Lignocellulosic and Algal Biomass into Liquid Fuels", ChemSusChem, vol. 5, 2012, pp. 1826-1833.
Drisko et al., "The Reaction of Certain Substituted Furfurals with Aniline and Aniline Hydrochloride", J. Am. Chem. Soc., vol. 74, No. 10, May 20, 1952, pp. 2626-2628.
Dutta et al., "Novel Pathways to 2,5-Dimethylfuran via Biomass-Derived 5-(Chloromethyl)Furfural", ChemSusChem, vol. 7, 2014, pp. 3028-3030.
Hamada et al., "Novel Synthetic Route to 2,5-Disubstituted Furan Derivatives through Surface Active Agent-Catalyzed Dehydration of D-(-)-Fructose", J. Oleo Sci., vol. 50, No. 6, 2001, pp. 533-536.
Hansen et al., "One-Pot Reduction of 5-Hydroxymethylfurfural via Hydrogen Transfer from Supercritical Methanol", Green Chemistry, vol. 14, No. 9, 2012, pp. 2457-2461.
Hu et al., "Chemoselective Hydrogenation of Biomass-Derived 5-Hydroxymethylfurfural into the Liquid Biofuel 2,5-Dimethylfuran", Ind. Eng. Chem. Res., vol. 53, 2014, pp. 9969-9978.
International Preliminary Report on Patentability received for PCT Patent Application No. PCT/US2014/024981, mailed on Sep. 24, 2015, 7 pages.
International Search Report and Written Opinion received for PCT Patent Application No. PCT/US2014/024981, mailed on Jul. 8, 2014, 9 pages.
Iriye et al., "The Formation of Alkylfurans from (E)-4-Hydroxy-2-Alkenals and (E)-4-Oxo-2-Alkenols, and a Synthesis of Rosefuran", Agricultural and Biological Chemistry, vol. 54, No. 7, Jan. 1, 1990, pp. 1841-1843.
Jae et al., "Production of Dimethylfuran from Hydroxymethylfurfural through Catalytic Transfer Hydrogenation with Ruthenium Supported on Carbon", ChemSusChem, vol. 6, 2013, pp. 1158-1162.

(Continued)

*Primary Examiner* — Samantha Shterengarts
*Assistant Examiner* — Matt Mauro
(74) *Attorney, Agent, or Firm* — Morrison & Foerster LLP

(57) ABSTRACT

Provided herein are methods for preparing alkylfurans, such as 2,5-dialkylfurans and 2-alkylfurans. Furfural or 5-alkylfurfural can be reacted with aniline or diaminobenzene, or derivatives thereof, to form the corresponding imine, which can be reduced to form alkylfurans and to regenerate the aniline or diaminobenzene, or derivatives thereof. The alkylfuran may be, for example, 2,5-dimethylfuran or 2-methylfuran.

22 Claims, 5 Drawing Sheets

(56) References Cited

OTHER PUBLICATIONS

Kabalka et al., "Alkylation of Aldehyde (Arenesulfonyl)Hydrazones with Trialkylboranes", The Journal of Organic Chemistry, vol. 62, No. 11, May 30, 1997, pp. 3688-3695.
Klepo et al., "Studies in the Furan Series. 22. N-Arylfurfuryl-and N-Aryl-5-Methylfurfurylamines and their N-Allyl Derivatives", J. Chem. Eng. Data, vol. 30, No. 2, 1985, pp. 235-237.
Kong et al., "Switchable Synthesis of 2,5-Dimethylfuran and 2,5-Dihydroxymethyltetrahydrofuran from 5-Hydroxymethylfurfural over Raney Ni Catalyst", RSC Adv., vol. 4, 2014, pp. 60467-60472.
Kumalaputri et al., "Tunable and Selective Conversion of 5-HMF to 2,5-Furandimethanol and 2,5-Dimethylfuran over Copper-Doped Porous Metal Oxides", ChemSusChem, 2014, 11 pages.
Mitra et al., "Pd/C-Catalyzed Reactions of HMF: Decarbonylation, Hydrogenation, and Hydrogenolysis", Green Chemistry, 2014, 14 pages.
Najim et al., "Utilization of m-Phenylenediamine-Furfural Resin for Removal of Cu(II) from Aqueous Solution-A Thermodynamic Study", E-Journal of Chemistry, vol. 7, No. 3, 2010, pp. 757-762.
Nakagawa et al., "Catalytic Reduction of Biomass-Derived Furanic Compounds with Hydrogen", ACS Catal., vol. 3, 2013, pp. 2655-2668.
Nishimura, Shigeo, "Handbook of Heterogeneous Catalytic Hydrogenation for Organic Synthesis", John Wily & Sons Inc., 2001, 747 pages.
Partial European Search Report received for European Patent Application No. 14769546.4, mailed on Jun. 24, 2016, 6 pages.
Ram et al., "Debenzylation of N-Benzylamino Derivatives by Catalytic Transfer Hydrtyation With Ammonium Formate", Synthetic Communications, vol. 17, No. 4, 1987, pp. 415-418.
Roman-Leshkov et al., "Phase Modifiers Promote Efficient Production of Hydroxymethylfurfural from Fructose", Science, vol. 312, Jun. 30, 2006, pp. 1933-1937.
Román-Leshkov et al., "Production of Dimethylfuran for Liquid Fuels from Biomass-Derived Carbohydrates", Nature, vol. 447, Nature Publishing Group, Jun. 21, 2007, pp. 982-985.
Saha et al., "Zinc-Assisted Hydrodeoxygenation of Biomass-Derived 5-Hydroxymethylfurfural to 2,5-Dimethylfuran", ChemSusChem, vol. 7, 2014, pp. 3095-3101.
Schniepp et al., "The Preparation of Acetopropyl Alcohol and 1,4-Pentanediol from Methylfuran", J. Am. Chem. Soc., vol. 69, Mar. 1947, pp. 672-674.
Schwarz et al., "Methods for Preparation of Catalytic Materials", Chem. Rev., vol. 95, No. 3, 1995, pp. 477-510.
Sharma et al., "Liquid Phase Chemo-Selective Catalytic Hydrogenation of Furfural to Furfuryl Alcohol", Applied Catalysis A: General, vol. 454, 2013, pp. 127-136.
Smith et al., "Heterogeneous Catalysis in Organic Chemistry", Academic Press, 1999, 363 pages.
Thananatthanachon et al., "Efficient Production of the Liquid Fuel 2,5-Dimethylfuran from Fructose using Formic Acid as a Reagent", Angewandte Chemie International Edition, vol. 49, 2010, 31 pages.
Wang et al., "Platinum-Cobalt Bimetallic Nanoparticles in Hollow Carbon Nanospheres for Hydrogenolysis of 5-Hydroxymethylfurfural", Nature Materials, 2014, 19 pages.
Werner, Herz, "Reaction of Furfural Derivatives with Maleic Anhydride", Journal of the American Chemical Society, vol. 67, No. 10, Oct. 1, 1945, pp. 1854-1855.
Zheng et al., "An Environmentally Benign Process for the Efficient Synthesis of Cyclohexanone and 2-Methylfuran", Green Chem., vol. 8, 2006, pp. 107-109.
Zheng et al., "Towards Understanding the Reaction Pathway in Vapour Phase Hydrogenation of Furfural to 2-Methylfuran", Journal of Molecular Catalysis A: Chemical, vol. 246, 2006, pp. 18-23.

\* cited by examiner

METHODS FOR PREPARING ALKYLFURANS

CROSS-REFERENCE TO RELATED APPLICATION

This application is a continuation application of International Application PCT/US2014/024981, with an international filing date of Mar. 12, 2014, which claims priority to and the benefit of U.S. Provisional Patent Application No. 61/792,021, filed Mar. 15, 2013, the disclosures of which are incorporated herein by reference in their entireties.

FIELD

The present disclosure relates generally to methods for preparing substituted furans, and more specifically to methods for preparing alkylfurans such 2,5-dialkylfurans (e.g., 2,5-dimethylfuran) and 2-alkylfurans (e.g., 2-methylfuran).

BACKGROUND

Alkylfurans can be used for commercial production of fuels and other products. For example, 2,5-dimethylfuran can be used as a starting material to produce para-xylene and terephthalic acid, which may be used in the production of polyester. See e.g., U.S. Pat. No. 8,314,267.

Several methods are currently known in the art to produce alkylfurans. For example, 2,5-dimethylfuran can be synthesized by pyrolyzing acetone at a temperature above 700° C. for less than a second, and then cooling the reaction gases in a liquid medium. See U.S. Pat. No. 2,098,592. 2,5-Dimethylfuran can also be synthesized by heating hex-3-en-5-yn-2-ol to 100° C. in the presence of a mercuric catalyst. See U.S. Pat. No. 2,470,070. Additionally, 2,5-dimethylfuran can be synthesized by dehydrating fructose to 5-(hydroxymethyl)furfural, and then converting the 5-(hydroxymethyl) furfural to 2,5-dimethylfuran using a CuRu/C catalyst and hydrogen. See Y. Román-Leshkov, et al., *Nature* 2007, 447, 982-985.

There remains, however, a need for new methods to produce alkylfurans, such as 2,5-dimethylfuran.

BRIEF SUMMARY

The present disclosure addresses this need by providing a method for preparing one or more alkylfurans of formula (I):

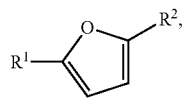
(I)

wherein $R^1$ is H or $C_x$ alkyl, wherein x is an integer equal to or greater than 1; and wherein $R^2$ is $C_y$ alkyl, wherein y is an integer equal to or greater than 1. In certain embodiments, $R^1$ is $C_x$ alkyl.

In some aspects, the method includes reacting an imine of formula (C-1) or (C-2) with a reducing agent in the presence of catalyst to produce an alkylfuran of formula (I). The imine of formula (C-1) or (C-2) is:

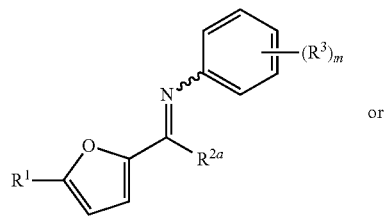
(C-1)

or

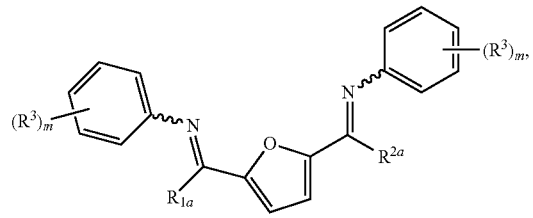
(C-2)

wherein:
$R^1$ (if present) is as defined in formula (I);
$R^{1a}$ (if present) is $C_{x-1}$ alkyl, wherein x is as defined in formula (I), provided that $R^{1a}$ is H when x is 1;
$R^{2a}$ is $C_{y-1}$ alkyl, wherein y is as defined in formula (I), provided that $R^{2a}$ is H when y is 1;
m is 0, 1, 2, 3, 4 or 5; and
each $R^3$ (if present) is independently halo, alkyl, haloalkyl, cycloalkyl, alkoxy, or —C(O)O-alkyl.

In some embodiments, the method further includes reacting a compound of formula (A-1) or (A-2) with an aniline of formula (B) to provide the imine of formula (C-1) or (C-2). The compound of formula (A-1) or (A-2) is:

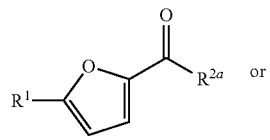
(A-1)

or

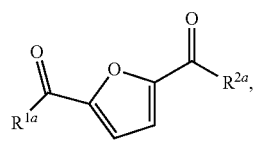
(A-2)

wherein:
$R^1$ is as defined in formula (I);
$R^{1a}$ and $R^{2a}$ (if present) are each as defined in formula (C-1) or (C-2).

The aniline of formula (B) is:

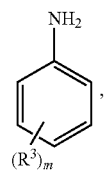
(B)

wherein:
m and $R^3$ are as defined in formula (C-1) or (C-2).

In other aspects, provided is a method for preparing an alkylfuran of formula (I) as described above, wherein the method includes reacting an imine of formula (C-3) with a reducing agent in the presence of catalyst to produce the alkylfuran of formula (I). The imine of formula (C-3) is:

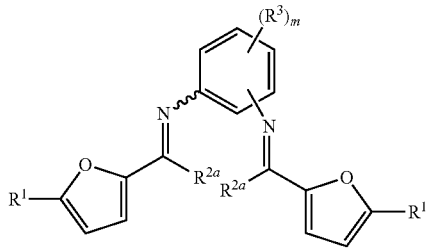
(C-3)

wherein:
$R^1$ is as defined in formula (I);
$R^{2a}$ is H or $C_{y-1}$ alkyl, wherein y is as defined in formula (I), provided that $R^{2a}$ is H when y is 1;
m is 0, 1, 2, 3 or 4; and
each $R^3$ is independently halo, alkyl, haloalkyl, cycloalkyl, alkoxy, or —C(O)O-alkyl.

In some embodiments, the method further includes reacting a compound of formula (A-1) with a diaminobenzene of formula (B-1) to provide the imine of formula (C-3). The compound of formula (A-1) is:

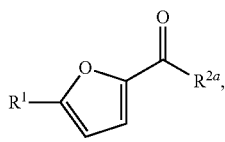
(A-1)

wherein:
$R^1$ is as defined in formula (I);
$R^{1a}$ and $R^{2a}$ are each as defined in formula (C-3).

The diaminobenzene of formula (B-1) is:

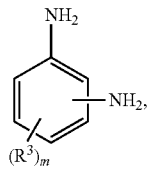
(B-1)

wherein:
m and $R^3$ are as defined in formula (C-3).

In yet other aspects, provided is a method for preparing a mixture of alkylfurans, wherein the mixture comprises an alkylfuran of formula (I') and an alkylfuran of formula (I"), and the method includes reacting an imine of formula (C-4) with a reducing agent in the presence of catalyst to produce the mixture of alkylfurans. The alkylfuran of formula (I') and the alkylfuran of formula (I") are:

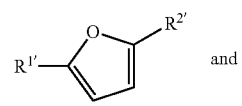
(I')

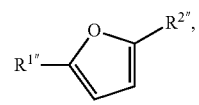
(I"), wherein:
each $R^{1'}$ and $R^{1''}$ is independently H or $C_x$ alkyl, wherein x at each occurrence is independently an integer equal to or greater than 1; and
each $R^{2'}$ and $R^{2''}$ is independently $C_y$ alkyl, wherein y at each occurrence is independently an integer equal to or greater than 1.

The imine of formula (C-4) is:

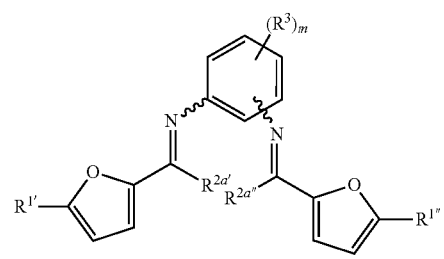
(C-4)

wherein:
$R^{1'}$ is as defined in formula (I');
$R^{2'}$ is as defined in formula (I");
$R^{2a'}$ is H or $C_{y-1}$ alkyl, wherein y is as defined in formula (I'), provided that $R^{2a'}$ is H when y is 1;
$R^{2a''}$ is H or $C_{y-1}$ alkyl, wherein y is as defined in formula (I"), provided that $R^{2a''}$ is H when y is 1;
m is 0, 1, 2, 3 or 4; and
each $R^3$ is independently halo, alkyl, haloalkyl, cycloalkyl, alkoxy, or —C(O)O-alkyl.

In some embodiments, the method further includes reacting a mixture of compounds comprising a compound of formula (A-1') and a compound of formula (A-1") with a diaminobenzene of formula (B-1) to provide the imine of formula (C-4). The compound of formula (A-1') and the compound of formula (A-1") are:

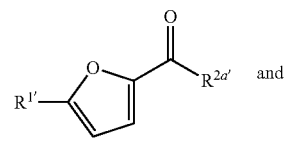
(A-1')

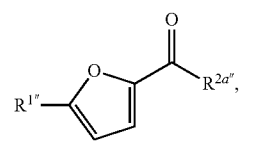
(A-1"), wherein:
$R^{1'}$ and $R^{2a'}$ are as defined in formula (I'); and
$R^{1''}$ and $R^{2a''}$ are as defined in formula (I").

Provided is also a method for preparing 2,5-dimethylfuran, by reacting an unsubstituted or substituted ((5-methylfuran-2-yl)methylene)aniline with a reducing agent in the presence of catalyst to produce 2,5-dimethylfuran.

Provided is also a method for preparing 2,5-dimethylfuran, by reacting an unsubstituted or substituted bis((5-methylfuran-2-yl)methylene)benzene-1,4-diamine with a reducing agent in the presence of catalyst to produce 2,5-dimethylfuran.

Provided is a composition that includes: an imine of formula (C-1) or (C-2) as described herein; a reducing agent; and catalyst. In some aspects, provided is a composition that includes: an unsubstituted or substituted ((5-methylfuran-2-yl)methylene)aniline or an unsubstituted or substituted bis ((5-methylfuran-2-yl)methylene)benzene-1,4-diamine; a reducing agent; and catalyst. Provided is also a composition that includes: a compound of formula (A-1) or (A-2); and an aniline of formula (B).

Provided is a composition that includes: an imine of formula (C-3) as described herein; a reducing agent; and catalyst. In some aspects, provided is a composition that includes: an unsubstituted or substituted bis((5-methylfuran-2-yl)methylene)benzenediamine; a reducing agent; and catalyst. Provided is also a composition comprising: a compound of formula (A-1) or (A-2); and a diaminobenzene of formula (B-1).

Provided is a composition that includes: an imine of formula (C-4) as described herein; a reducing agent; and catalyst. Provided is also a composition comprising: a compound of formula (A-1') and a compound of formula (A-1"); and a diaminobenzene of formula (B-1).

DESCRIPTION OF THE FIGURES

The present application can be understood by reference to the following description taken in conjunction with the accompanying figures.

DETAILED DESCRIPTION

Figure 1:
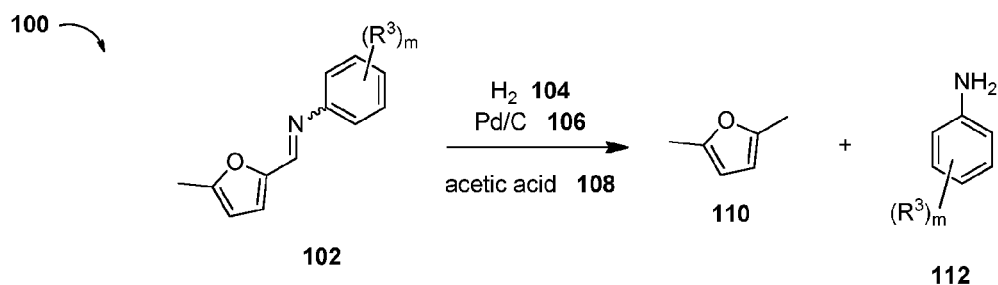
FIG. 1 depicts an exemplary reaction scheme to produce 2,5-dimethylfuran from optionally substituted ((5-methylfuran-2-yl)methylene)aniline.

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —OCH$_3$ is attached through the oxygen atom.

"Alkyl" refers to an unbranched or branched saturated hydrocarbon chain. In some embodiments, alkyl as used herein, such as in compounds of formula (I), (I'), (I"), (A-1), (A-1'), (A-1"), (A-2), (B), (B-1), (C-1), (C-2), (C-3), (C-4), (D-1), (D-2), (D-3), (D-4), (X-1), (X-2), (X-3) or (X-4), has 1 to 10 carbon atoms (i.e., $C_{1-10}$ alkyl), 1 to 10 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), 1 to 2 carbon atoms (i.e., $C_{1-2}$ alkyl), or 1 carbon atom (i.e., $C_1$ alkyl). Examples of alkyl groups include methyl, ethyl, n-propyl, iso-propyl, n-butyl, sec-butyl, ten-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and text-butyl; "propyl" can include n-propyl and iso-propyl.

"Cycloalkyl" refers to a cyclic alkyl group. In some embodiments, cycloalkyl as used herein, such as in compounds of (B), (B-1), (C-1), (C-2), (C-3), (C-4), (D-1), (D-2), (D-3), (D-4), (X-1), (X-2), (X-3) or (X-4), has from 3 to 10 ring carbon atoms (i.e., $C_{3-10}$ cycloalkyl), or 3 to 9 ring carbon atoms (i.e., $C_{3-9}$ cycloalkyl), 3 to 8 ring carbon atoms (i.e., $C_{3-8}$ cycloalkyl), 3 to 7 ring carbon atoms (i.e., $C_{3-7}$ cycloalkyl), 3 to 6 ring carbon atoms (i.e., $C_{3-6}$ cycloalkyl), or 5 ring carbon atoms (i.e., $C_5$ cycloalkyl), or 6 ring carbon atoms (i.e., $C_6$ cycloalkyl). Examples of cycloalkyl groups include cyclopropyl, cyclobutyl, cyclopentyl, and cyclohexyl.

"Alkoxy" refers to the group "—O-alkyl". Examples of alkoxy groups may include methoxy, ethoxy, n-propoxy, iso-propoxy, n-butoxy, tert-butoxy, sec-butoxy, n-pentoxy, n-hexoxy, and 1,2-dimethylbutoxy.

"Halo" may include, for example, fluoro, chloro, bromo, and iodo; and the term "halogen" includes fluorine, chlorine, bromine, and iodine. "Haloalkyl" refers to an unbranched or branched chain alkyl group as defined above, wherein one or more hydrogen atoms are replaced by a halogen. For example, where a residue is substituted with more than one halogen, it may be referred to by using a prefix corresponding to the number of halogen moieties attached. For example, dihaloalkyl or trihaloalkyl refers to alkyl substituted with two ("di") or three ("tri") halo groups, which may be, but are not necessarily, the same halogen; thus, for example, —CHFCl is within the scope of dihaloalkyl. Other examples of a haloalkyl group include difluoromethyl (—CHF$_2$) and trifluoromethyl (—CF$_3$).

Methods of Preparing Alkylfurans by Imine Reduction

Provided herein are methods for preparing alkylfurans by an imine reduction reaction. Alkylfurans may include 2,5-dialkylfurans, 2-alkylfurans, or any combinations thereof.

For example, with reference to FIG. 1, process 100 is an exemplary reaction scheme to prepare 2,5-dimethylfuran 110 from imine 102, an optionally substituted ((5-methylfuran-2-yl)methylene)aniline. With respect to imine 102, m may be 0, 1, 2, 3, 4, or 5, and each $R^3$ (if present) may independently be halo, alkyl, haloalkyl, cycloalkyl, alkoxy, or —C(O)O-alkyl.

Imine 102 can be reacted with hydrogen 104 in the presence of palladium catalyst 106 and solvent 108 to yield 2,5-dimethylfuran 110 and optionally substituted aniline 112. As depicted in the exemplary reaction of FIG. 1, palladium catalyst 106 is palladium on carbon (Pd/C), and solvent 108 is acetic acid. It should be understood, however, in other exemplary embodiments, other catalysts and solvents may be employed, as discussed in further detail below. Additionally, in yet other exemplary embodiments, process 100 may be performed neat, i.e., without solvent 108.

Figure 2:
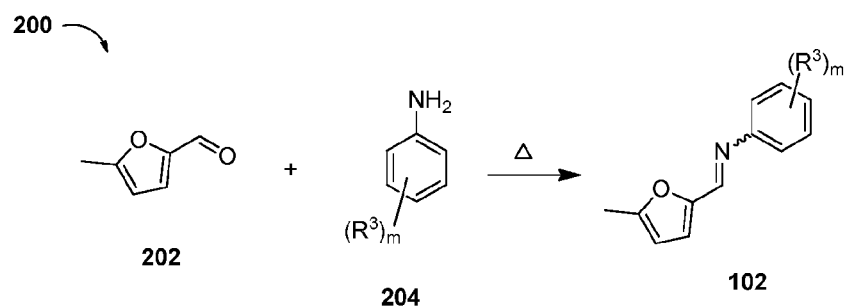
FIG. 2 depicts an exemplary reaction scheme to produce the optionally substituted ((5-methylfuran-2-yl)methylene) aniline from 5-methylfurfural and optionally substituted aniline.

Imine 102 used in the methods described herein may be commercially available. Imine 102 may also be prepared from a furfural compound or a derivative thereof. For example, with reference to FIG. 2, 5-methylfurfural 202 and optionally substituted aniline 204 may be combined at an elevated temperature to yield imine 102 for use as the starting material in process 100 (FIG. 1). It should be understood that aniline 204 used in process 200 (FIG. 2) can be the same compound as aniline 112 produced in process 100 (FIG. 1), as the aniline material can be regenerated from in the imine reduction reaction of process 100 (FIG. 1).

Figure 3:
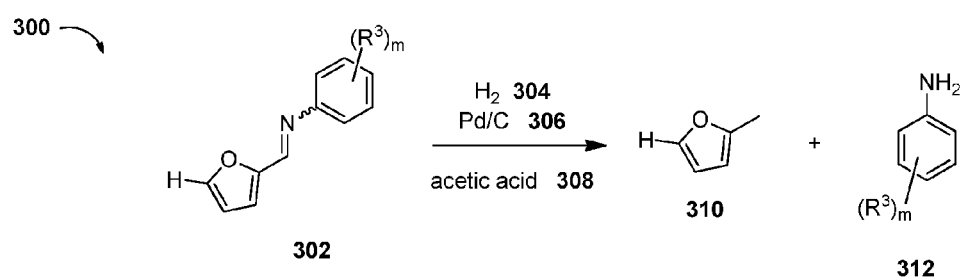
FIG. 3 depicts an exemplary reaction scheme to produce 2-methylfuran from optionally substituted N-(furan-2-ylmethylene)aniline.

In another example, with reference to FIG. 3, process 300 is an exemplary reaction scheme to prepare 2-methylfuran 310 from imine 302, an optionally substituted N-(furan-2-ylmethylene)aniline. With respect to imine 302, m may be 0, 1, 2, 3, 4, or 5, and each $R^3$ (if present) may independently be halo, alkyl, haloalkyl, cycloalkyl, alkoxy, or —C(O)O-alkyl.

Imine 302 can be reacted with hydrogen 304 in the presence of palladium catalyst 306 and solvent 308 to yield 2-methylfuran 310 and optionally substituted aniline 312. As depicted in the exemplary reaction of FIG. 3, palladium catalyst 306 is palladium on carbon (Pd/C), and solvent 308 is acetic acid. It should be understood, however, in other exemplary embodiments, other catalysts and solvents may be employed, as discussed in further detail below. Additionally, in yet other exemplary embodiments, process 300 may be performed neat, i.e., without solvent 308.

Figure 4:
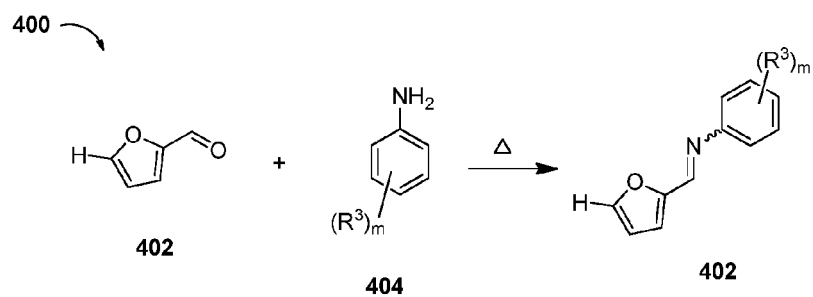
FIG. 4 depicts an exemplary reaction scheme to produce the optionally substituted N-(furan-2-ylmethylene)aniline from furfural and optionally substituted aniline.

Imine 302 used in the methods described herein may be commercially available. Imine 302 may also be prepared from a furfural compound or a derivative thereof. For example, with reference to FIG. 4, furfural 402 and optionally substituted aniline 404 may be combined at an elevated temperature to yield imine 302 for use as the starting material in process 300 (FIG. 3). It should be understood that aniline 404 used in process 400 (FIG. 4) can be the same compound as aniline 312 produced in process 300 (FIG. 3), as the aniline material can be regenerated from in the imine reduction reaction of process 300 (FIG. 3).

Figure 5:
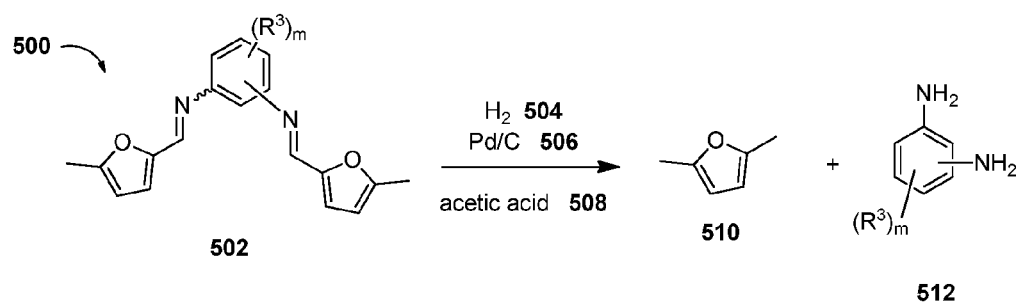
FIG. 5 depicts an exemplary reaction scheme to produce 2,5-dimethylfuran from optionally substituted bis((5-methylfuran-2-yl)methylene)benzenediamine.

In yet another example, with reference to FIG. 5, process 500 is an exemplary reaction scheme to prepare 2,5-dimethylfuran 510 from imine 502, an optionally substituted bis((5-methylfuran-2-yl)methylene)benzenediamine. With respect to imine 502, m may be 0, 1, 2, 3, or 4, and each $R^3$ (if present) may independently be halo, alkyl, haloalkyl, cycloalkyl, alkoxy, or —C(O)O-alkyl.

Imine 502 can be reacted with hydrogen 504 in the presence of palladium catalyst 506 and solvent 508 to yield 2,5-dimethylfuran 510 and optionally substituted diaminobenzene 512. As depicted in the exemplary reaction of FIG. 5, palladium catalyst 506 is palladium on carbon (Pd/C), and solvent 508 is acetic acid. It should be understood, however, in other exemplary embodiments, other catalysts and solvents may be employed, as discussed in further detail below. Additionally, in yet other exemplary embodiments, process 500 may be performed neat, i.e., without solvent 508.

Figure 6A:
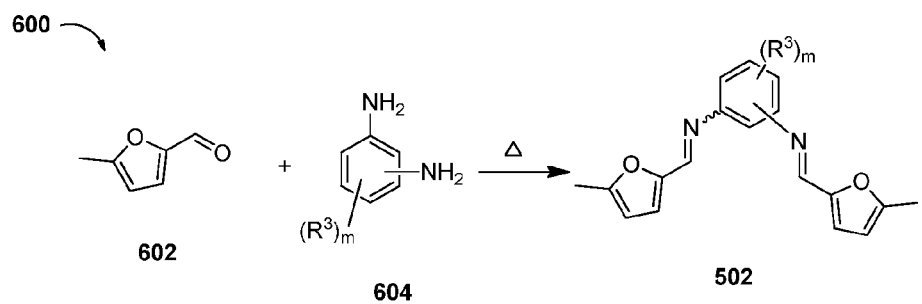
FIG. 6A depicts an exemplary reaction scheme to produce the optionally substituted bis((5-methylfuran-2-yl)methylene)benzenediamine from 5-methylfurfural and optionally substituted diaminobenzene.

Imine 502 used in the methods described herein may be commercially available. Imine 502 may also be prepared from a furfural compound or a derivative thereof. For example, with reference to FIG. 6A, 5-methylfurfural 602 and optionally substituted diaminobenzene 604 may be combined at an elevated temperature to yield imine 502 for use as the starting material in process 500 (FIG. 5). It should be understood that diaminobenzene 604 used in process 600 (FIG. 6A) can be the same compound as diaminobenzene 512 produced in process 500 (FIG. 5), as the aniline material can be regenerated from in the imine reduction reaction of process 500 (FIG. 5).

Figure 6B:
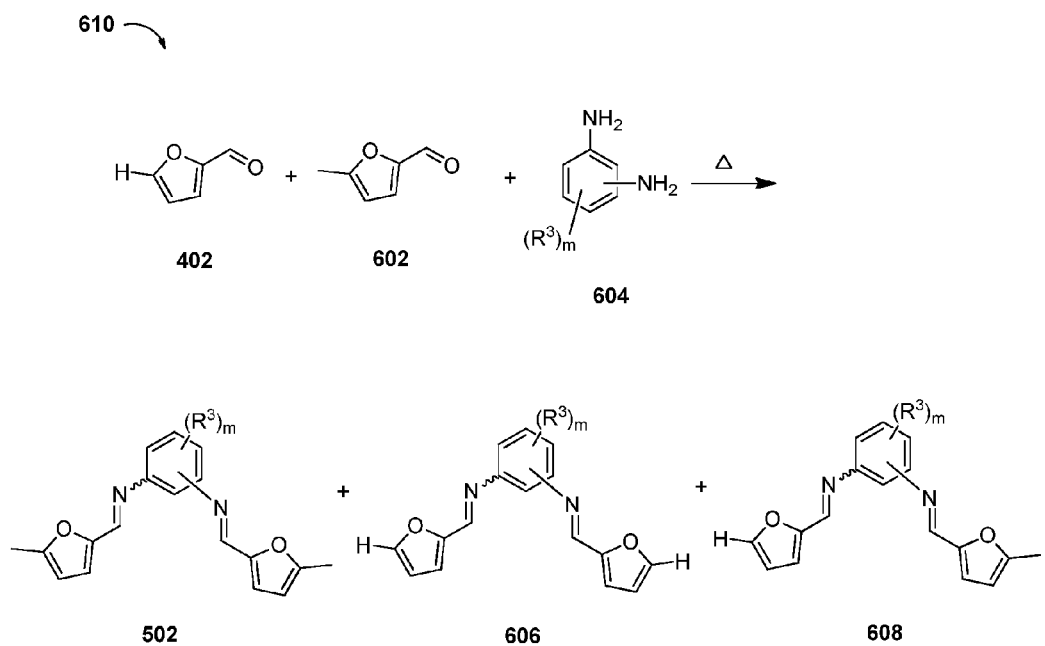
FIG. 6B depicts an exemplary reaction scheme to produce a mixture of imines from 5-methylfurfural and furfural and optionally substituted diaminobenzene.

In one variation, a mixture of imines may be prepared from a mixture of a furfural compound and derivatives thereof. For example, with reference to FIG. 6B, furfural 402, 5-methylfurfural 602 and optionally substituted diaminobenzene 604 may be combined at an elevated temperature to yield imines 502, 606 and 608. It should be understood that imine 608 may be reacted with hydrogen in the presence of palladium catalyst and solvent to yield a mixture of 2,5-dimethylfuran and 2-methylfuran.

Figure 7:
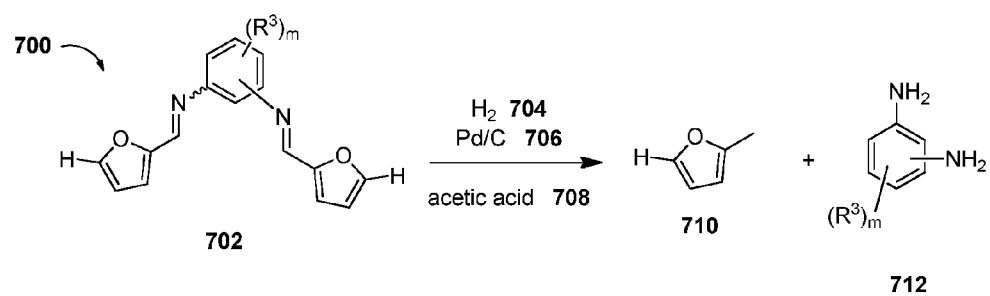
FIG. 7 depicts an exemplary reaction scheme to produce 2-methylfuran from optionally substituted bis(furan-2-ylmethylene)benzene-1,2-diamine.

In yet another example, with reference to FIG. 7, process 700 is an exemplary reaction scheme to prepare 2-methylfuran 710 from imine 702, an optionally substituted bis(furan-2-ylmethylene)benzene-1,2-diamine. With respect to imine 702, m may be 0, 1, 2, 3, or 4, and each $R^3$ (if present) may independently be halo, alkyl, haloalkyl, cycloalkyl, alkoxy, or —C(O)O-alkyl.

Imine 702 can be reacted with hydrogen 704 in the presence of palladium catalyst 706 and solvent 708 to yield 2-methylfuran 710 and optionally substituted diaminobenzene 712. As depicted in the exemplary reaction of FIG. 7, palladium catalyst 706 is palladium on carbon (Pd/C), and solvent 708 is acetic acid. It should be understood, however, in other exemplary embodiments, other catalysts and solvents may be employed, as discussed in further detail below. Additionally, in yet other exemplary embodiments, process 700 may be performed neat, i.e., without solvent 708.

Figure 8:
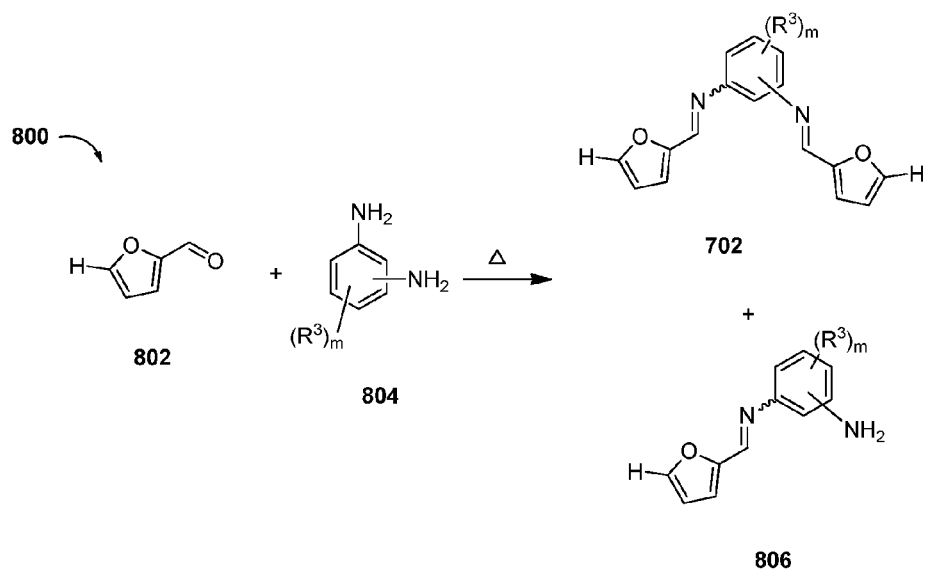
FIG. 8 depicts an exemplary reaction scheme to produce the optionally substituted bis(furan-2-ylmethylene)benzene-1,2-diamine and (furan-2-ylmethylene)benzene-1,2-diamine from furfural and optionally substituted diaminobenzene.

Imine 702 used in the methods described herein may be commercially available. Imine 702 may also be prepared from a furfural compound or a derivative thereof. For example, with reference to FIG. 8, furfural 802 and optionally substituted diaminobenzene 704 may be combined at an elevated temperature to yield imine 702 for use as the starting material in process 700 (FIG. 7). It should be understood that aniline 804 used in process 800 (FIG. 8) can be the same compound as diaminobenzene 712 produced in process 700 (FIG. 7), as the aniline material can be regenerated from in the imine reduction reaction of process 700 (FIG. 7). It should be further understood that, under certain conditions, imine 806 may also be produced, and used to produce 2-methylfuran 710.

Processes 100 and 200 (FIGS. 1 and 2, respectively), or processes 300 and 400 (FIGS. 3 and 4, respectively), or processes 500 and 600 or 610 (FIGS. 5 and 6A or 6B), or process 700 and 800 (FIGS. 7 and 8) may be performed in the same reaction vessel or in different reaction vessels. For example, process 200 may be performed to produce imine 102, which may be used without further isolation and purification in process 100. The hydrogen, the catalyst and, optionally, the solvent may be added to the same reaction vessel containing imine 102 for the imine reduction reaction. In other embodiments, imine 102 may be isolated and, optionally, purified using any suitable methods known in the art before conversion into the alkylfuran. The isolated and optionally purified imine may be returned to the same reaction vessel or a different reaction vessel.

The starting materials, products, and reaction conditions used to prepare the alkylfurans (e.g., 2,5-dialkylfurans and 2-alkylfurans) according to the methods described herein are further described in detail below.

Alkylfurans

The alkylfurans prepared according to the methods described herein have the structure of formula (I):

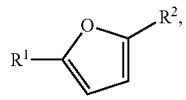
(I)

wherein $R^1$ is H or $C_x$ alkyl, wherein x is an integer equal to or greater than 1; and wherein $R^2$ is $C_y$ alkyl, wherein y is an integer equal to or greater than 1. In some embodiments, $R^1$ is H. In other embodiments, $R^1$ is $C_x$ alkyl. In some embodiments, each $R^1$ and $R^2$ independently has 1 to 10 carbon atoms (i.e., each x and y is independently 1 to 10); 1 to 6 carbon atoms (i.e., each x and y is independently 1 to 6); or 1 to 4 carbon atoms (i.e., each x and y is independently 1 to 4). The methods provided herein may produce one alkylfuran of formula (I) or a mixture of alkylfurans of formula (I).

For example, with reference to process 100 in FIG. 1, or process 500 in FIG. 5, the alkylfuran of formula (I) is 2,5-dimethylfuran:

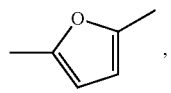

wherein each $R^1$ and $R^2$ is an alkyl having 1 carbon atom (i.e., $R^1$ and $R^2$ are both methyl, in which x is 1 and y is 1).

With reference to process 300 in FIG. 3, or process 700 in FIG. 7, the alkylfuran of formula (I) is 2-methylfuran:

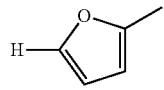

wherein $R^1$ is H and $R^2$ is an alkyl having 1 carbon atom.

It should be understood that $R^1$ and $R^2$ may be the same or different. In some embodiments, as depicted in the exemplary embodiments in FIGS. 1 and 5, $R^1$ and $R^2$ are the same. In another embodiment, $R^1$ and $R^2$ may each have 2 carbon atoms (i.e., $R^1$ and $R^2$ are each ethyl). In other embodiments, $R^1$ and $R^2$ are different. For example, $R^1$ may have 1 carbon atom, and $R^2$ may have 2 carbon atoms (i.e., $R^1$ is methyl, in which x is 1, and $R^2$ is ethyl, in which y is 2). In other embodiments, as depicted in the exemplary embodiments in FIGS. 3 and 7, $R^1$ is H and $R^2$ is methyl.

Imine Compounds

The imine compounds as described in the methods herein are compounds having one or more carbon-nitrogen double bonds. For example, the imine compounds may have one carbon-nitrogen double bond, or two carbon-nitrogen double bonds.

In some embodiments, the imines used in the methods described herein have the structure of formula (C-1):

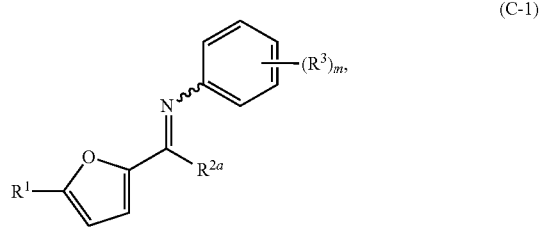
(C-1)

wherein:

$R^1$ is as defined in formula (I);

$R^{2a}$ is $C_{y-1}$ alkyl, wherein y is as defined in formula (I), provided that $R^{2a}$ is H when y is 1;

m is 0, 1, 2, 3, 4 or 5; and each $R^3$ (if present) is independently halo, alkyl, haloalkyl, cycloalkyl, alkoxy, or —C(O)O-alkyl.

For example, with reference to FIG. 1, the imine of formula (C-1) used in process 100 is optionally substituted ((5-methylfuran-2-yl)methylene)aniline, in which $R^1$ is an alkyl having 1 carbon atom (i.e., methyl), and $R^{2a}$ is H. With reference to FIG. 3, the imine of formula (C-1) used in process 300 is optionally substituted N-(furan-2-ylmethylene)aniline, in which $R^1$ is H and $R^{2a}$ is H.

The imine of formula (C-1) may be unsubstituted (i.e., m is 0) or substituted (i.e., m is 1, 2, 3, 4 or 5). It should be understood when more than one $R^3$ group is present on the aniline moiety of the imine compound, each $R^3$ group is denoted as $R^{3a}$, $R^{3b}$, $R^{3c}$, $R^{3d}$, or $R^{3e}$ (if present). It should be understood that the aniline moiety refers to the

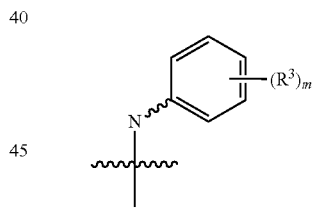

moiety, in which the nitrogen atom is part of the imine bond of the imine compound.

When m is 1, the $R^3$ group may be located on any position of the aniline moiety of the imine of formula (C-1). For example, the $R^3$ group may be located on the aniline moiety as depicted below:

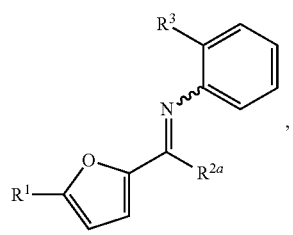

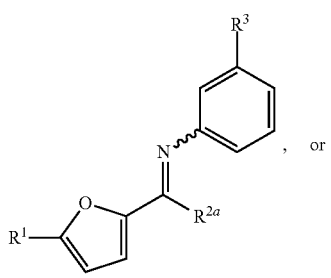

, or

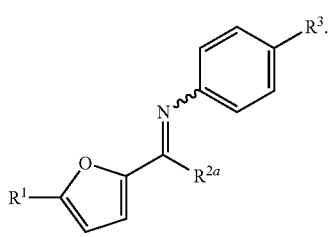

When m is 2, the two R³ (labeled as R³ᵃ and R³ᵇ) groups may be located on any position of the aniline moiety of the imine of formula (C-1). For example, the two R³ groups may be located on the aniline moiety as depicted below:

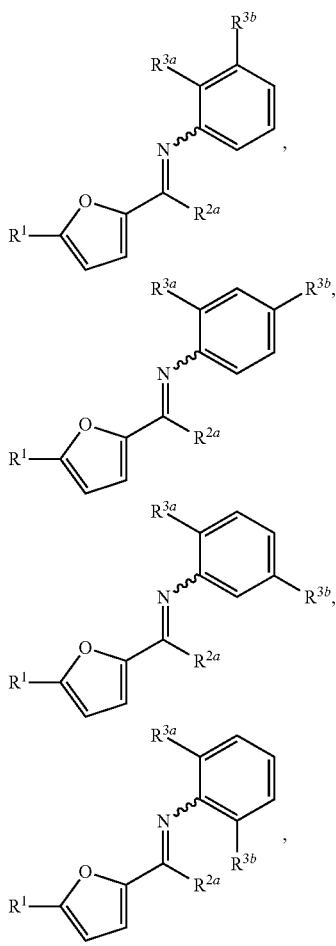

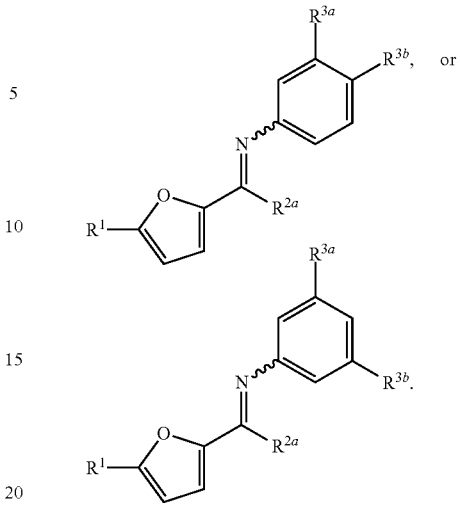

When m is 3, the three R³ groups (labeled as R³ᵃ, R³ᵇ and R³ᶜ) may be located on any position of the aniline moiety of the imine of formula (C-1). For example, the three R³ groups ay be located on the aniline moiety as depicted blow:

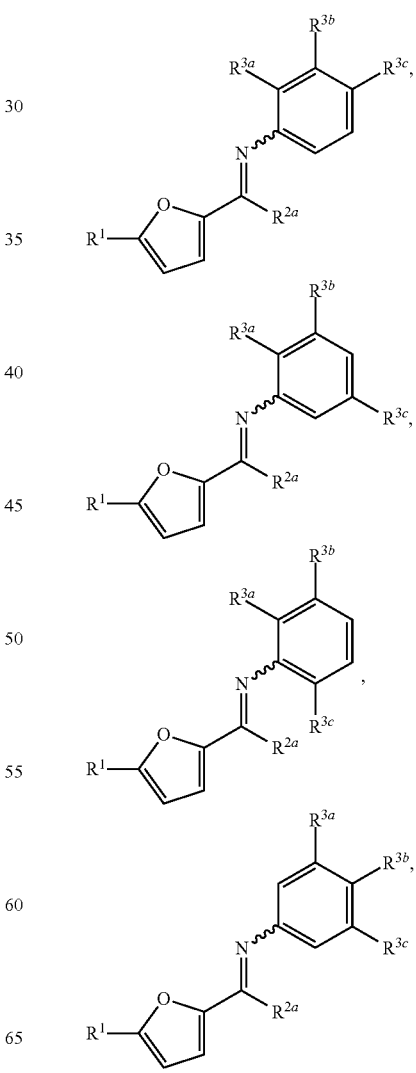

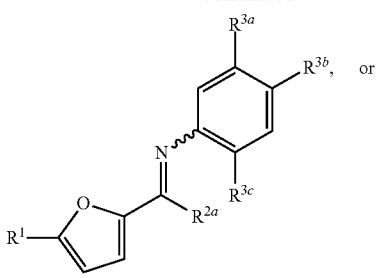

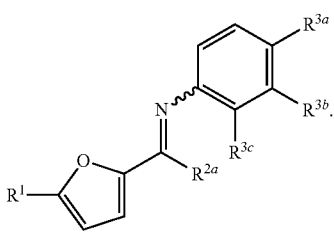

When m is 4, the four $R^3$ groups (labeled as $R^{3a}$, $R^{3b}$, $R^{3c}$ and $R^{3d}$) may be located on any position of the aniline moiety of the imine of formula (C-1). For example, the four $R^3$ groups may be located on the aniline moiety as depicted below:

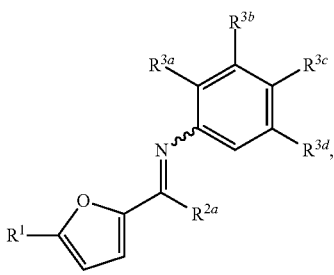

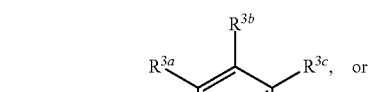

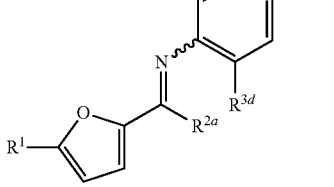

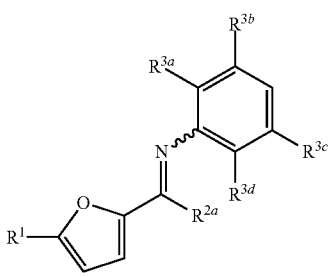

When m is 5, the five $R^3$ groups (labeled as $R^{3a}$, $R^{3b}$, $R^{3c}$, $R^{3d}$ and $R^{3e}$) may be located on any position of the aniline moiety of the imine of formula (C-1) as depicted below:

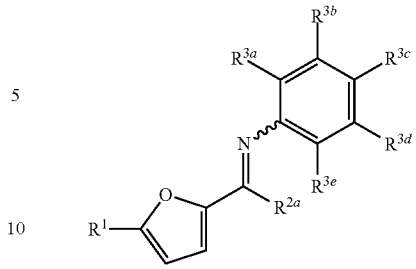

$R^3$ (if present) may be a group that minimizes the reduction of the aromatic ring of the aniline moiety in the imine reduction reaction, thereby allowing for recyclability of the aniline as a reagent. Suitable $R^3$ moieties may include, for example, alkyls (including linear or branched alkyls), haloalkyls, cycloalkyls, halo, esters, and ethers. In some embodiments, each $R^3$ (if present) is independently chloro, fluoro, methyl, ethyl, propyl, butyl (including, for example, t-butyl), —$CF_3$, —$CHF_2$, —$CH_2F$, methoxy, ethoxy, propoxy, butoxy, —$CO_2$-methyl, —$CO_2$-ethyl, —$CO_2$-propyl, or —$CO_2$-butyl. It should be understood that the reduction of the imine compound may be affected by a number of factors, including the choice and number of $R^3$ moieties of the imine compound.

In some embodiments, each $R^3$ of the imine of formula (C-1) (if present) is independently halo. For example, each $R^3$ may be fluoro. In certain embodiments, each $R^3$ of the imine of formula (C-1) (if present) is independently alkyl. In certain embodiments, each $R^3$ is independently a linear alkyl. For example, $R^3$ may be methyl or ethyl. In other embodiments, each $R^3$ of the imine of formula (C-1) (if present) is independently a branched alkyl. For example, each $R^3$ is tert-butyl. In other embodiments, each $R^3$ of the imine of formula (C-1) (if present) is independently haloalkyl. For example, each $R^3$ is independently —$CF_3$, —$CHF_2$, or —$CH_2F$. In yet other embodiments, each $R^3$ of the imine of formula (C-1) (if present) is independently alkoxy. For example, each $R^3$ is independently methoxy, ethoxy, propoxy, or butoxy. In yet other embodiments, each $R^3$ of the imine of formula (C-1) (if present) is independently —C(O)O-alkyl. For example, each $R^3$ is independently —$CO_2$-methyl, —$CO_2$-ethyl, —$CO_2$-propyl, or —$CO_2$-butyl. In yet other embodiments, each $R^3$ of the imine of formula (C-1) (if present) is independently cycloalkyl.

In some embodiments, the imine of formula (C-1) is selected from:

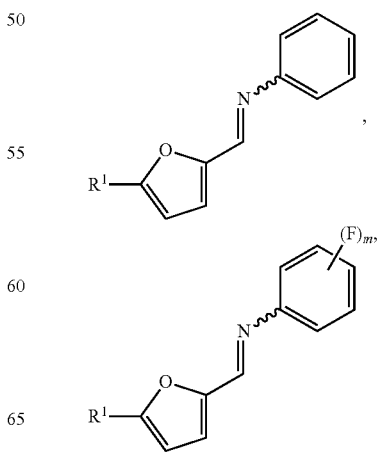

-continued
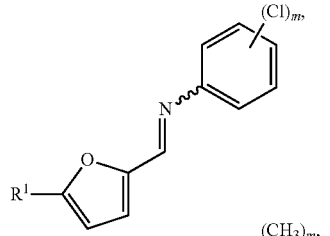
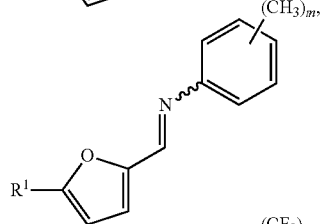
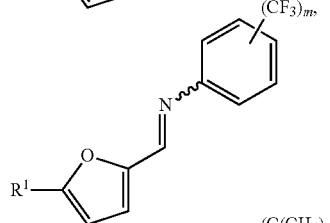
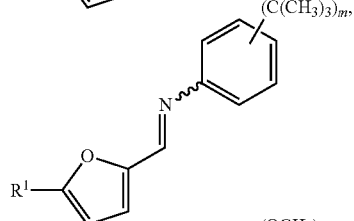
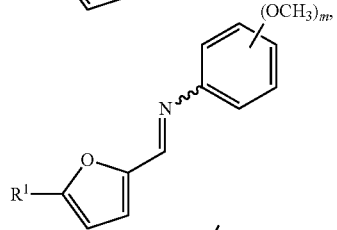
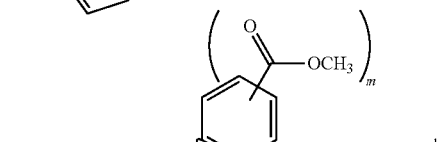
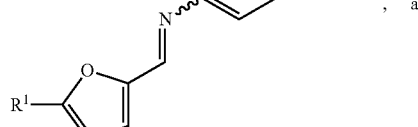
, and
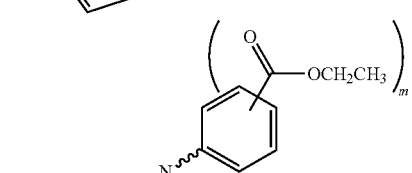
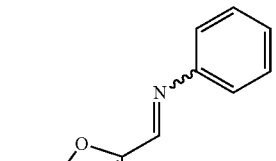
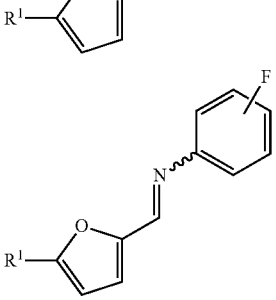
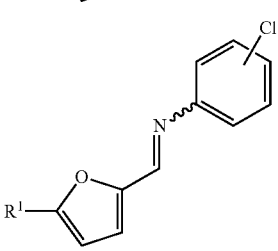
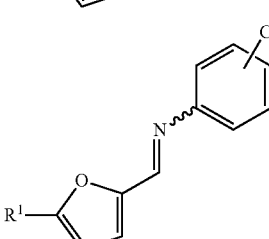
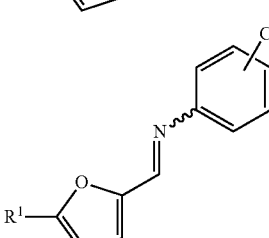
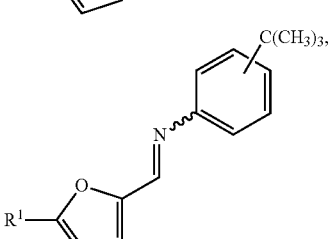
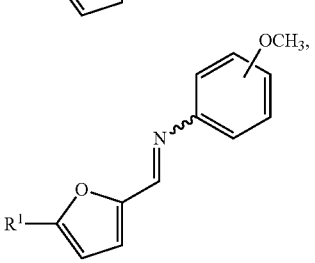
In some embodiments, the imine of formula (C-1) is selected from:

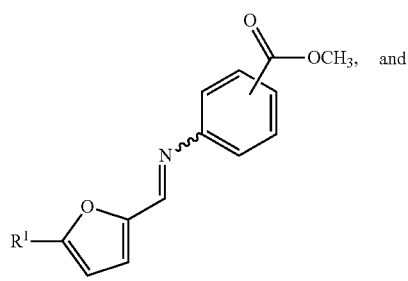
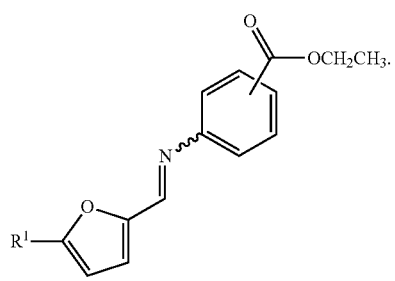
In certain embodiments, the imine of formula (C-1) is selected from:
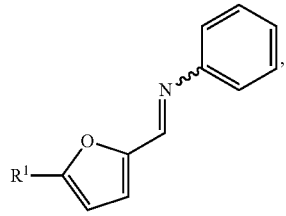
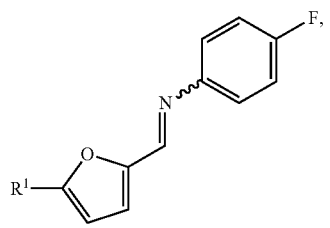
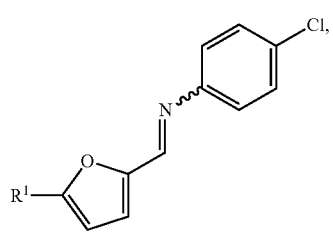
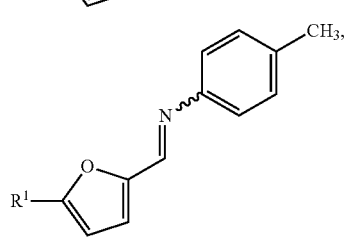
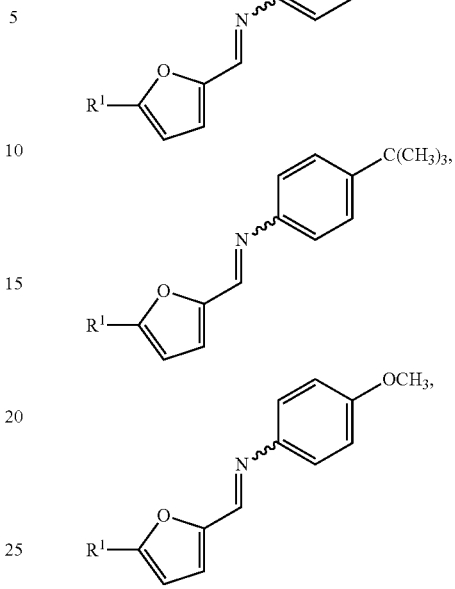
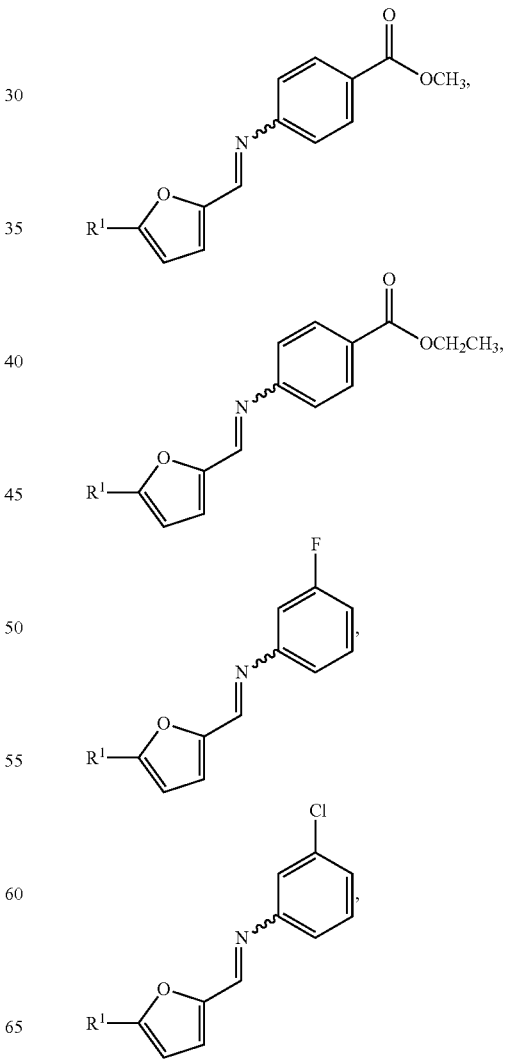

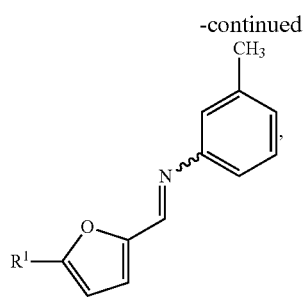
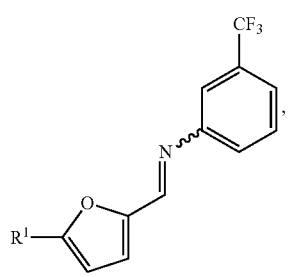
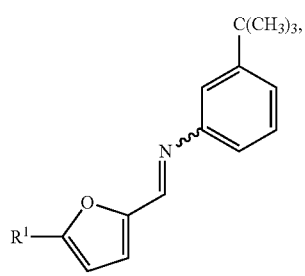
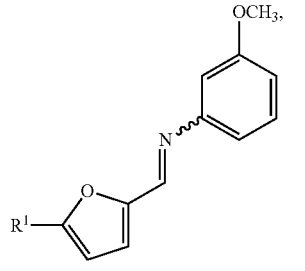
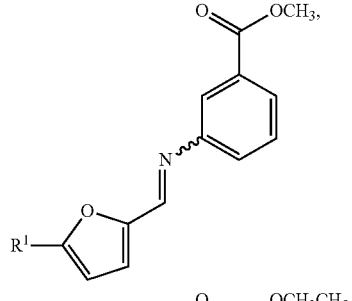
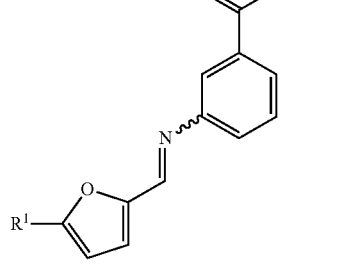
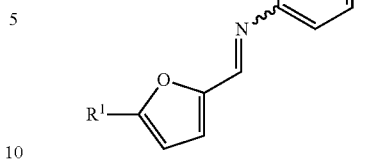
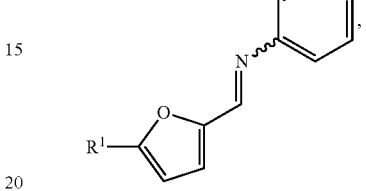
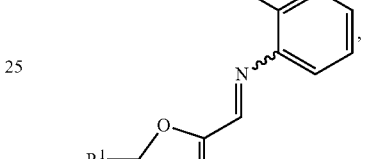
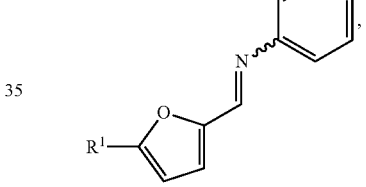
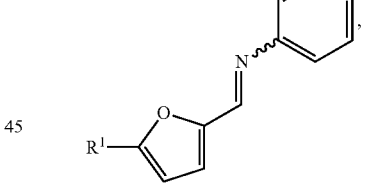
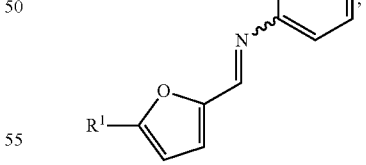
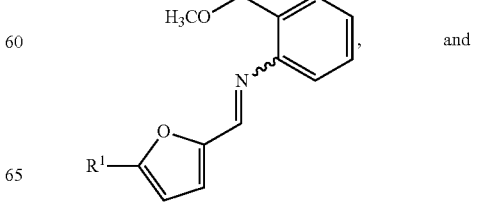
and

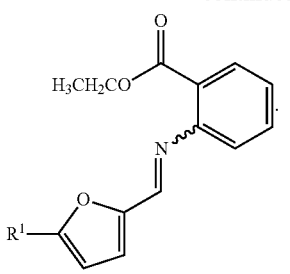

It should be understood that in any of the embodiments descried above for the imine of formula (C-1), $R^1$ may be any of the embodiments described herein for the alkylfuran of formula (I). In some embodiments of the imine of formula (C-1), $R^1$ is H. In other embodiments of the imine of formula (C-1), $R^1$ is $C_x$ alkyl. In certain embodiments of the imine of formula (C-1), $R^1$ is methyl or ethyl.

In one embodiment, the imine of formula (C-1) is selected from:

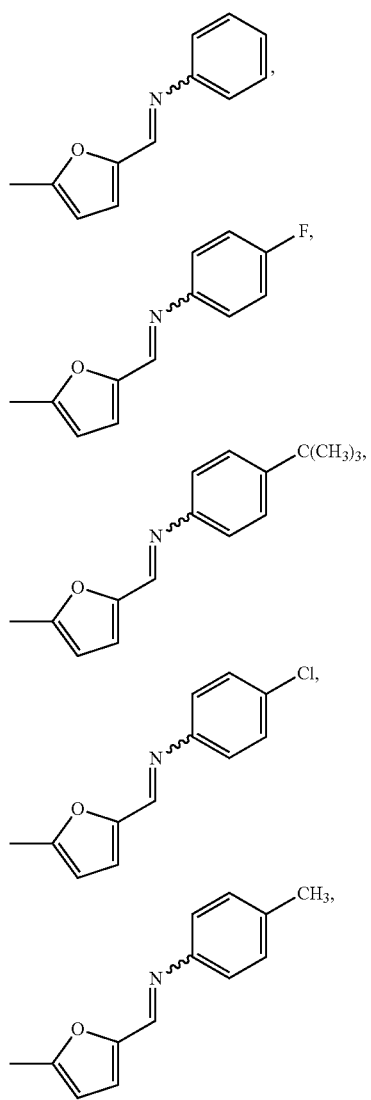

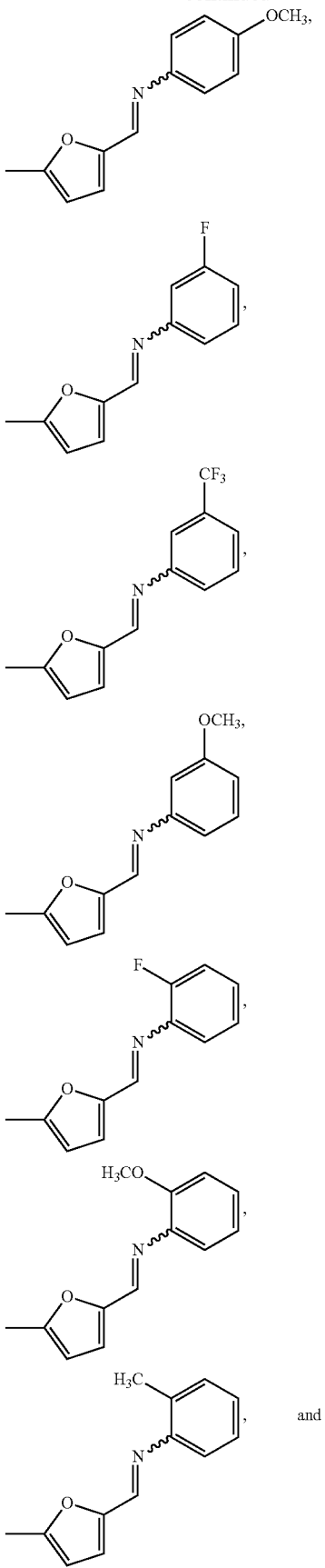

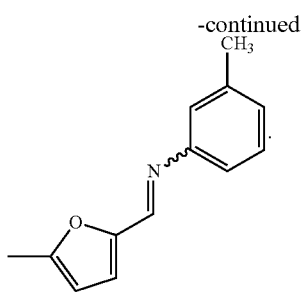

In some embodiments, the imines used in the methods described herein have the structure of formula (C-2):

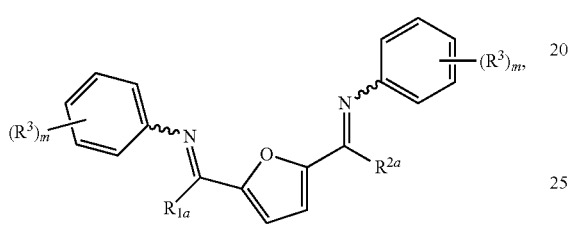

(C-2)

wherein:

$R^{1a}$ is $C_{x-1}$ alkyl, wherein x is as defined in formula (I), provided that $R^{1a}$ is H when x is 1;

$R^{2a}$ is $C_{y-1}$ alkyl, wherein y is as defined in formula (I), provided that $R^{2a}$ is H when y is 1;

each m is independently 0, 1, 2, 3, 4 or 5; and each $R^3$ (if present) is independently halo, alkyl, haloalkyl, cycloalkyl, alkoxy, or —C(O)O-alkyl.

For example, the imine of formula (C-2) used in the methods described herein may be optionally substituted N,N'-(furan-2,5-diylbis(methanylylidene))dianiline, in which $R^{1a}$ and $R^{2a}$ are each H. It should be understood that $R^{1a}$ and $R^{2a}$ may be the same or different, and may vary depending on the alkylfuran of formula (I) to be prepared.

The imine of formula (C-2) may be unsubstituted (i.e., m is 0) or substituted (i.e., at least one m is 1, 2, 3, 4 or 5). When the imine of formula (C-2) is substituted, it should be understood that m on the two aniline moieties in formula (C-2) may be the same or different.

In some embodiments, the imine of formula (C-2) is substituted where m is the same on each aniline moiety. The location of the $R^3$ groups on the two aniline moieties may be the same or different. Examples of an imine of formula (C-2) in which the location of the $R^3$ groups on the two aniline moieties is the same may include:

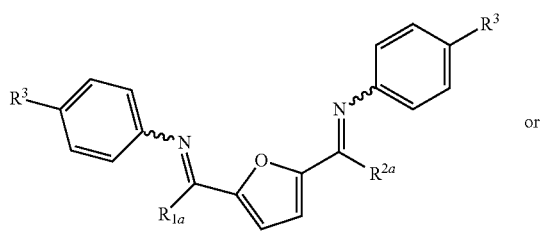

or

Examples of an imine of formula (C-2) in which the location of the $R^3$ groups on the two aniline moieties is different may include:

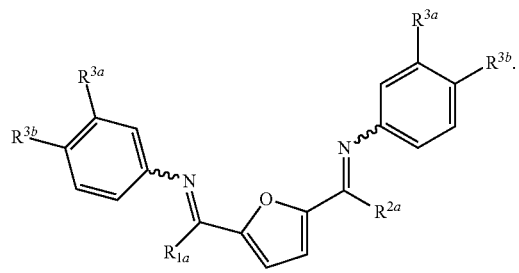

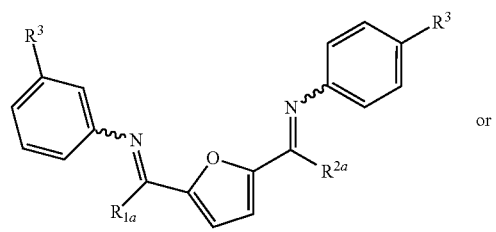

or

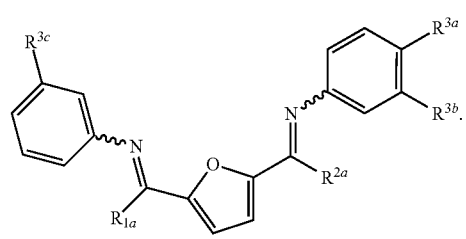

In other embodiments, the imine of formula (C-2) is substituted where m is different on each aniline moiety. An example of such an imine of formula (C-2) may include, for example:

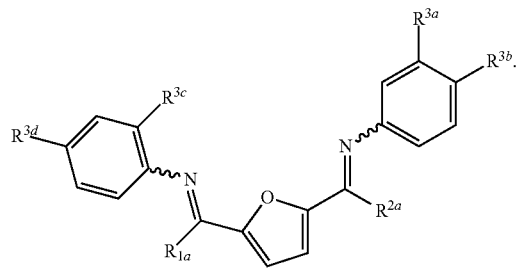

Suitable $R^3$ groups for imines of formula (C-2) may include any of the $R^3$ groups described above for imines of formula (C-1). In some embodiments, the $R^3$ groups (if present) on each aniline moiety of the imines of formula (C-2) may be the same (e.g., $R^3$ on each aniline moiety is fluoro). In other embodiments, the $R^3$ groups on each aniline moiety of the imines of formula (C-2) may be different (e.g., $R^3$ on one aniline moiety is fluoro and $R^3$ on the other aniline moiety is methyl).

In some embodiments, the imine of formula (C-2) is selected from:

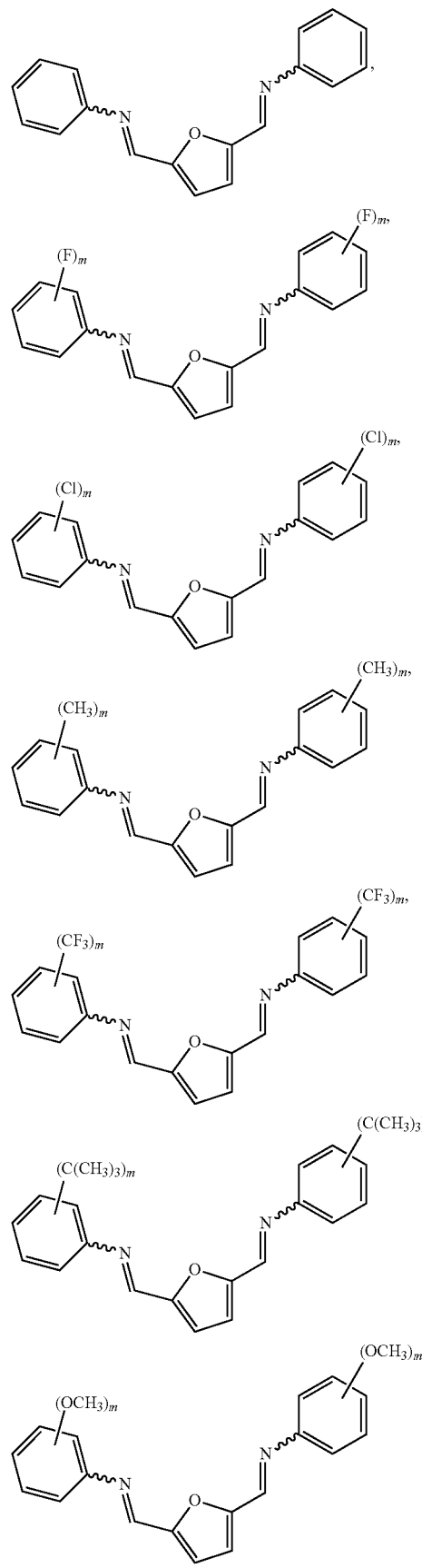
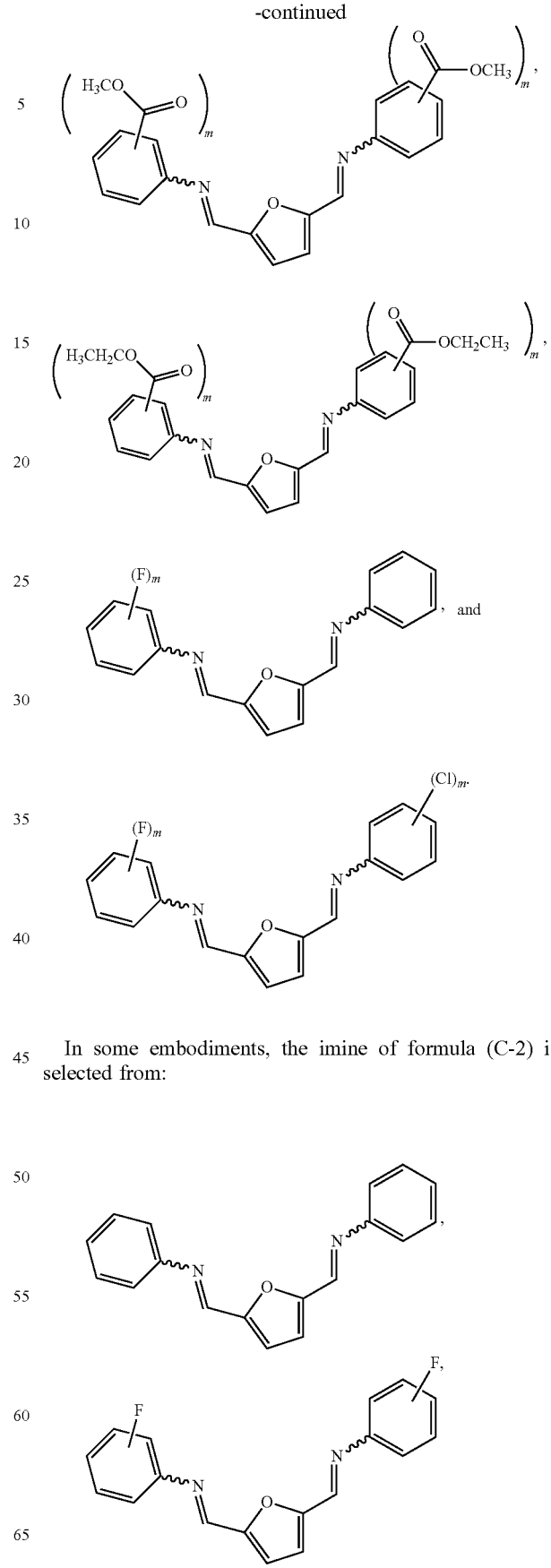
In some embodiments, the imine of formula (C-2) is selected from:

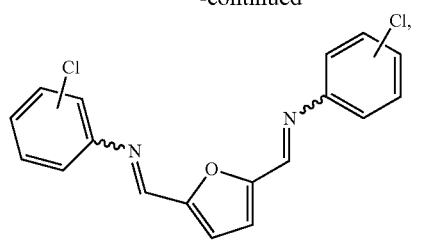
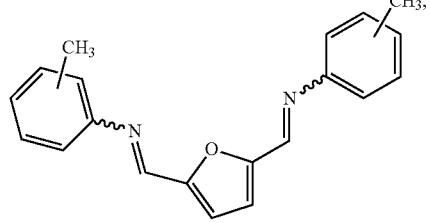
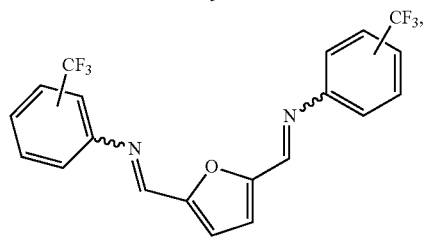
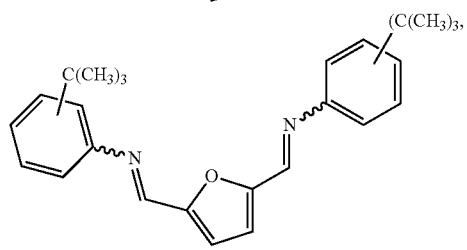
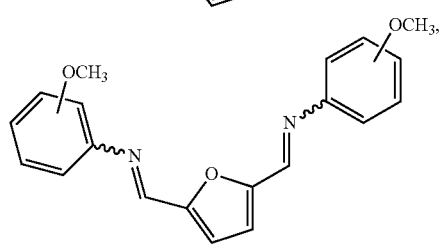
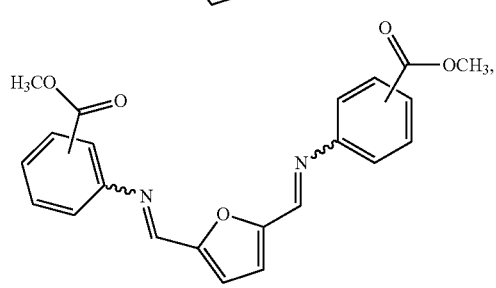
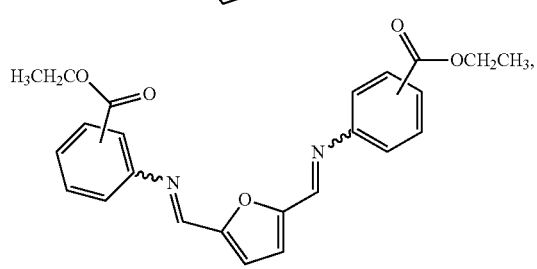
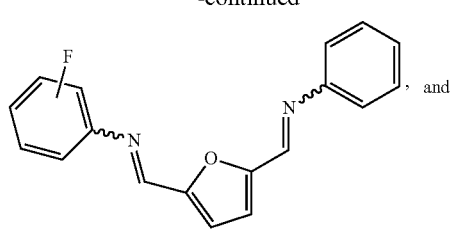
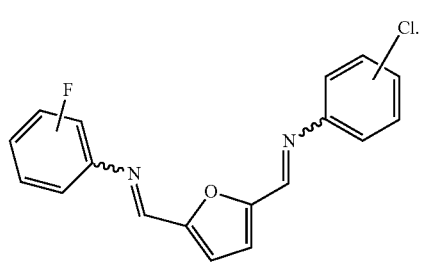
In certain embodiments, the imine of formula (C-2) is selected from:
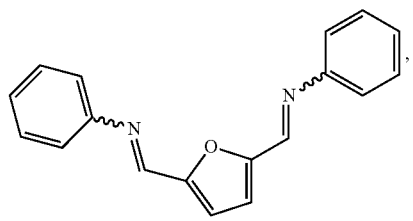
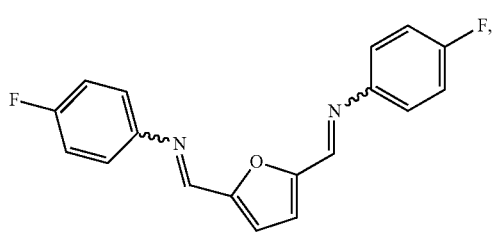
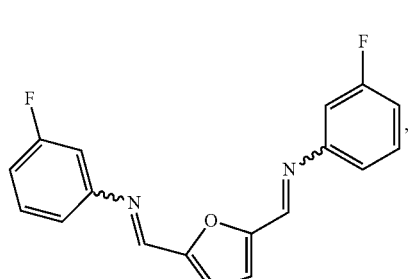
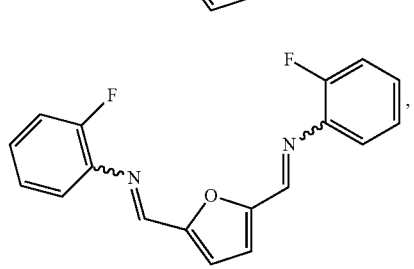

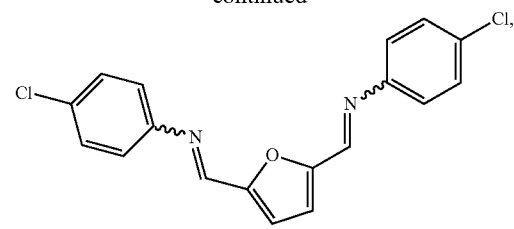
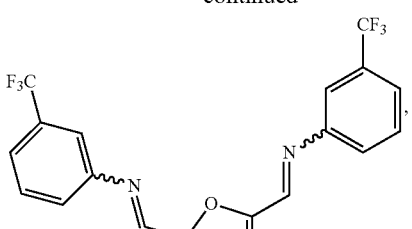
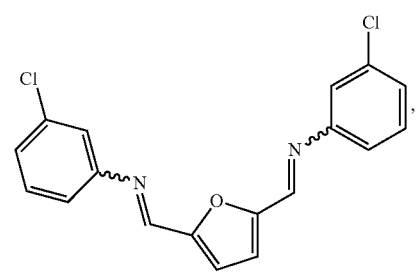
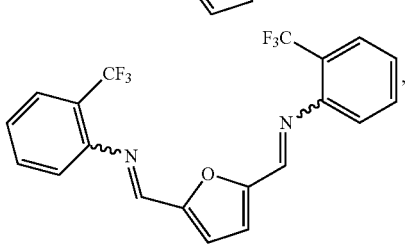
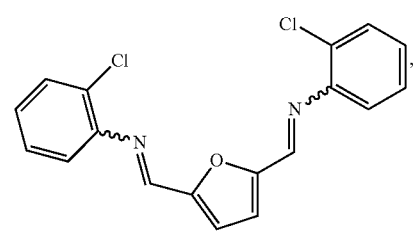
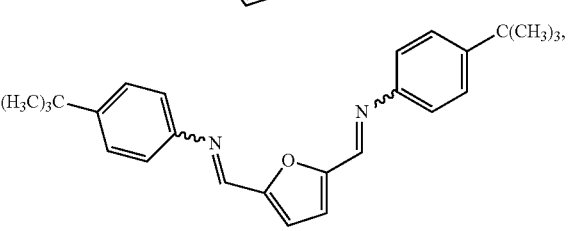
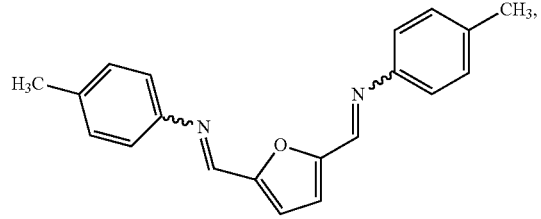
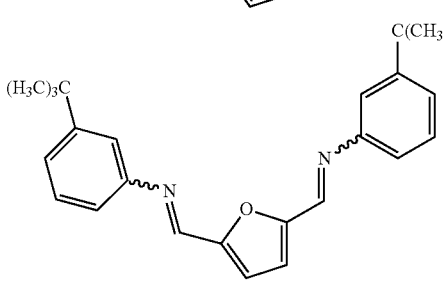
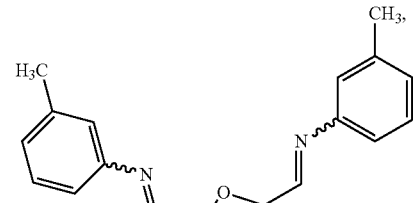
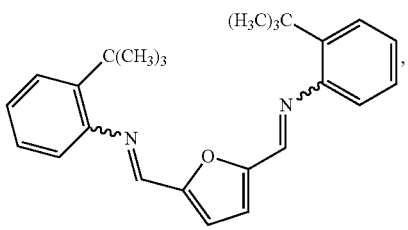
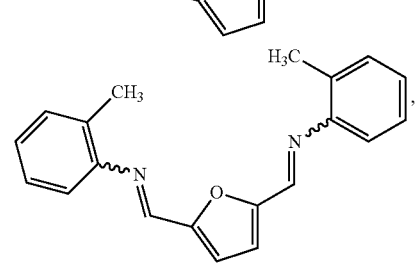
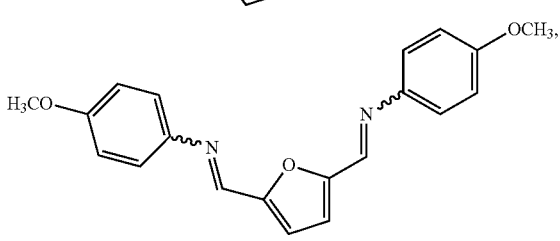
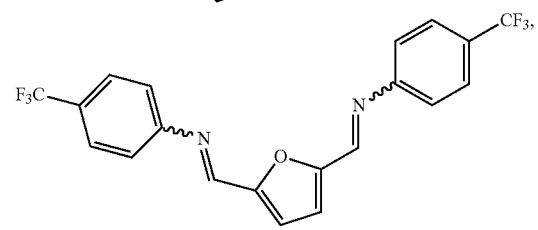

-continued

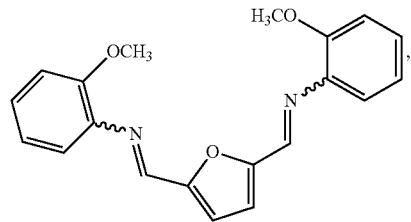

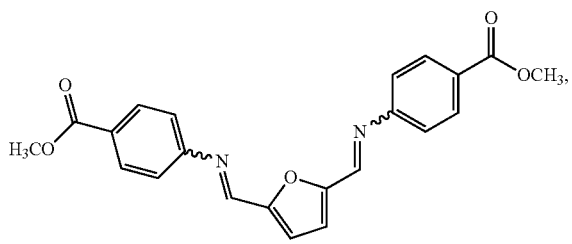

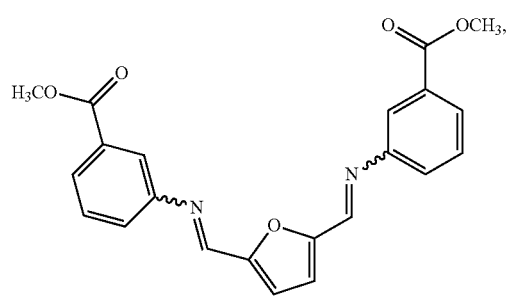

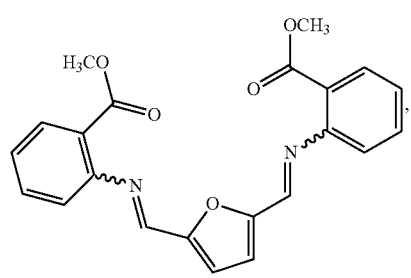

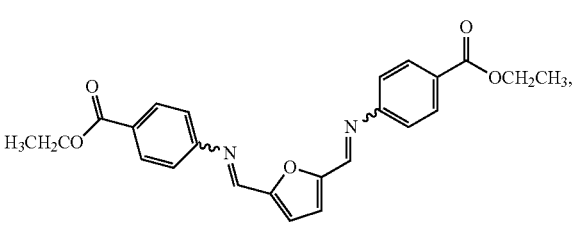

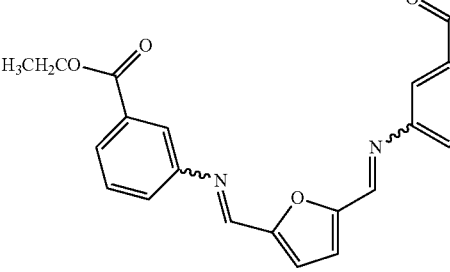

-continued

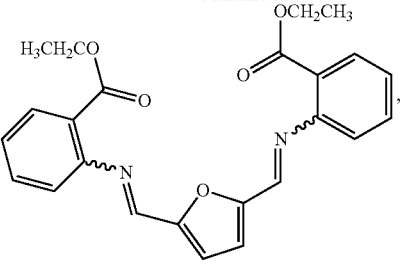

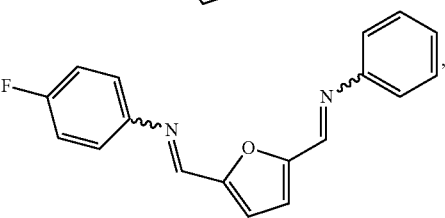

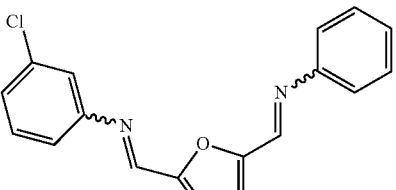

, and

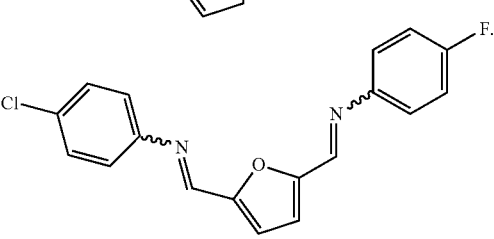

It should be understood that when a diaminobenzyl compound is used, the imine formed may have two moieties having carbon-nitrogen double bonds. Thus, in some embodiments, the imines used in the methods described herein have the structure of formula (C-3):

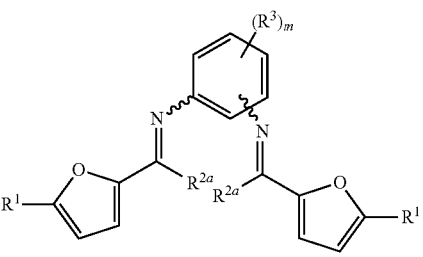

(C-3)

wherein:

$R^1$ is as defined in formula (I);

$R^{2a}$ is H or $C_{y-1}$ alkyl, wherein y is as defined in formula (I), provided that $R^{2a}$ is H when y is 1;

m is 0, 1, 2, 3 or 4; and each $R^3$ is independently halo, alkyl, haloalkyl, cycloalkyl, alkoxy, or —C(O)O-alkyl.

For example, the imine of formula (C-3) used in the methods described herein may be optionally substituted bis((5-methylfuran-2-yl)methylene)benzenediamine, in which $R^{1a}$ and $R^{2a}$ are each H. It should be understood that $R^{1a}$ and $R^{2a}$ may be the same or different, and may vary depending on the alkylfuran of formula (I) to be prepared.

The imine of formula (C-3) may be unsubstituted (i.e., m is 0) or substituted (i.e., at least one m is 1, 2, 3, or 4). When the imine of formula (C-3) is substituted, it should be understood that m on the diaminobenzyl moiety in formula (C-3) may be the same or different. It should be understood that the diaminobenzyl moiety refers to the

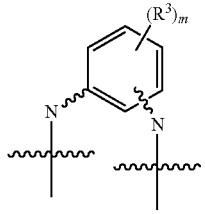

moiety, in which two nitrogen atoms are each part of an imine bond of the imine compound.

The $R^3$ group (if present) may be located on any position of the diaminobenzyl moiety of the imine of formula (C-3). For example, the $R^3$ group may be located on the diaminobenzyl moiety as depicted below:

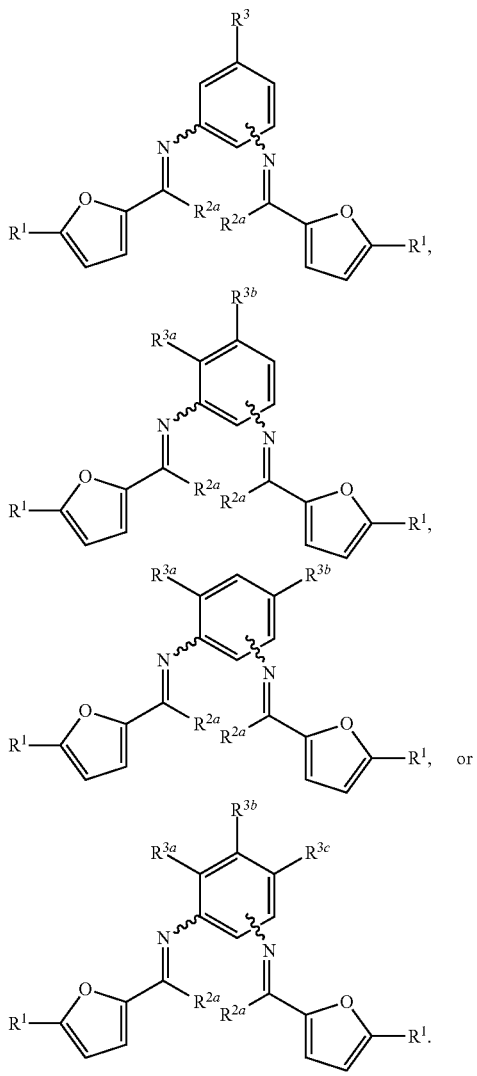

Suitable $R^3$ groups for imines of formula (C-3) may include any of the $R^3$ groups described above for imines of formula (C-1).

The position of the two imine groups in the imines of formula (C-3) may also vary relative to the benzyl moiety. In some embodiments, the two imine groups are in para, meta, or ortho positions. For example,

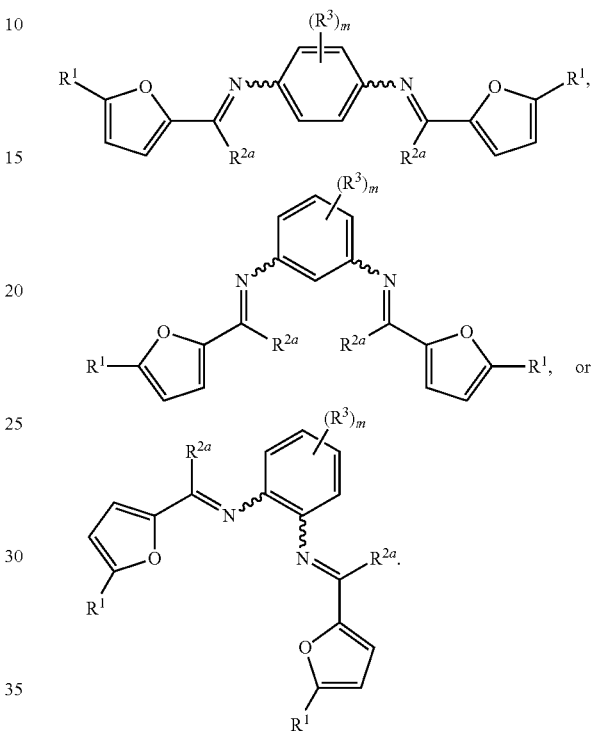

In one embodiment, the imine of formula (C-3) is:

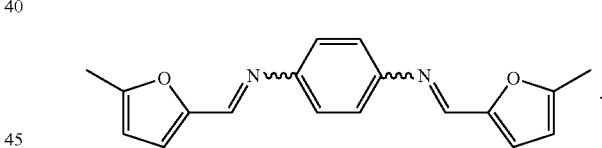

In other embodiments, the imines used in the methods described herein have the structure of formula (C-4):

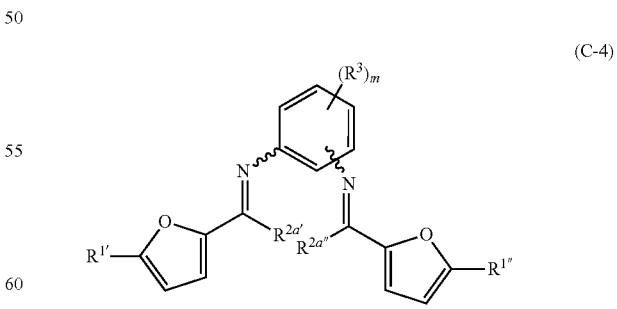

wherein:
$R^{1'}$ is as defined in formula (I');
$R^{2'}$ is as defined in formula (I");
$R^{2a'}$ is H or $C_{y-1}$ alkyl, wherein y is as defined in formula (I'), provided that $R^{2a'}$ is H when y is 1;

$R^{2a''}$ is H or $C_{y-1}$ alkyl, wherein y is as defined in formula (I''), provided that $R^{2a''}$ is H when y is 1;

m is 0, 1, 2, 3 or 4; and each $R^3$ is independently halo, alkyl, haloalkyl, cycloalkyl, alkoxy, or —C(O)O-alkyl.

In certain embodiments, $R^{1'}$ and $R^{1'''}$ are different. In one embodiment, $R^{1'}$ is H, and $R^{1'''}$ is an alkyl. For example, in one variation, the imine of formula (C-4) may be:

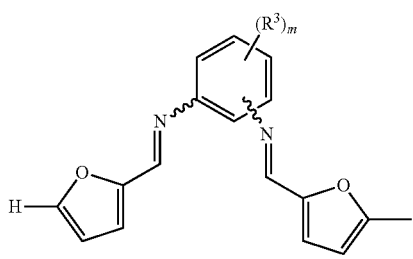

It should be understood that when an imine of formula (C-4) is used the imine reduction reaction, a mixture of alkylfurans of formula (I) may be produced.

In other embodiments, the imine of formula (C-1), (C-2), (C-3) or (C-4) has a pKa of between 2 and 6.5, or between 3 and 6, between 3 and 5, between 3 and 4, between 4 and 6, or between 4 and 5.

The imine of formula (C-1), (C-2), (C-3) or (C-4) may be a mixture of (E)- and (Z)-isomers, or can be resolved into its individual isomers using any suitable methods or techniques known in the art.

Imine Reduction

The imines of formula (C-1), (C-2), (C-3) or (C-4) described above can undergo imine reduction by reaction with a reducing agent in the presence of a catalyst, and optionally a solvent, to yield the alkylfurans of formula (I).

a) Reducing Agents

In one embodiment, the reducing agent is hydrogen gas. Hydrogen may be provided at a partial pressure of at least 5 psig, at least 10 psig, at least 15 psig, at least 20 psig, at least 25 psig, or at least 50 psig. In some embodiments, the hydrogen is provided at a partial pressure of between 5 and 50 psig, between 5 and 40 psig, between 5 and 30 psig, or between 10 and 20 psig. In one embodiment, the hydrogen is provided at a partial pressure of about 5 psig, about 10 psig, about 15 psig, about 20 psig, about 25 psig, about 30 psig, about 35 psig, about 40 psig, about 45 psig, or about 50 psig.

In other embodiments, the reducing agent may be any hydrogen donor capable of undergoing transfer hydrogenation, thereby reducing the imine compound to the alkylfuran. In other embodiments, the reducing agent may be a hydrogen donor such as cyclohexene or formic acid, which may undergo transfer hydrogenation to reduce the imine compound to the alkylfuran.

b) Catalyst

Any catalysts suitable for reduction of the imine of formula (C-1), (C-2), (C-3) or (C-4) may be used. The catalyst may include one or more metals. In some embodiments, the catalyst may include one or more transition metals. In certain embodiments, the catalyst may include a Group 8 metal, Group 9 metal, Group 10 metal, and Group 11 metal.

In some embodiments, the catalyst includes palladium, platinum, ruthenium, copper, or any combinations thereof.

In certain embodiments, the catalyst is a palladium catalyst. In one embodiment, the catalyst is palladium on carbon (Pd/C).

The catalyst may include one or more supported or unsupported metals. For example, the catalyst may be a solid-phase catalyst. In certain embodiments, the catalyst is present at surfaces of a support, including external or internal surfaces. Suitable supports may include, for example, carbon (including activated carbon), alumina, silica, ceria, titania, zirconia, niobia, zeolite (including mordenite), magnesia, clays, iron oxide, silicon carbide, aluminosilicates, and any modifications (including activation of a solid support), mixtures or combinations thereof. When a catalyst support is used, the metals may be deposited using any procedures known in the art. See e.g., Schwarz et al., *Chem. Rev.* 95, 477-510, (1995).

c) Solvent

A solvent may optionally be used in the imine reduction reaction. In some embodiments, the imine reduction reaction is performed neat.

In other embodiments, a solvent is used. In one embodiment, the solvent is acidic. In certain embodiments, the solvent has a pKa between 2 to 6.5, or between 4 and 5. In one embodiment, the solvent has a pKa of about 3, about 3.5, about 4, about 4.5, about 5, about 5.5, about 6, or about 6.5. Suitable solvents may include, for example, acetic acid, or p-toluenesulfonic acid. A combination of solvents may also be used.

It should be understood if a non-acidic solvent is used, acidic resins may be added to the reaction mixture.

In another embodiment, the solvent is neutral. In yet another embodiment, the solvent is basic.

d) Reaction Conditions

In some embodiments, the reaction may be performed in acidic conditions, such as at a pH of between 2 and 6.5, or between 4 and 5. In one embodiment, the solvent has a pKa of about 3, about 3.5, about 4, about 4.5, about 5, about 5.5, about 6, or about 6.5. It should be understood that the pH of the reaction may depend on the choice of solvent or other reagents that may be added to the reaction system, such as acidic resins.

The imine reduction reaction may be performed at any temperature suitable to produce the alkylfurans of formula (I). In some embodiments, the temperature is between −10° C. and 200° C., between −10° C. and 50° C., between 0° C. and 50° C., between 0° C. and 30° C., between 30° C. and 200° C., between 50° C. and 150° C., between 60° C. and 100° C., or between 50° C. and 80° C.

e) Intermediates

Without wishing to be bound by any theory, the imine of formula (C-1) or (C-2) may be converted into the alkylfuran of formula (I) via an amine intermediate of formula (D-1) or (D-2), respectively. The amine of formula (D-1) has the structure:

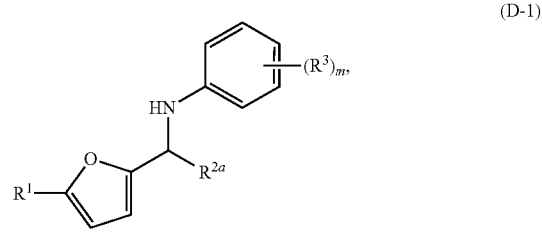

wherein:
R¹ is as defined in formula (I);
R²ᵃ is as defined in formula (C-1); and
R³ and m are each as defined in formula (C-1).
The amine of formula (D-2) has the structure:

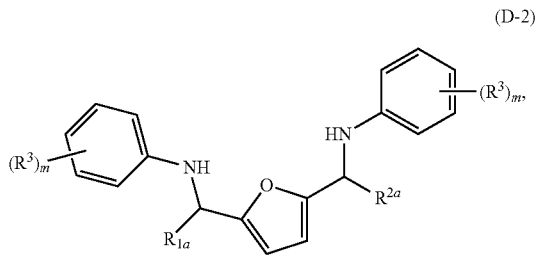

wherein:
R¹ᵃ is as defined in formula (C-2);
R²ᵃ is as defined in formula (C-2); and
R³ and m are each as defined in formula (C-2).

Without wishing to be bound by any theory, the imine of formula (C-3) may be converted into the alkylfuran of formula (I) via a diamine intermediate of formula (D-3). The diamine of formula (D-3) has the structure:

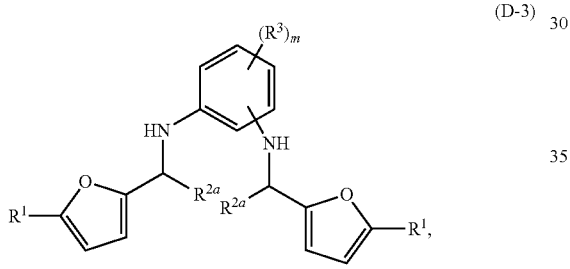

wherein R¹, R²ᵃ, R³ and m are each as defined in formula (C-3).

Without wishing to be bound by any theory, the imine of formula (C-4) may be converted into a mixture of alkyl-furans of formula (I) via a diamine intermediate of formula (D-4). The diamine of formula (D-4) has the structure:

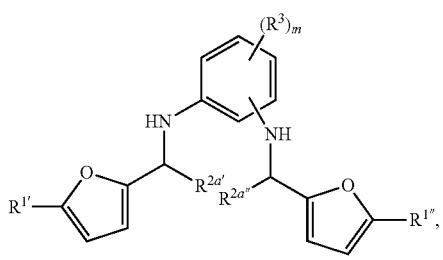

wherein R¹′, R¹″, R²ᵃ′, R²ᵃ″, m and R³ are each as defined in formula (C-4).

The amine of formula (D-1), (D-2), (D-3) or (D-4) may be isolated, and optionally purified, using any methods known in the art. The isolated amine of formula (D-1), (D-2), (D-3) or (D-4) may be further reacted to produce alkylfurans of formula (I).

f) Catalyst Promoters and Ring Saturation Products

In some variations of the methods described herein, one or more catalyst promoters may be added to reduce the formation of ring saturation products. Such ring saturation products may include, for example, an imine of formula (X-1), (X-2), (X-3) or (X-4):

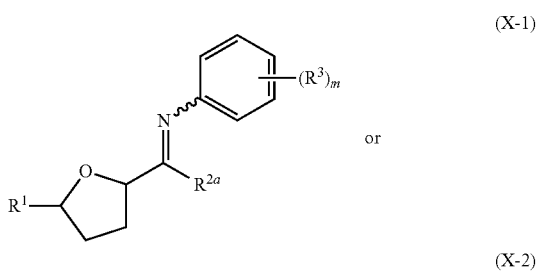

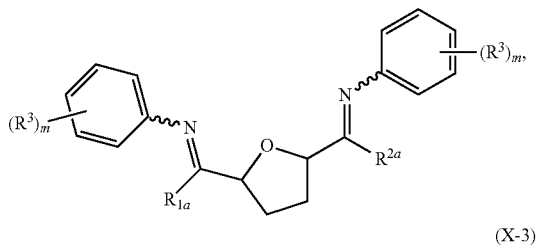

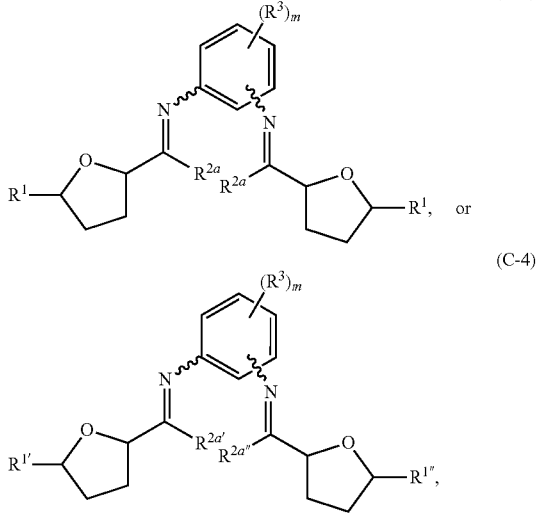

wherein:
R¹, R²ᵃ, R³ and m for formula (X-1) is as defined for formula (C-1),
R¹ᵃ, R²ᵃ, R³ and m for formula (X-2) is as defined for formula (C-2),
R¹, R²ᵃ, R³ and m for formula (X-3) is as defined for formula (C-3), and
R¹′, R¹″, R²ᵃ′, R²ᵃ″, R³ and m for formula (X-4) is as defined for formula (C-4).

Such catalyst promoters may be any suitable substances added to a catalyst (e.g. a solid catalyst) to improve the catalyst's performance in a chemical reaction. One of skill in the art would recognize that catalyst promoters on their own may have little or no catalytic effect. Such promoters interact with active components of the catalysts, and can alter the chemical effect on the catalyzed substance. Suitable catalyst promoters may include, for example, sulfur, pyridine, lithium chloride (LiCl), lithium bromide (LiBr), dimethylamine, triethylamine, diisopropylamine, tertbutylamine, hydrochloric acid (HCl), and sulfuric acid ($H_2SO_4$). A combination of catalyst promoters may also be used.

When such additional reagents are used in the methods to form the imine of formula (C-1), (C-2), (C-3) or (C-4), the amount of ring saturation products is reduced. In some variations, the amount of ring saturation products in the reaction mixture is less than 80%, less than 70%, less than 60%, less than 50%, less than 40%, less than 30%, less than 25%, less than 20%, less than 15%, less than 10%, less than 5%, or less than 1% by weight of the reaction mixture.

g) Yield, Conversion and Selectivity

The yield of the alkylfuran produced takes into account the conversion of the imine compound into the alkylfuran, and the selectivity for the alkylfuran over other byproducts (e.g., ring saturation products) that may be formed.

The difference between yield, conversion and selectivity is explained in the examples provided below. For example, with respect to the conversion of the imine compound into alkylfuran, the reaction can be generalized as follows:

$$aA + bB \rightarrow cC + dD,$$

where "A" represents the moles of the imine compound; "B" represents the moles of hydrogen; "C" represents the moles of alkylfuran; "D" represents the moles of aniline compound produced; and "a", "b", "c" and "d" are stoichiometric coefficients. It should be understood that the equation provided above does not depict the formation of other products, e.g., ring saturation products.

Conversion of A is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant; and $A_o - A_f$ is the number of moles consumed by the reaction.

Selectivity of product C on reactant A is the stoichiometrically relative amount of product C produced from the converted amount of reactant A, as expressed as a percentage by the following equation:

$$\text{Selectivity (\%)} = \frac{Cf * \frac{a}{c}}{Ao - Af} * 100\%,$$

where $A_o$ is the starting moles of reactant A; $A_f$ is the final number of moles of reactant A; and $C_f$ is the number of moles of product C that is produced. In some embodiments where "a/c"=1, and the equation can be simplified to:

$$\text{Selectivity (\%)} = \frac{Cf}{Ao - Af} * 100\%.$$

The yield of product C is the percentage of reactant A that is converted into product C, as expressed by the following equation:

Yield(%)=Conversion(%)*Selectivity(%)

In certain embodiments, the methods described herein have an alkylfuran yield of at least 10%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% to 100%, between 10% to 90%, between 20% to 80%, between 30% to 80%, between 40% to 80%, between 50% to 80%, or between 60% to 80% by weight.

In certain embodiments, the methods described herein have an alkylfuran selectivity of at least 10%, at least 20%, at least 30%, at least 40%, at least 50%, at least 60%, at least 70%, at least 80%, at least 90%, or at least 99%. In other embodiments, the selectivity is between 40% to 99%, between 40% to 95%, between 40% to 90%, between 40% to 80%, between 50% to 99%, between 50% to 95%, between 50% to 90%, between 50% to 80%, between 60% to 99%, between 60% to 95%, between 60% to 90%, between 60% to 80%, between 70% to 99%, between 70% to 95%, between 70% to 90%, or between 70% to 80%.

Compositions

Provided herein is a composition that includes: an imine of formula (C-1), (C-2), (C-3) or (C-4); a reducing agent; and catalyst. In some aspects, provided is a composition that includes: an unsubstituted or substituted ((5-methylfuran-2-yl)methylene)aniline or an unsubstituted or substituted bis((5-methylfuran-2-yl)methylene)benzene-1,4-diamine; a reducing agent; and catalyst. In other aspects, provided is a composition that includes: an unsubstituted or substituted bis((5-methylfuran-2-yl)methylene)benzenediamine; a reducing agent; and catalyst. In some embodiments, the composition further includes a solvent. In certain embodiments, the composition further includes one or more alkylfurans of formula (I). It should be understood that any of the variations of the imines, reducing agents, catalysts, solvents (if present), and alkylfurans described herein may be present in such composition.

For example, in one exemplary embodiment, the composition includes:

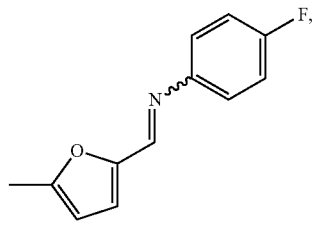

hydrogen and palladium catalyst. In some variations, the composition further includes a solvent, such as acetic acid. In other variations, the composition further includes

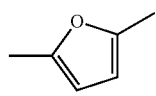

In another exemplary embodiment, the composition includes:

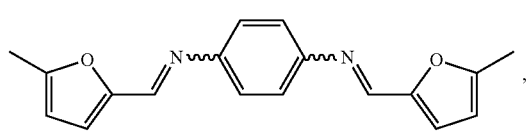

hydrogen and palladium catalyst. In some variations, the composition further includes a solvent, such as acetic acid. In other variations, the composition further includes

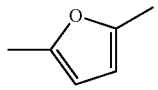

In some embodiments, the composition further includes one or more catalyst promoters that may reduce the formation of ring saturation products. Any of the catalyst promoters described for the method above may be present in the composition. For, in one exemplary variation, the composition further includes one or more catalyst promoters selected from sulfur, pyridine, lithium chloride (LiCl), lithium bromide (LiBr), dimethylamine, triethylamine, diisopropylamine, tertbutylamine, hydrochloric acid (HCl), and sulfuric acid ($H_2SO_4$), or any combinations thereof. Further, in certain embodiments, the amount of ring saturation products in the composition is less than 80%, less than 70%, less than 60%, less than 50%, less than 40%, less than 30%, less than 25%, less than 20%, less than 15%, less than 10%, less than 5%, or less than 1% by weight of the reaction mixture.

Methods of Preparing Imine of Formula (C-1), (C-2), (C-3) or (C-4)

The imines of formula (C-1), (C-2), (C-3) or (C-4) used in the methods described above may be commercially available, or prepared from reacting furfurals or derivatives thereof with an optionally substituted aniline under conditions suitable for the formation of the imine.

Furfural and Derivatives Thereof

In some embodiments, compounds of formula (A-1) may be used as a starting material in the reaction to produce imines of formula (C-1), (C-3) or (C-4). The compounds of formula (A-1) have the structure:

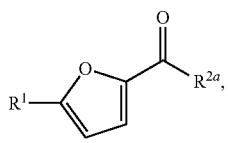

(A-1)

wherein:
$R^1$ is as defined in formula (I); and
$R^{2a}$ is $C_{y-1}$ alkyl, wherein y is as defined in formula (I), provided that $R^{2a}$ is H when y is 1.

For example, with reference again to FIG. 2, the compound of formula (A-1) used in process 200 is 5-methylfurfural, in which $R^1$ is an alkyl having 1 carbon atom (i.e., methyl), and $R^{2a}$ is H.

In other embodiments, compounds of formula (A-2) may be used as a starting material in the reaction to produce imines of formula (C-2). The compounds of formula (A-2) have the structure:

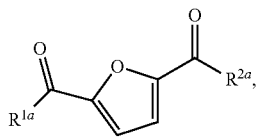

(A-2)

wherein:
$R^{1a}$ is $C_{x-1}$ alkyl, wherein x is as defined in formula (I), provided that $R^{1a}$ is H when x is 1, and
$R^{2a}$ is $C_{y-1}$ alkyl, wherein y is as defined in formula (I), provided that $R^{2a}$ is H when y is 1.

For example, the compound of formula (A-2) used in the methods described herein may be 1,1'-(furan-2,5-diyl)diethanone, in which $R^{1a}$ and $R^{2a}$ are each H. It should be understood that $R^{1a}$ and $R^{2a}$ may be the same or different, and may vary depending on the imine of formula (C-2) to be prepared.

Aniline Compounds

The optionally substituted anilines used in the methods described above have the structure:

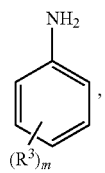

(B)

wherein m and $R^3$ is as defined in formula (C-1) or (C-2).

It should be understood that m and $R^3$ (if present) may be selected based on the imine of formula (C-1) or (C-2) to be prepared. The aniline of formula (B) may be unsubstituted (i.e., m is 0) or substituted (i.e., m is 1, 2, 3, 4 or 5). As discussed above for the imines of formula (C-1) or (C-2), when more than one $R^3$ group is present on the ring, each $R^3$ group is denoted as $R^{3a}$, $R^{3b}$, $R^{3c}$, $R^{3d}$, and $R^{3e}$ (if present).

When m is 1, the $R^3$ group may be located on any position of the ring. For example, the $R^3$ group may be located on the ring as depicted below:

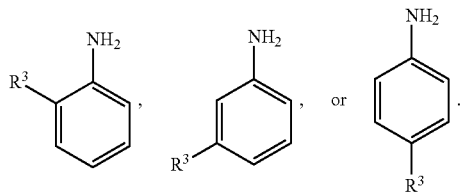

When m is 2, the two $R^3$ groups may be located on any position of the ring. For example, the two $R^3$ groups may be located on the ring as depicted below:

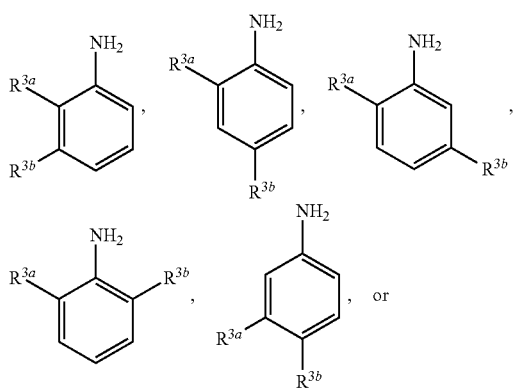

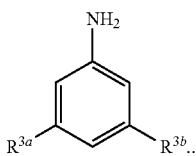

When m is 3, the three $R^3$ groups may be located on any position of the ring. For example, the three $R^3$ groups may be located on the ring as depicted below:

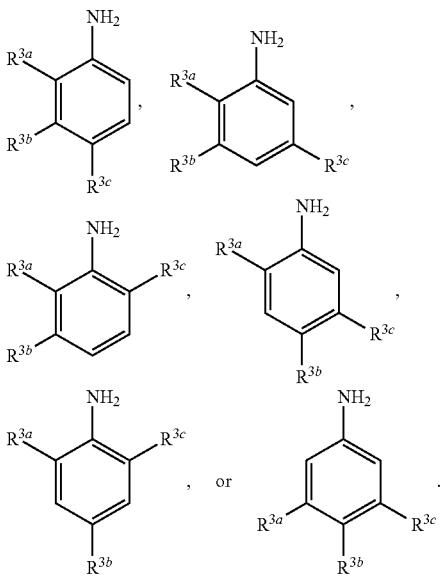

When m is 4, the four $R^3$ groups may be located on any position of the ring. For example, the four $R^3$ groups may be located on the ring as depicted below:

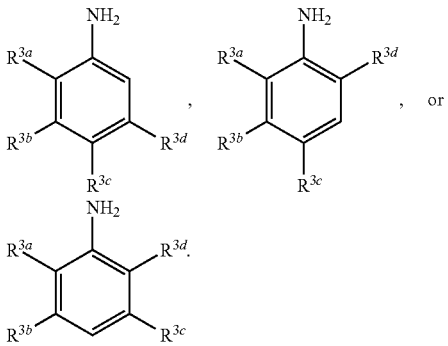

When m is 5, the five $R^3$ groups may be located on any position of the ring. For example, the five $R^3$ groups may be located on the ring as depicted below:

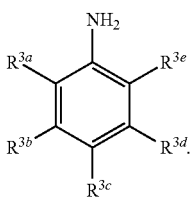

One of skill in the art would recognize that the amount of aniline of formula (B) used in the reaction will vary depending on whether the compound of formula (A-1) or (A-2) is used as the other starting material. For example, when a compound of formula (A-1) is used, a slight stoichiometric excess (e.g., 1.1-1.5 equivalents) of the aniline may be used. When a compound of formula (A-2) is used, at least two times the stoichiometric amount (e.g., 2-3 equivalents) of the aniline may be used.

In some embodiments, the aniline of formula (B) is selected from

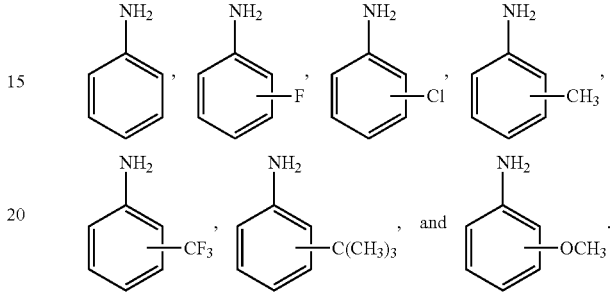

In certain embodiments, the aniline of formula (B) is selected from:

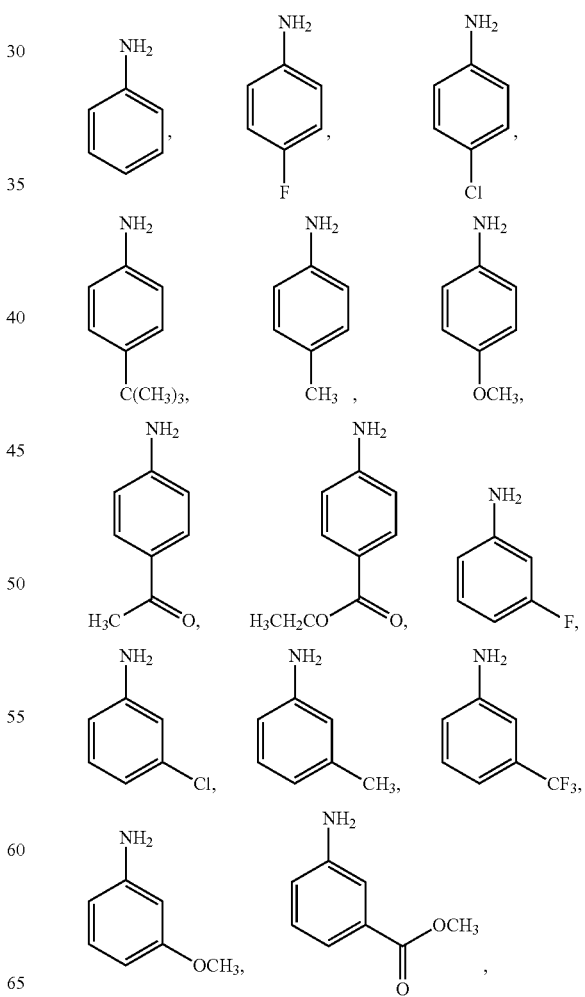

-continued

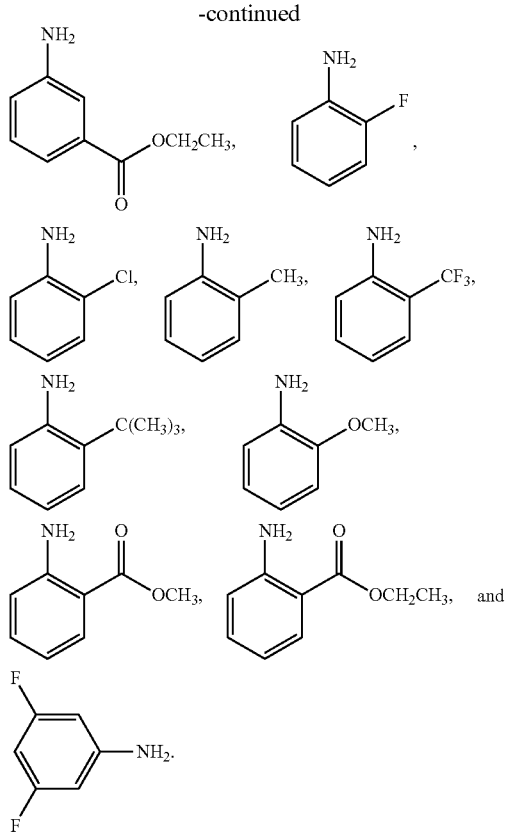

In one embodiment, the aniline of formula (B) is selected from:

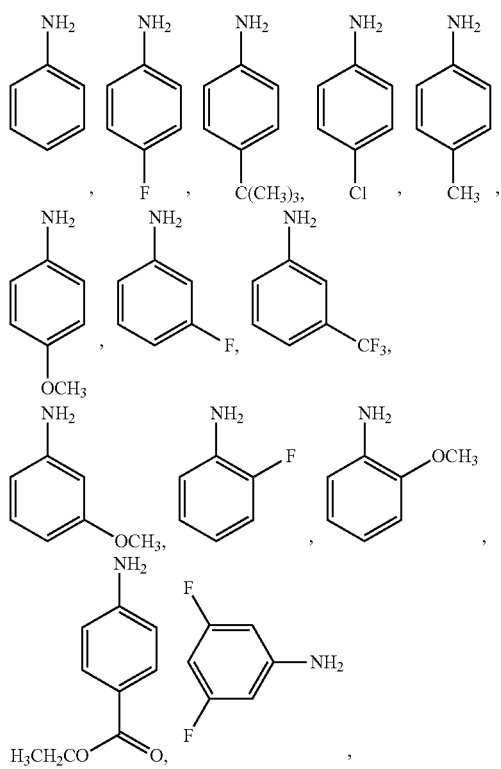

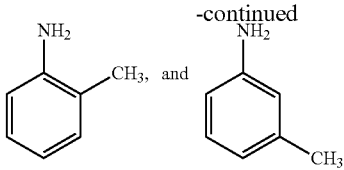

Diaminobenzyl Compounds

The optionally substituted diaminobenzyl compounds used in the methods described above have the structure:

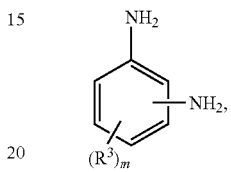

(B-1)

wherein m and $R^3$ is defined in formula (C-3).

It should be understood that m and $R^3$ (if present) may be selected based on the imine of formula (C-3) to be prepared. The diaminobenzene of formula (B-1) may be unsubstituted (i.e., m is 0) or further substituted (i.e., m is 1, 2, 3, or 4). As discussed above for the imines of formula (C-3), when more than one $R^3$ group is present on the ring, each $R^3$ group is denoted as $R^{3a}$, $R^{3b}$, $R^{3c}$, and $R^{3d}$ (if present). The $R^3$ groups (if present) may be located on any position of the ring. For example, the $R^3$ groups may be located as follows:

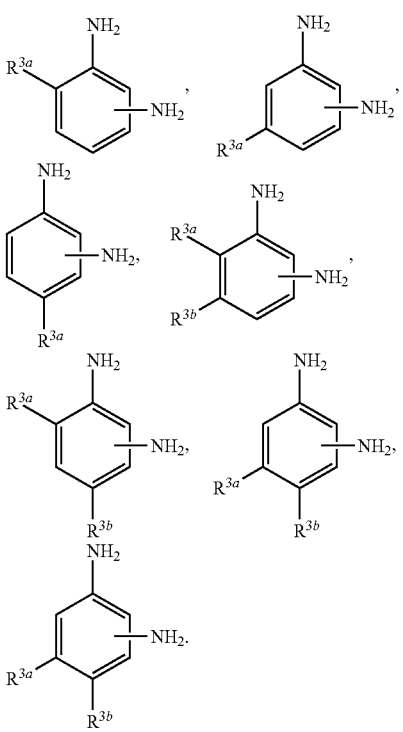

The position of the two amino groups of the diaminobenzene of formula (B-1) may also vary. In some embodiments, the two amino groups are in para, ortho or meta positions. For example, the diaminobenzene may be:

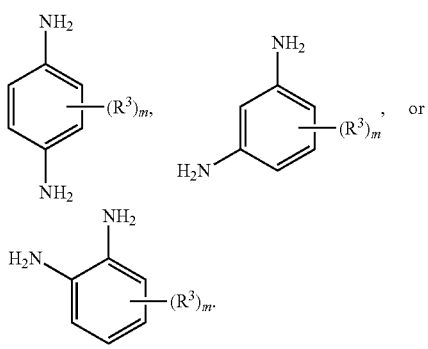

In some embodiments, the diaminobenzene of formula (B-1) is:

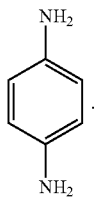

Imine Formation a) Reaction Conditions

The compounds of formula (A-1) or (A-2) described above may react with the aniline of formula (B) or the diaminobenzene of formula (B-1) at elevated temperatures to yield imines of formula (C-1) or (C-2), or imines of formula (C-3), respectively. The imine formation reaction may be performed at any temperature suitable to produce the imines of formula (C-1), (C-2), (C-3) or (C-4). In some embodiments, imine formation may be performed at temperatures, for example, between 20° C. and 150° C., between 20° C. and 100° C., or between 40° C. and 80° C.

In some embodiments, the reaction may be performed neat. In other embodiments, the reaction may be performed using any suitable solvents, such as acetic acid or toluene.

b) Yield, Conversion and Selectivity

The yield of the imine compound produced takes into account the conversion of the furfural or derivative thereof into the imine compound, and the selectivity for the imine compound over other byproducts that may be formed.

The difference between yield, conversion and selectivity is explained in the examples provided below. For example, with respect to the conversion of the furfural or derivative thereof into the imine compound, the reaction can be generalized as follows:

$$aA + bB \rightarrow cC,$$

where "A" represents the moles of the furfural or derivative thereof; "B" represents the moles of the aniline or diaminobenzene compound; "C" represents the moles of the imine compound; and "a", "b" and "c" are stoichiometric coefficients. It should be understood that the equation provided above depicts the production of one imine compound, and does not depict the formation of other products.

Conversion of A is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant A; and $A_o - A_f$ is the number of moles consumed by the reaction.

Selectivity of product C on reactant A is the stoichiometrically relative amount of product C produced from the converted amount of reactant A, as expressed as a percentage by the following equation:

$$\text{Selectivity (\%)} = \frac{Cf * \frac{a}{c}}{Ao - Af} * 100\%,$$

where $A_o$ is the starting moles of reactant A; $A_f$ is the final number of moles of reactant A; and $C_f$ is the number of moles of product C that is produced. In some embodiments where "a/c"=1, and the equation can be simplified to:

$$\text{Selectivity (\%)} = \frac{Cf}{Ao - Af} * 100\%.$$

The yield of product C is the percentage of reactant A that is converted into product C, as expressed by the following equation:

Yield(%)=Conversion(%)*Selectivity(%)

In certain embodiments, the methods described herein have an imine compound yield of at least 10%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% to 100%, between 10% to 90%, between 20% to 80%, between 30% to 80%, between 40% to 80%, between 50% to 80%, or between 60% to 80% by weight.

In certain embodiments, the methods described herein have an imine compound selectivity of at least 10%, at least 20%, at least 30%, at least 40%, at least 50%, at least 60%, at least 70%, at least 80%, at least 90%, or at least 99%. In other embodiments, the selectivity is between 40% to 99%, between 40% to 95%, between 40% to 90%, between 40% to 80%, between 50% to 99%, between 50% to 95%, between 50% to 90%, between 50% to 80%, between 60% to 99%, between 60% to 95%, between 60% to 90%, between 60% to 80%, between 70% to 99%, between 70% to 95%, between 70% to 90%, or between 70% to 80%.

Compositions

Provided is also a composition that includes: a compound of formula (A-1) and/or (A-2); and an aniline of formula (B) or a diaminobenzene of formula (B-1). In some embodiments, the composition further includes an imine of formula (C-1), (C-2), (C-3) or (C-4). It should be understood that any of the furfural derivatives, and aniline compounds or diaminobenzene compounds described herein may be present in such compositions.

For example, in one exemplary embodiment, the composition includes:

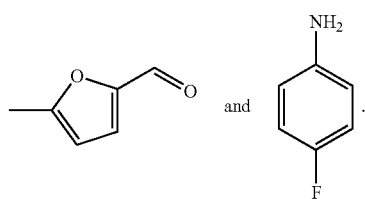

In one variation, the composition further includes:

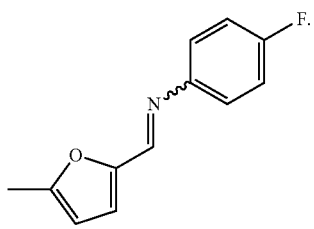

In another exemplary embodiment, the composition includes:

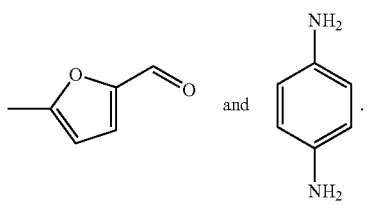 .

In one variation, the composition further includes:

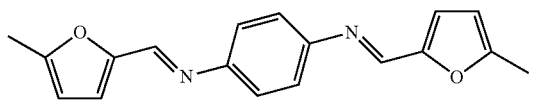 .

Uses of the Alkylfurans of Formula (I)

The alkylfurans of formula (I) may be used as or to prepare fuels and other products. For example, 2,5-dimethylfuran may be used as a fuel, with an energy density comparable to gasoline. 2,5-dimethylfuran may also be used to prepare para-xylene and terephthalic acid using any suitable methods known in the art. Para-xylene and terephthalic acid may then be used to prepare polyesters.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−10%.

It should also be understood that reference to "between" two values or parameters herein includes (and describes) embodiments that include those two values or parameters per se. For example, description referring to "between x and y" includes description of "x" and "y" per se.

Enumerated Embodiments

The following enumerated embodiments are representative of some aspects of the invention.

1. A method for preparing an alkylfuran of formula (I):

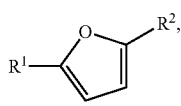

wherein $R^1$ is H or $C_x$ alkyl, wherein x is an integer equal to or greater than 1;

wherein $R^2$ is $C_y$ alkyl, wherein y is an integer equal to or greater than 1; and wherein the method comprises: reducing an imine of formula (C-1) or (C-2) to produce the alkylfuran of formula (I), wherein the imine of formula (C-1) or (C-2) is:

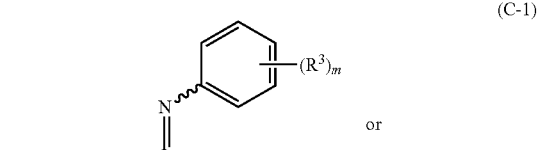

 or

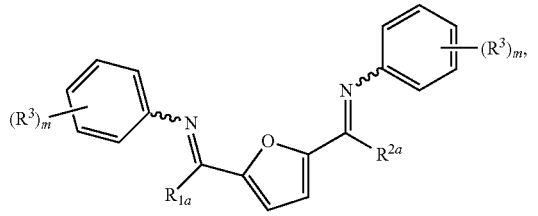

wherein:

$R^1$ is as defined in formula (I);

$R^{1a}$ is H or $C_{x-1}$ alkyl, wherein x is as defined in formula (I), provided that $R^{1a}$ is H when x is 1;

$R^{2a}$ is H or $C_{y-1}$ alkyl, wherein y is as defined in formula (I), provided that $R^{2a}$ is H when y is 1;

m is an integer equal to or greater than 0; and each $R^3$ is independently halo, alkyl, haloalkyl, cycloalkyl, alkoxy, or —C(O)O-alkyl.

2. A method for preparing an alkylfuran of formula (I):

wherein $R^1$ is H or $C_x$ alkyl, wherein x is an integer equal to or greater than 1;

wherein $R^2$ is $C_y$ alkyl, wherein y is an integer equal to or greater than 1; and wherein the method comprises:

a) providing an imine of formula (C-1) or (C-2):

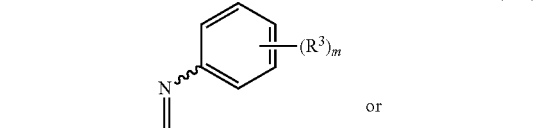

 or

-continued

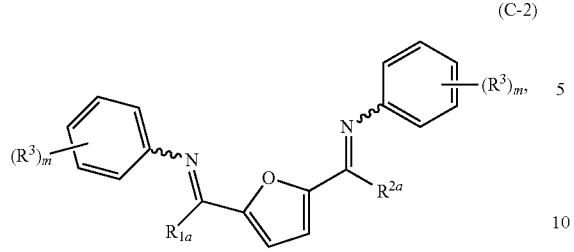
(C-2)

wherein:
R$^1$ is as defined in formula (I);
R$^{1a}$ is H or C$_{x-1}$ alkyl, wherein x is as defined in formula (I), provided that R$^{1a}$ is H when x is 1;
R$^{2a}$ is H or C$_{y-1}$ alkyl, wherein y is as defined in formula (I), provided that R$^{2a}$ is H when y is 1;
m is an integer equal to or greater than 0; and
each R$^3$ is independently halo, alkyl, haloalkyl, cycloalkyl, alkoxy, or —C(O)O-alkyl; and
b) reacting the imine of formula (C-1) or (C-2) with a reducing agent in the presence of a catalyst to produce the alkylfuran of formula (I).

3. The method of embodiment 1 or 2, wherein R$^1$ is H.
4. The method of embodiment 1 or 2, wherein R$^1$ is C$_x$ alkyl.
5. The method of embodiment 4, wherein x is 1, 2, 3, 4, 5, 6, 7, 8, 9 or 10.
6. The method of any one of embodiments 1 to 5, wherein y is 1, 2, 3, 4, 5, 6, 7, 8, 9 or 10.
7. The method of embodiment 1 or 2, wherein R$^1$ is H, and R$^2$ is methyl.
8. The method of embodiment 1 or 2, wherein R$^1$ and R$^2$ are both methyl.
9. The method of any one of embodiments 1 to 8, wherein m is 0, 1, 2, 3, 4 or 5.
10. The method of embodiment 9, wherein m is 0.
11. The method of embodiment 9, wherein m is 1 or 2.
12. The method of any one of embodiments 1 to 11, wherein each R$^3$ is independently chloro, fluoro, methyl, ethyl, propyl, butyl, —CF$_3$, —CHF$_2$, —CH$_2$F, methoxy, ethoxy, propoxy, butoxy, —CO$_2$-methyl, —CO$_2$-ethyl, —CO$_2$-propyl, or —CO$_2$-butyl.
13. The method of any one of embodiments 1 to 8, wherein the imine of formula (C-1) is selected from the group consisting of:

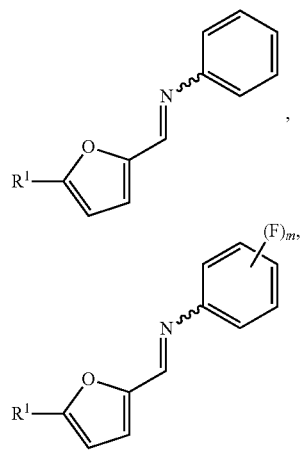

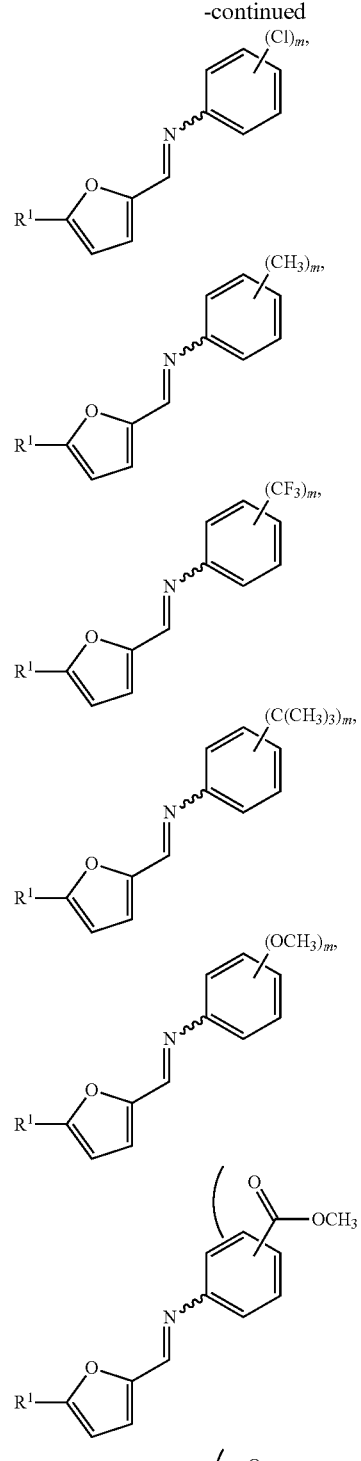

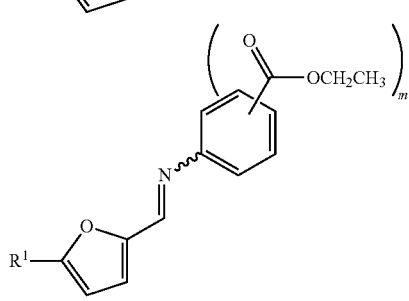

14. The method of any one of embodiments 1 to 8, wherein the imine of formula (C-1) is selected from the group consisting of:
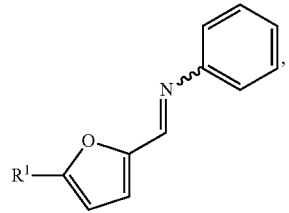
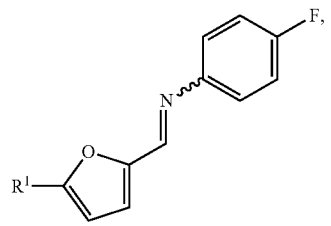
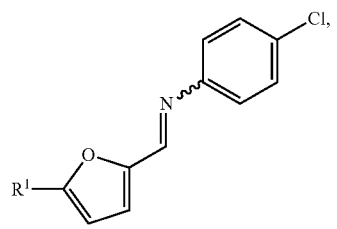
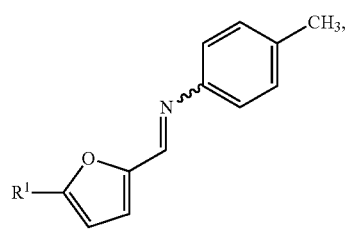
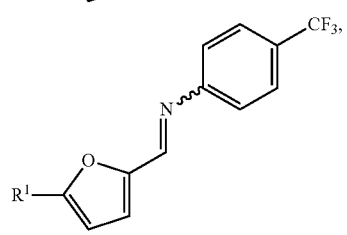
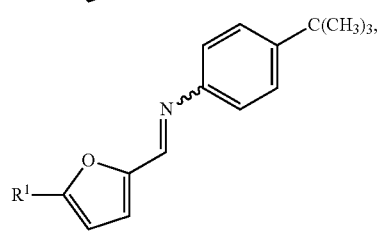
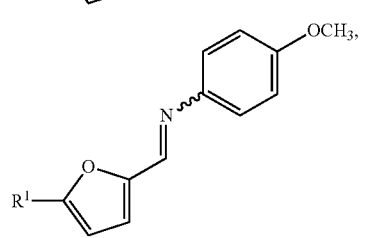
-continued
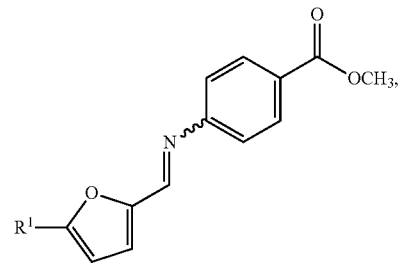
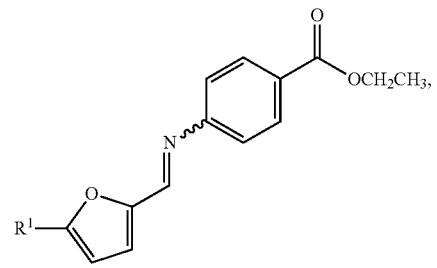
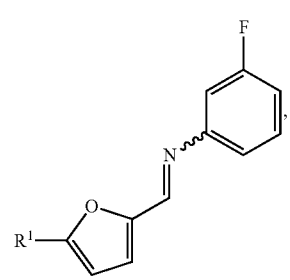
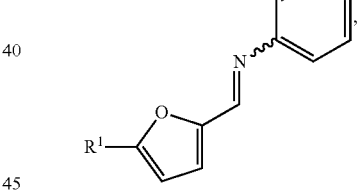
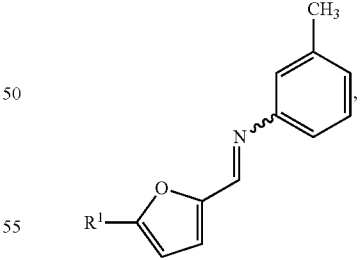
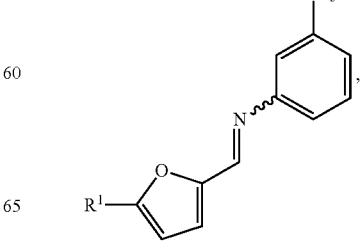

-continued
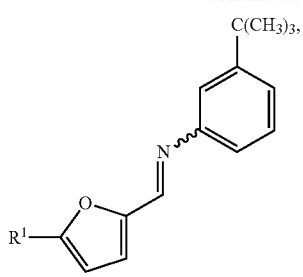
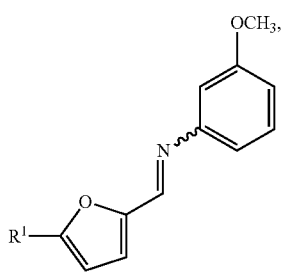
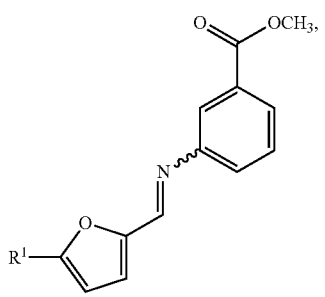
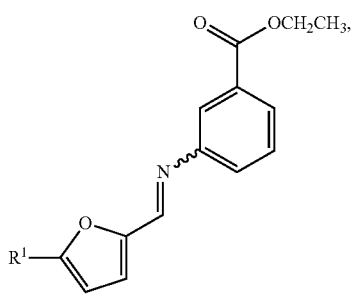
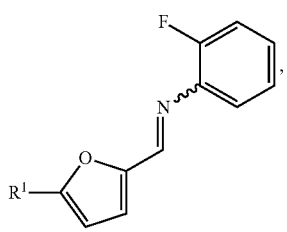
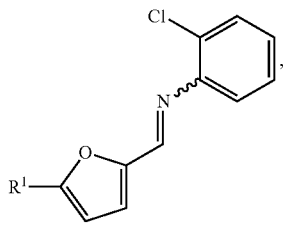
-continued
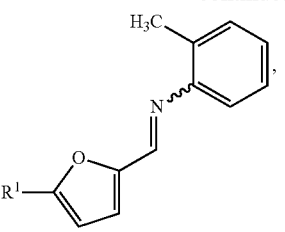
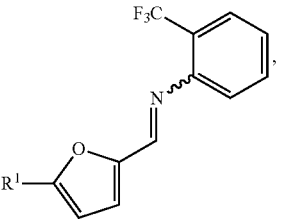
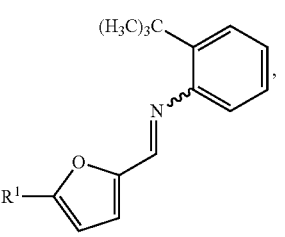
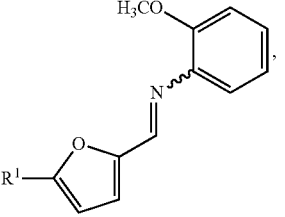
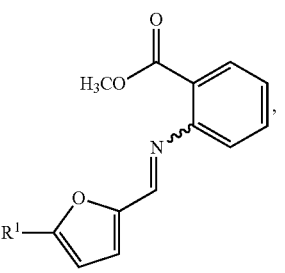
and
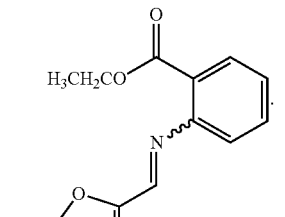
15. The method of any one of embodiments 1 to 8, wherein the imine of formula (C-2) is selected from the group consisting of:

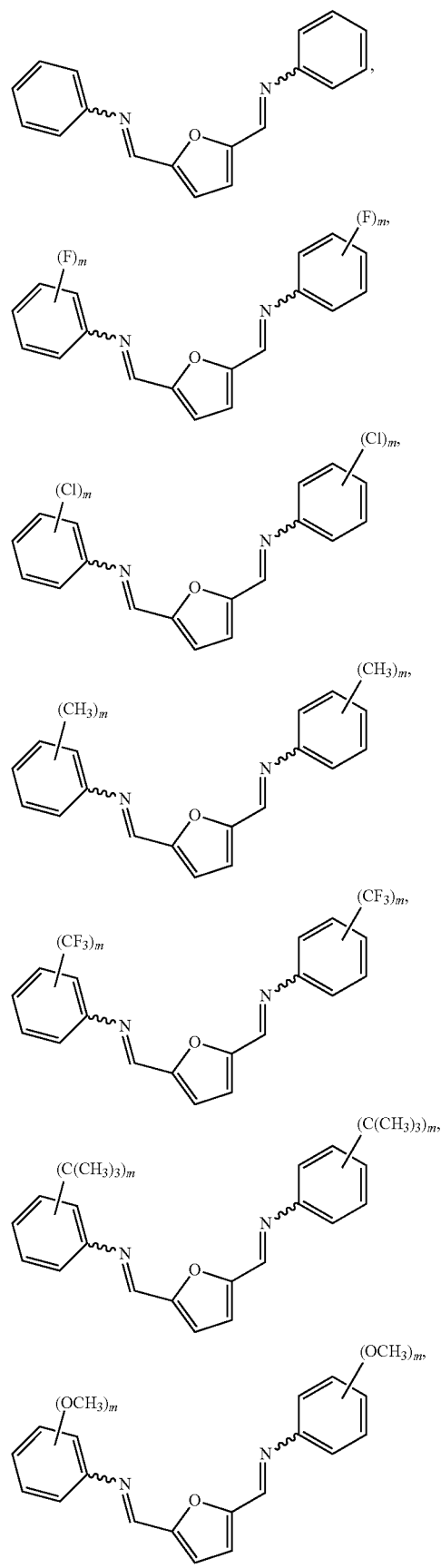
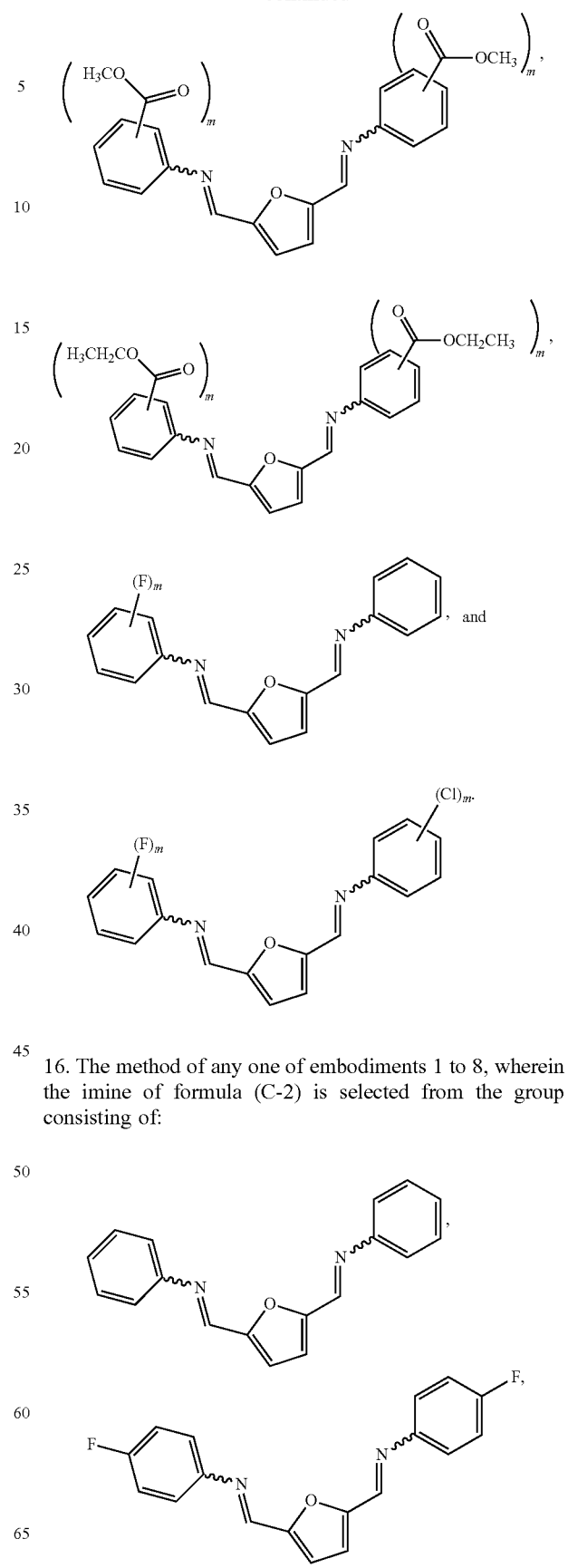
16. The method of any one of embodiments 1 to 8, wherein the imine of formula (C-2) is selected from the group consisting of:

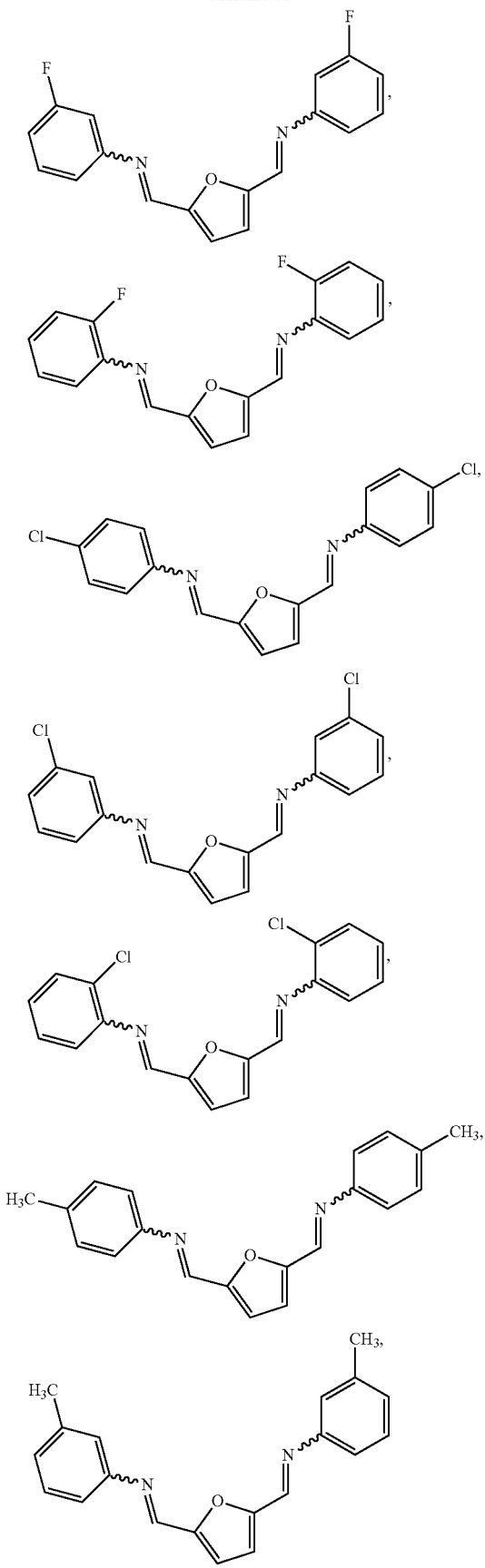
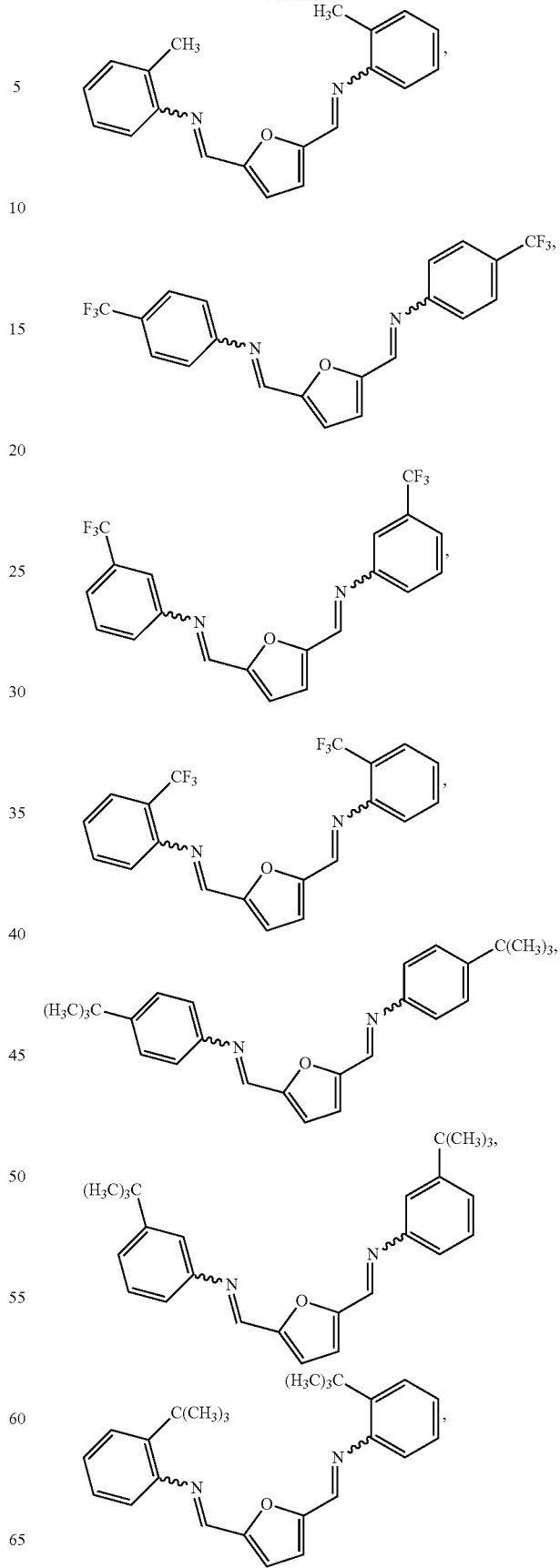

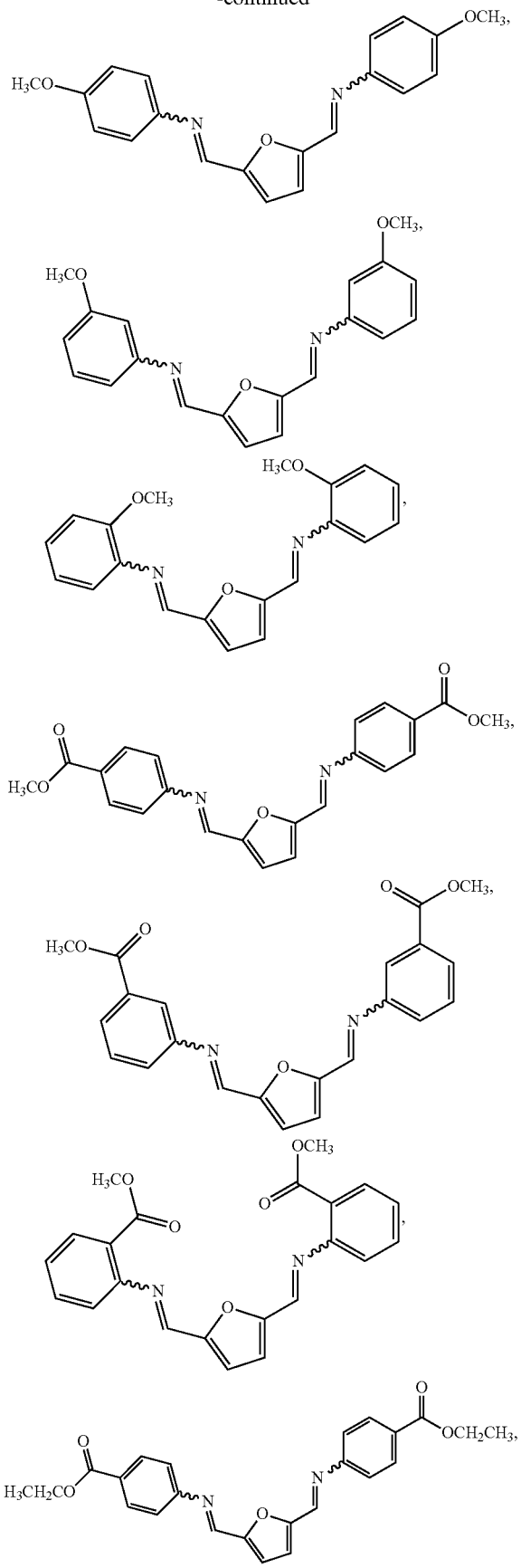

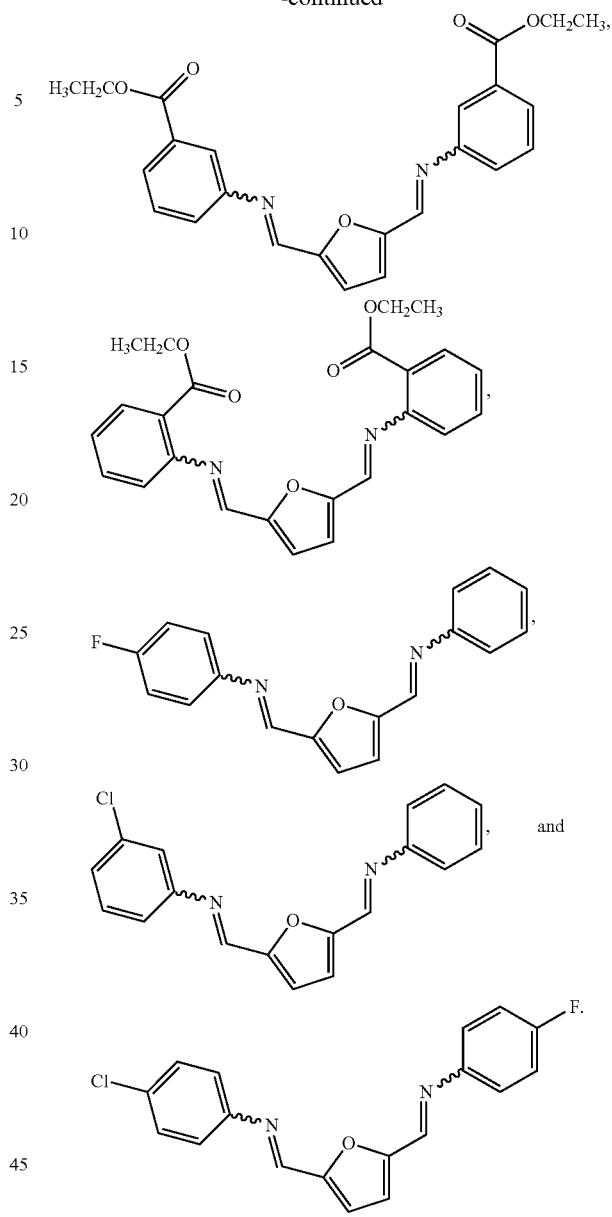

17. The method of any one of embodiments 2 to 16, wherein the catalyst is a palladium catalyst.

18. The method of embodiment 17, wherein the catalyst is palladium on carbon.

19. The method of any one of embodiments 2 to 17, wherein the imine of formula (C-1) or (C-2) is reacted with the hydrogen in the presence of the catalyst, and further in the presence of a solvent.

20. The method of embodiment 19, wherein the solvent has a pKa between 2 to 6.5.

21. The method of any one of embodiments 1 to 20, wherein the reducing agent is hydrogen or transfer hydrogenation.

22. The method of any one of embodiments 1 to 21, wherein the reducing agent is cyclohexene or formic acid.

23. The method of any one of embodiments 1 to 22, wherein the imine of formula (C-1) or (C-2) is provided by:

i) providing a compound of formula (A-1) or (A-2):

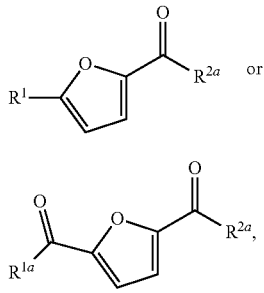

wherein:
R$^1$ is as defined in formula (I);
R$^{1a}$ and R$^{2a}$ are each as defined in formula (C-1) or (C-2);

ii) providing an aniline of formula (B);

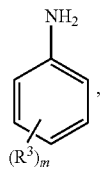

wherein:
m and R$^3$ are as defined in formula (C-1) or (C-2); and iii) reacting the compound of formula (A-1) or (A-2) with the aniline of formula (B) to provide the imine of formula (C-1) or (C-2).

24. The method of embodiment 23, wherein the aniline of formula (B) is:

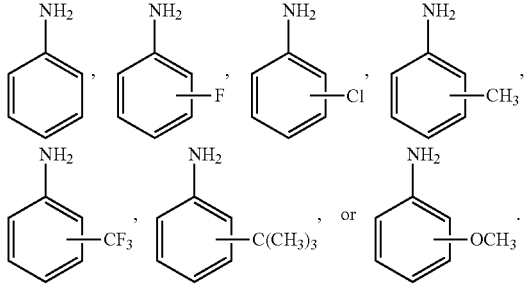

25. The method of embodiment 23, wherein the aniline of formula (B):

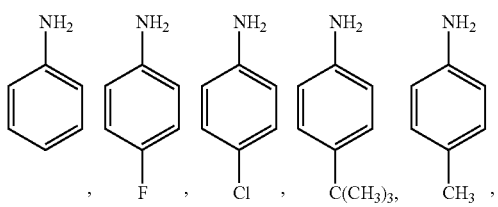

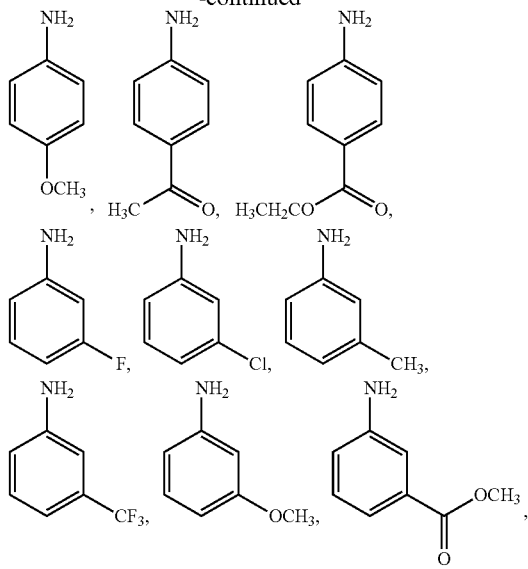

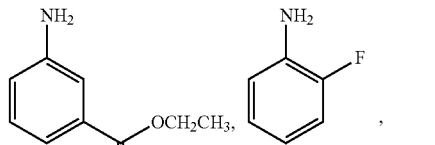

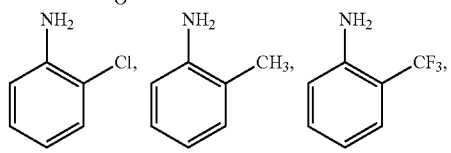

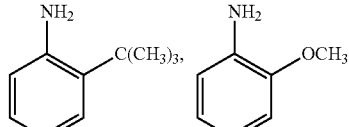

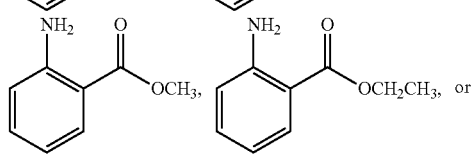

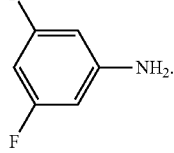

26. The method of any one of embodiments 22 to 25, wherein the compound of formula (A-1) or (A-2) is reacted with the aniline of formula (B) at a temperature of at least 40° C.

27. The method of any one of embodiments 1 to 26, wherein: the alkylfuran of formula (I) is:

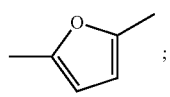

and
the imine of formula (C-1) or (C-2) is:

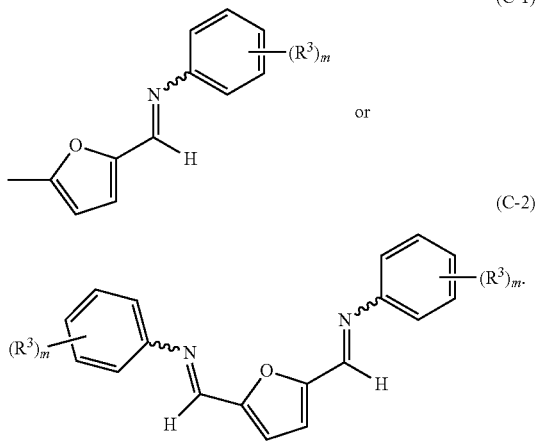

28. The method of any one of embodiments 1 to 26, wherein:
the alkylfuran of formula (I) is:

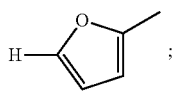

and
the imine of formula (C-1) is:

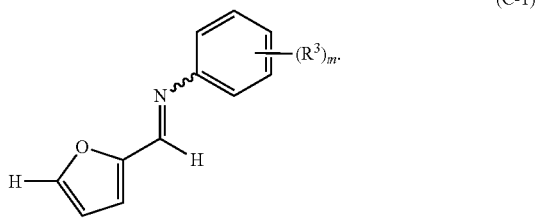

29. A method for preparing 2,5-dimethylfuran, comprising: reducing an unsubstituted or substituted ((5-methylfuran-2-yl)methylene)aniline to produce 2,5-dimethylfuran.

30. A method for preparing 2,5-dimethylfuran, comprising:
a) providing an unsubstituted or substituted ((5-methyl-furan-2-yl)methylene)aniline;
b) reacting the unsubstituted or substituted ((5-methyl-furan-2-yl)methylene)aniline with a reducing agent in the presence of a catalyst to produce 2,5-dimethylfuran.

31. The method of embodiment 28 or 29, wherein the ((5-methylfuran-2-yl)methylene)aniline provided is:
unsubstituted ((5-methylfuran-2-yl)methylene)aniline; or
((5-methylfuran-2-yl)methylene)aniline substituted on the aniline moiety with one to five substituents independently selected from the group consisting of halo, alkyl, haloalkyl, cycloalkyl, alkoxy, and —C(O)O-alkyl.

32. The method of embodiment 30 or 31, wherein the catalyst is palladium catalyst, platinum catalyst, ruthenium catalyst, copper catalyst, or any combinations thereof.

33. The method of embodiment 32, wherein the catalyst is palladium on carbon.

34. The method of any one of embodiments 30 to 33, wherein the unsubstituted or substituted ((5-methylfuran-2-yl)methylene)aniline is reacted with the reducing agent in the presence of the catalyst, and further in the presence of a solvent.

35. The method of embodiment 34, wherein the solvent has a pKa between 2 to 6.5.

36. The method of any one of embodiments 30 to 35, wherein the unsubstituted or substituted ((5-methylfuran-2-yl)methylene)aniline is provided by:
i) providing 5-methylfurfural;
ii) providing an unsubstituted or substituted aniline;
iii) reacting the 5-methylfurfural with the unsubstituted or substituted aniline to provide the unsubstituted or substituted ((5-methylfuran-2-yl)methylene)aniline.

37. The method of any one of embodiments 36, wherein the 5-methylfurfural is reacted with the unsubstituted or substituted aniline at a temperature of at least 40° C.

38. The method of embodiment 36 or 37, wherein the aniline provided is:
unsubstituted aniline; or
aniline substituted with one to five substituents independently selected from the group consisting of halo, alkyl, haloalkyl, cycloalkyl, alkoxy, and —C(O)O-alkyl.

39. The method of any one of embodiments 1 to 38, wherein the imine of formula (C-1) or (C-2) is reacted with the reducing agent in the presence of the catalyst, and further in the presence of one or more catalyst promoters to produce the alkylfuran of formula (I), wherein the one or more catalyst promoters reduce the amount of ring saturation products that form.

40. The method of embodiment 39, wherein the one or more catalyst promoters are selected from the group consisting of sulfur, pyridine, lithium chloride (LiCl), lithium bromide (LiBr), dimethylamine, triethylamine, diisopropylamine, tertbutylamine, hydrochloric acid (HCl), and sulfuric acid ($H_2SO_4$), or any combination thereof.

41. The method of any one of embodiments 1 to 40, wherein the yield of alkylfuran of formula (I) produced is at least 50%.

42. A method for preparing an alkylfuran of formula (I):

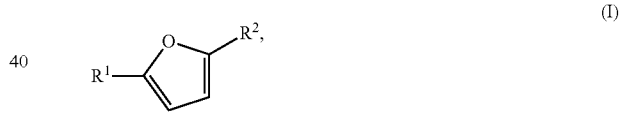

wherein $R^1$ is H or $C_x$ alkyl, wherein x is an integer equal to or greater than 1;
wherein $R^2$ is $C_y$ alkyl, wherein y is an integer equal to or greater than 1; and
wherein the method comprises: reducing an imine of formula (C-3) to produce the alkylfuran of formula (I), wherein the imine of formula (C-3) is:

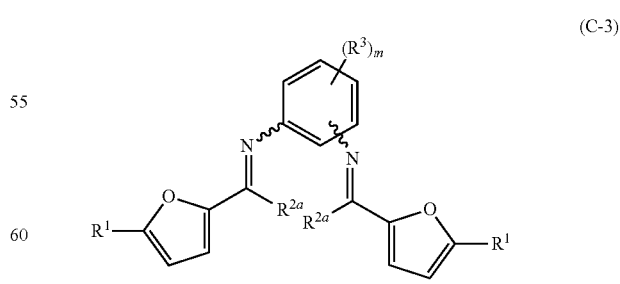

wherein:
$R^1$ is as defined in formula (I);
$R^{2a}$ is H or $C_{y-1}$ alkyl, wherein y is as defined in formula (I), provided that $R^{2a}$ is H when y is 1;
m is 0, 1, 2, 3 or 4; and each $R^3$ is independently halo, alkyl, haloalkyl, cycloalkyl, alkoxy, or —C(O)O-alkyl.

43. A method for preparing an alkylfuran of formula (I):

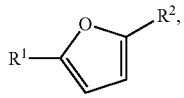
(I)

wherein $R^1$ is H or $C_x$ alkyl, wherein x is an integer equal to or greater than 1;

wherein $R^2$ is $C_y$ alkyl, wherein y is an integer equal to or greater than 1; and wherein the method comprises:

a) providing an imine of formula (C-3):

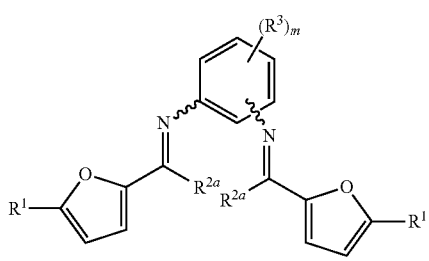
(C-3)

wherein:
$R^1$ is as defined in formula (I);
$R^{2a}$ is H or $C_{y-1}$ alkyl, wherein y is as defined in formula (I), provided that $R^{2a}$ is H when y is 1;
m is 0, 1, 2, 3 or 4; and
each $R^3$ is independently halo, alkyl, haloalkyl, cycloalkyl, alkoxy, or —C(O)O-alkyl; and b) reacting the imine of formula (C-3) with a reducing agent in the presence of catalyst to produce the alkylfuran of formula (I).

44. The method of embodiment 42 or 43, wherein $R^1$ is H.
45. The method of embodiment 43 or 43, wherein $R^1$ is $C_x$ alkyl.
46. The method of embodiment 45, wherein x is 1, 2, 3, 4, 5, 6, 7, 8, 9 or 10.
47. The method of any one of embodiments 42 to 45, wherein y is 1, 2, 3, 4, 5, 6, 7, 8, 9 or 10.
48. The method of embodiment 42 or 43, wherein $R^1$ is H, and $R^2$ is methyl.
49. The method of embodiment 42 or 43, wherein $R^1$ and $R^2$ are both methyl.
50. The method of any one of embodiments 42 to 49, wherein m is 0, 1, 2, 3, or 4.
51. The method of embodiment 50, wherein m is 0.
52. The method of embodiment 50, wherein m is 1 or 2.
53. The method of any one of embodiments 42 to 52, wherein each $R^3$ is independently chloro, fluoro, methyl, ethyl, propyl, butyl, —CF$_3$, —CHF$_2$, —CH$_2$F, methoxy, ethoxy, propoxy, butoxy, —CO$_2$-methyl, —CO$_2$-ethyl, —CO$_2$-propyl, or —CO$_2$-butyl.
54. The method of embodiment 42, wherein the imine of formula (C-3) is

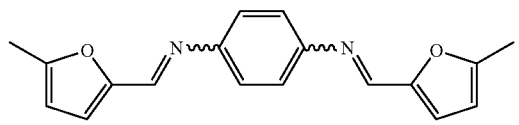

55. The method of any one of embodiments 43 to 54, wherein the catalyst is a palladium catalyst.
56. The method of embodiment 55, wherein the catalyst is palladium on carbon.
57. The method of any one of embodiments 43 to 56, wherein the imine of formula (C-3) is reacted with the hydrogen in the presence of the catalyst, and further in the presence of a solvent.
58. The method of embodiment 57, wherein the solvent has a pKa between 2 to 6.5.
59. The method of any one of embodiments 43 to 58, wherein the reducing agent is hydrogen or transfer hydrogenation.
60. The method of any one of embodiments 43 to 58, wherein the reducing agent is cyclohexene or formic acid.
61. The method of any one of embodiments 53 to 59, wherein the imine of formula (C-3) is provided by:

i) providing a compound of formula (A-1):

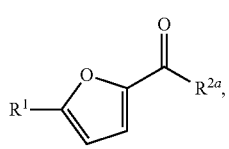
(A-1)

wherein:
$R^1$ is as defined in formula (I);
$R^{1a}$ and $R^{2a}$ are each as defined in formula (C-3); ad
ii) providing a diaminobenzene of formula (B-1) to provide the imine of formula (C-3),

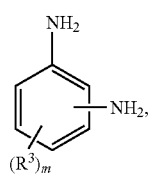
(B-1)

wherein:
m and $R^3$ are as defined in formula (C-3); and
iii) reacting the compound of formula (A-1) with the diaminobenzene of formula (B-1) to provide the imine of formula (C-3).

62. The method of embodiment 61, wherein the diaminobenzene of formula (B-1) is

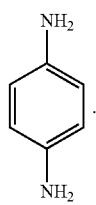

63. The method of embodiment 61 or 62, wherein the compound of formula (A-1) is reacted with the diaminobenzene of formula (B-1) at a temperature of at least 40° C.

64. The method of embodiment 42, wherein:
the alkylfuran of formula (I) is:

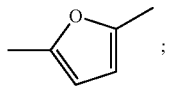
;

and
the imine of formula (C-3) is:

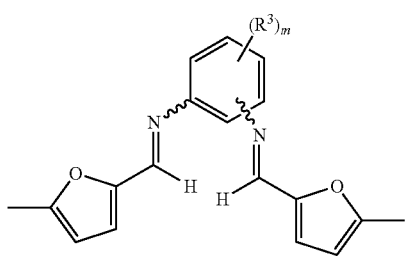

65. The method of any one of embodiments 42 to 65, wherein the imine of formula (C-3) is reacted with the reducing agent in the presence of the catalyst, and further in the presence of one or more catalyst promoters to produce the alkylfuran of formula (I), wherein the one or more catalyst promoters reduce the amount of ring saturation products that form.

66. The method of embodiment 63, wherein the one or more catalyst promoters are selected from the group consisting of sulfur, pyridine, lithium chloride (LiCl), lithium bromide (LiBr), dimethylamine, triethylamine, diisopropylamine, tertbutylamine, hydrochloric acid (HCl), and sulfuric acid ($H_2SO_4$), or any combination thereof.

67. The method of any one of embodiments 42 to 66, wherein the yield of alkylfuran of formula (I) produced is at least 50%.

68. A method for preparing a mixture of alkylfurans, wherein the mixture comprises an alkylfuran of formula (I') and an alkylfuran of formula (I"):

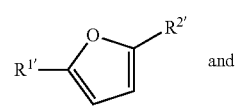
and

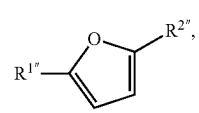
, wherein each $R^{1'}$ and $R^{1''}$ is independently H or $C_x$ alkyl, wherein x at each occurrence is independently an integer equal to or greater than 1;
wherein each $R^{2'}$ and $R^{2''}$ is independently $C_y$ alkyl, wherein y at each occurrence is independently an integer equal to or greater than 1; and
wherein the method comprises: reducing an imine of formula (C-4) to produce the mixture of alkylfurans, wherein the imine of formula (C-4) is:

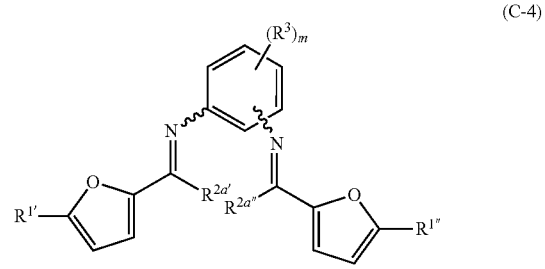

wherein:
$R^{1'}$ is as defined in formula (I');
$R^{2'}$, is as defined in formula (I");
$R^{2a'}$ is H or $C_{y-1}$ alkyl, wherein y is as defined in formula (I'), provided that $R^{2a'}$ is H when y is 1;
$R^{2a'''}$ is H or $C_{y-1}$ alkyl, wherein y is as defined in formula (I"), provided that $R^{2a''}$ is H when y is 1;
m is 0, 1, 2, 3 or 4; and
each $R^3$ is independently halo, alkyl, haloalkyl, cycloalkyl, alkoxy, or —C(O)O-alkyl.

69. A method for preparing a mixture of alkylfurans, wherein the mixture comprises an alkylfuran of formula (I') and an alkylfuran of formula (I"):

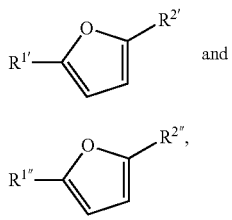
and (I")

wherein each $R^{1'}$ and $R^{1''}$ is independently H or $C_x$ alkyl, wherein x at each occurrence is independently an integer equal to or greater than 1;
wherein each $R^{2'}$ and $R^{2''}$ is independently $C_y$ alkyl, wherein y at each occurrence is independently an integer equal to or greater than 1; and
wherein the method comprises:
a) providing an imine of formula (C-4):

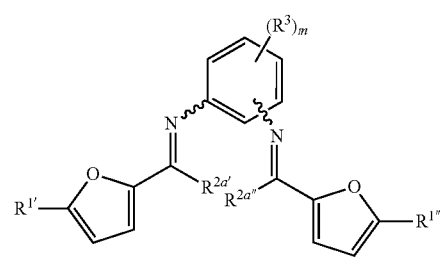

wherein:
$R^{1'}$ is as defined in formula (I');
$R^{2'}$, is as defined in formula (I");
$R^{2a'}$ is H or $C_{y-1}$ alkyl, wherein y is as defined in formula (I'), provided that $R^{2a'}$ is H when y is 1;

$R^{2a''}$ is H or $C_{y-1}$ alkyl, wherein y is as defined in formula (I″), provided that $R^{2a''}$ is H when y is 1;
m is 0, 1, 2, 3 or 4; and
each $R^3$ is independently halo, alkyl, haloalkyl, cycloalkyl, alkoxy, or —C(O)O-alkyl; and
b) reacting the imine of formula (C-4) with a reducing agent in the presence of catalyst to produce the mixture of alkylfurans.

70. The method of embodiment 68 or 69, wherein $R^{1'}$ is H, and $R^{1''}$ is $C_x$ alkyl.

71. The method of embodiment 68 or 69, wherein each $R^{1'}$ and $R^{1''}$ are independently $C_x$ alkyl.

72. The method of any one of embodiments 68 to 71, wherein x is 1, 2, 3, 4, 5, 6, 7, 8, 9 or 10.

73. The method of any one of embodiments 68 to 72, wherein y is 1, 2, 3, 4, 5, 6, 7, 8, 9 or 10.

74. The method of any one of embodiments 68 to 73, wherein m is 0, 1, 2, 3, or 4.

75. The method of embodiment 74, wherein m is 0.

76. The method of embodiment 74, wherein m is 1 or 2.

77. The method of any one of embodiments 68 to 76, wherein each $R^3$ is independently chloro, fluoro, methyl, ethyl, propyl, butyl, —CF$_3$, —CHF$_2$, —CH$_2$F, methoxy, ethoxy, propoxy, butoxy, —CO$_2$-methyl, —CO$_2$-ethyl, —CO$_2$-propyl, or —CO$_2$-butyl.

78. The method of any one of embodiments 69 to 77, wherein the catalyst is a palladium catalyst.

79. The method of embodiment 78, wherein the catalyst is palladium on carbon.

80. The method of any one of embodiments 69 to 79, wherein the imine of formula (C-4) is reacted with the hydrogen in the presence of the catalyst, and further in the presence of a solvent.

81. The method of embodiment 80, wherein the solvent has a pKa between 2 to 6.5.

82. The method of any one of embodiments 69 to 81, wherein the reducing agent is hydrogen or transfer hydrogenation.

83. The method of any one of embodiments 69 to 81, wherein the reducing agent is cyclohexene or formic acid.

84. The method of any one of embodiments 69 to 83, wherein the imine of formula (C-4) is provided by:
i) providing a mixture of compounds comprising a compound of formula (A-1') and a compound of formula (A-1″):

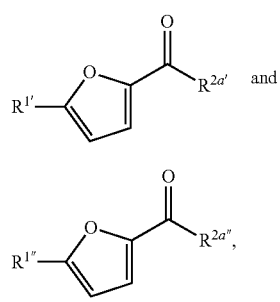

wherein:
$R^{1'}$ and $R^{2a'}$ are as defined in formula (I'); and
$R^{1''}$ and $R^{2a''}$ are as defined in formula (I″);
ii) providing a diaminobenzene of formula (B-1) to provide the imine of formula (C-3),

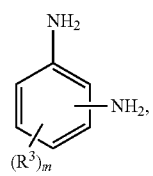

wherein:
m and $R^3$ are as defined in formula (C-4); and
iii) reacting the compound of formula (A-1) with the diaminobenzene of formula (B-1) to provide the imine of formula (C-4).

85. The method of embodiment 84, wherein the diaminobenzene of formula (B-1) is

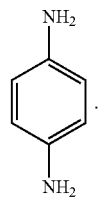

86. The method of embodiment 84 or 85, wherein the compound of formula (A-1) is reacted with the diaminobenzene of formula (B-1) at a temperature of at least 40° C.

87. The method of any one of embodiments 69 to 86, wherein the imine of formula (C-4) is reacted with the reducing agent in the presence of the catalyst, and further in the presence of one or more catalyst promoters to produce the alkylfuran of formula (I), wherein the one or more catalyst promoters reduce the amount of ring saturation products that form.

88. The method of embodiment 87, wherein the one or more catalyst promoters are selected from the group consisting of sulfur, pyridine, lithium chloride (LiCl), lithium bromide (LiBr), dimethylamine, triethylamine, diisopropylamine, tertbutylamine, hydrochloric acid (HCl), and sulfuric acid (H$_2$SO$_4$), or any combination thereof.

89. The method of any one of embodiments 68 to 88, wherein the yield of alkylfuran of formula (I) produced is at least 50%.

90. A composition comprising:
an imine of formula (C-1), (C-2), (C-3) or (C-4):

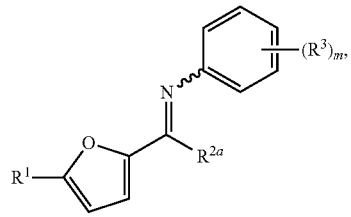

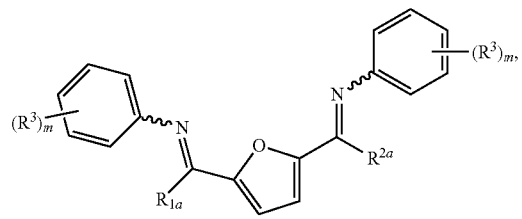

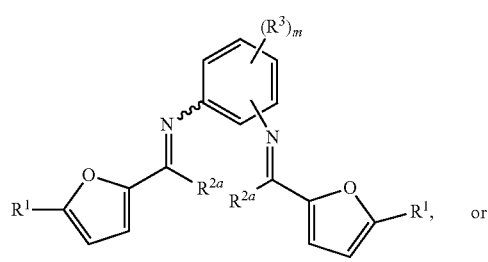

-continued

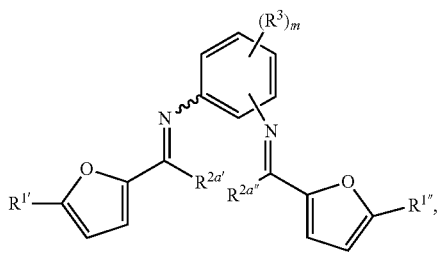
(C-4)

wherein:
$R^1$, $R^{1'}$ and $R^{1''}$ (if present) is H or $C_x$ alkyl, wherein x is an integer equal to or greater than 1;
$R^{1a}$ (if present) is H or $C_{x-1}$ alkyl, provided that $R^{1a}$ is H when x is 1;
$R^{2a}$, $R^{2a'}$ and $R^{2a''}$ (if present) is H or $C_{y-1}$ alkyl, wherein y is an integer equal to or greater than 1, provided that $R^{2a}$ is H when y is 1;
m is 0, 1, 2, 3, 4 or 5; and
each $R^3$ is independently halo, alkyl, haloalkyl, cycloalkyl, alkoxy, or —C(O)O-alkyl;
a reducing agent; and
catalyst.

91. The composition of embodiment 90, wherein $R^1$, $R^{1'}$ and $R^{1''}$ (if present) is H.
92. The composition of embodiment 90, wherein $R^1$, $R^{1'}$ and $R^{1''}$ (if present) is $C_x$ alkyl.
93. The composition of any one of embodiments 90 to 92, wherein x is 1, 2, 3, 4, 5, 6, 7, 8, 9 or 10.
94. The composition of any one of embodiments 90 to 93, wherein y is 1, 2, 3, 4, 5, 6, 7, 8, 9 or 10.
95. The composition of any one of embodiments 90 to 94, wherein m is 0.
96. The composition of any one of embodiments 90 to 94, wherein m is 1 or 2.
97. The composition of any one of embodiments 90 to 96, wherein each $R^3$ is independently chloro, fluoro, methyl, ethyl, propyl, butyl, —$CF_3$, —$CHF_2$, —$CH_2F$, methoxy, ethoxy, propoxy, butoxy, —$CO_2$-methyl, —$CO_2$-ethyl, —$CO_2$-propyl, or —$CO_2$-butyl.
98. The composition of any one of embodiments 90 to 93, wherein the imine of formula (C-1) is selected from the group consisting of:

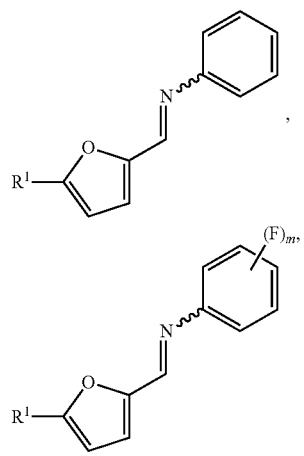
,

-continued

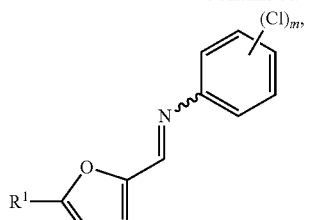

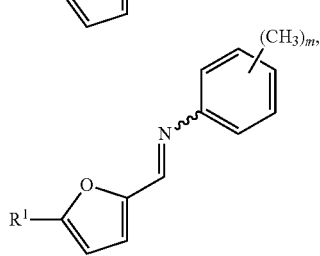

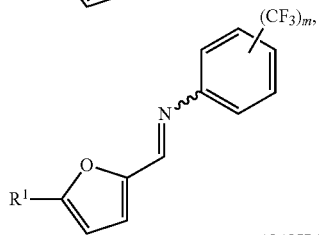

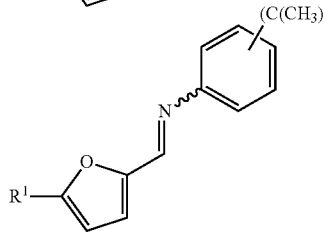

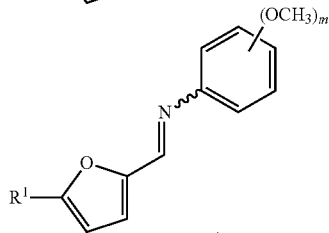

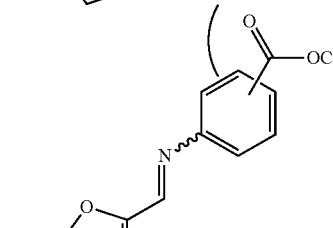

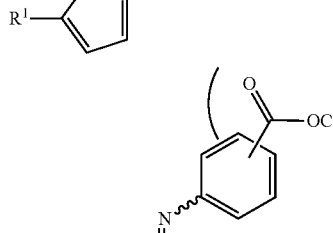
, and

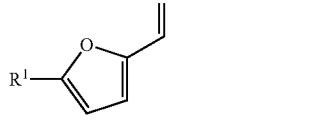
.

99. The composition of any one of embodiments 90 to 93, wherein the imine of formula (C-1) is selected from the group consisting of:
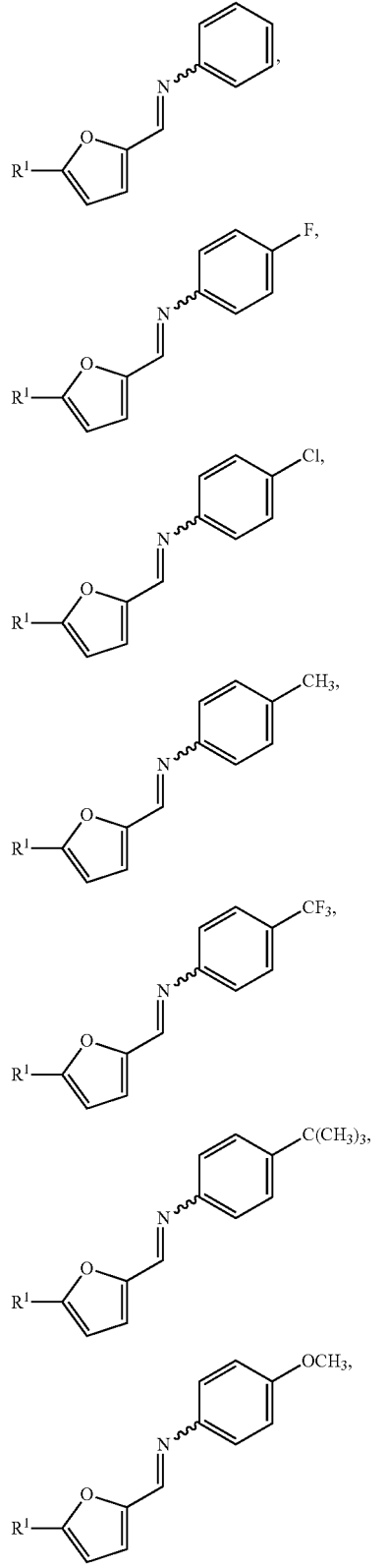
-continued
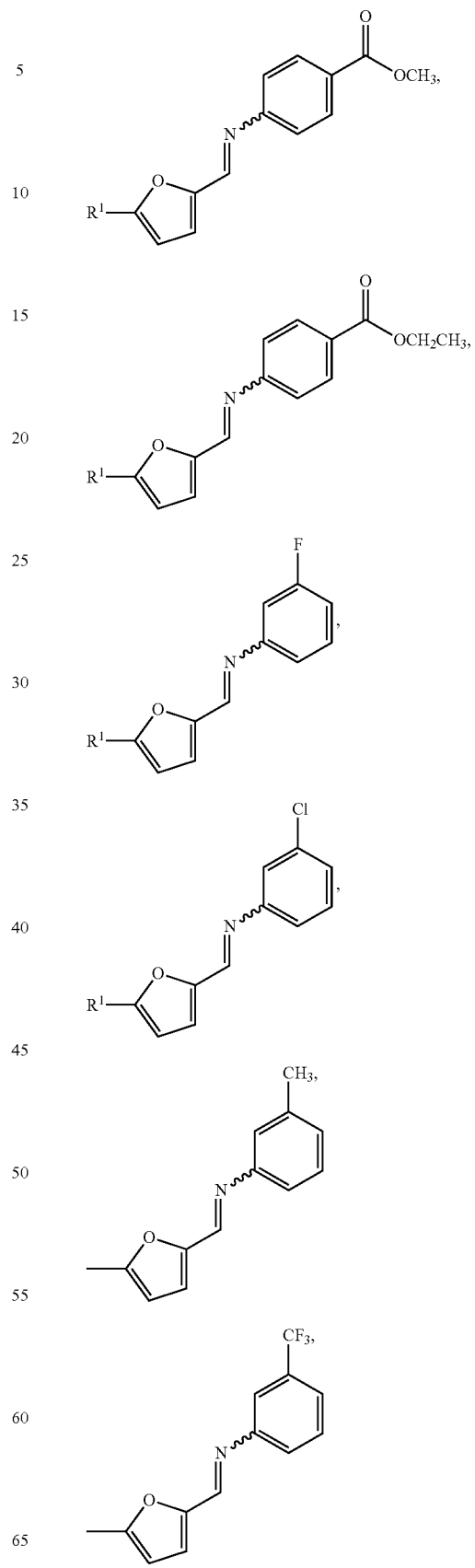

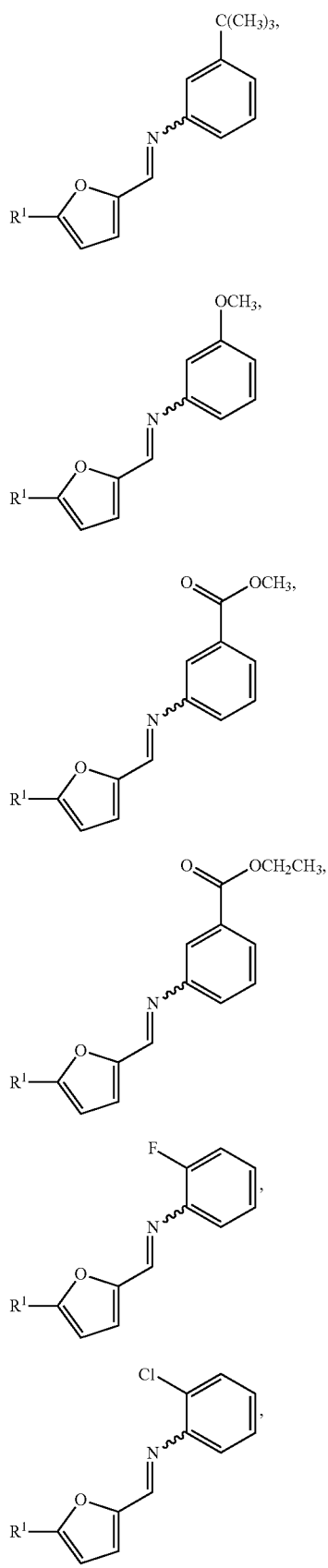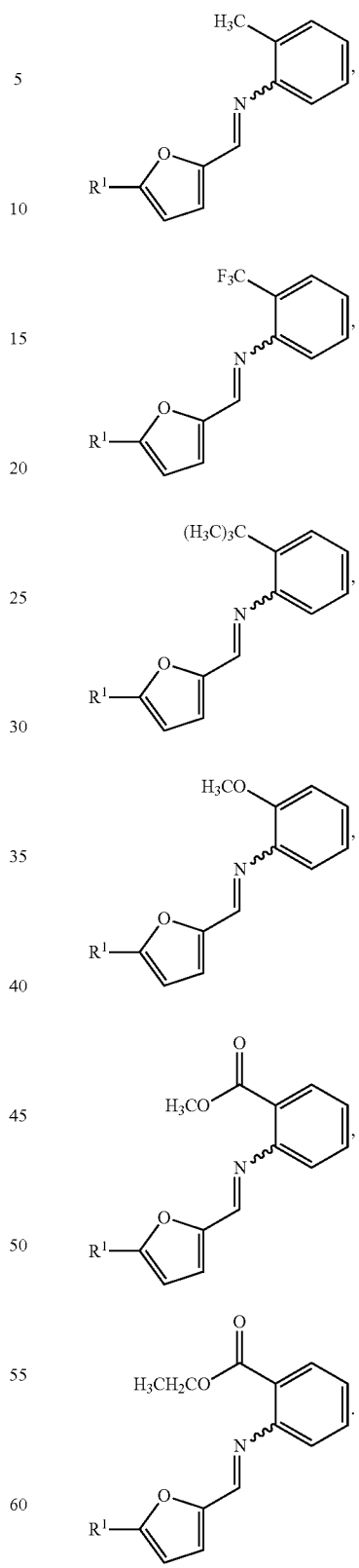
100. The composition of any one of embodiments 90 to 93, wherein the imine of formula (C-2) is selected from the group consisting of:

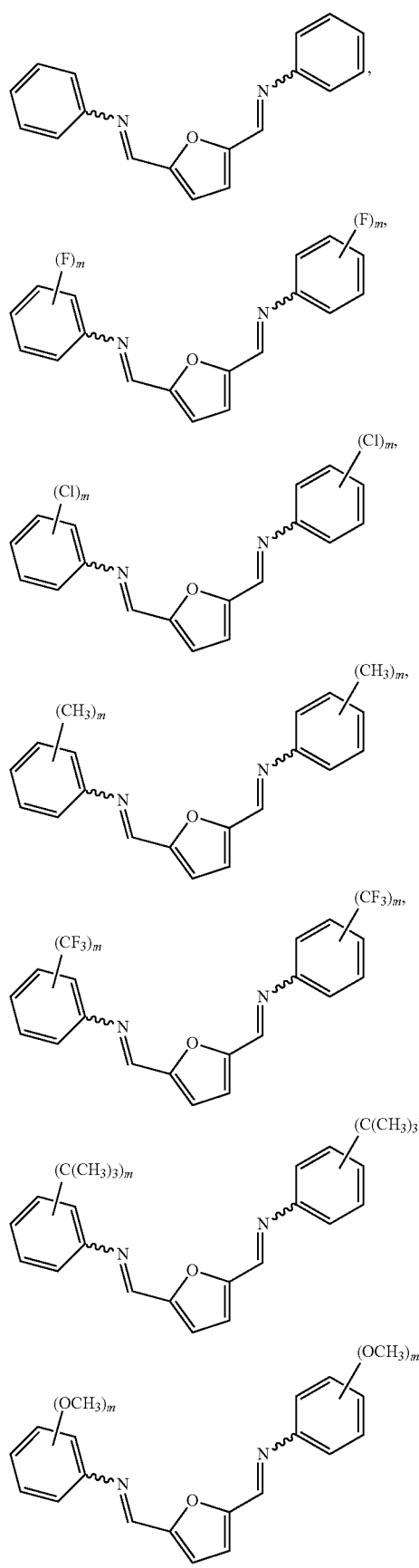
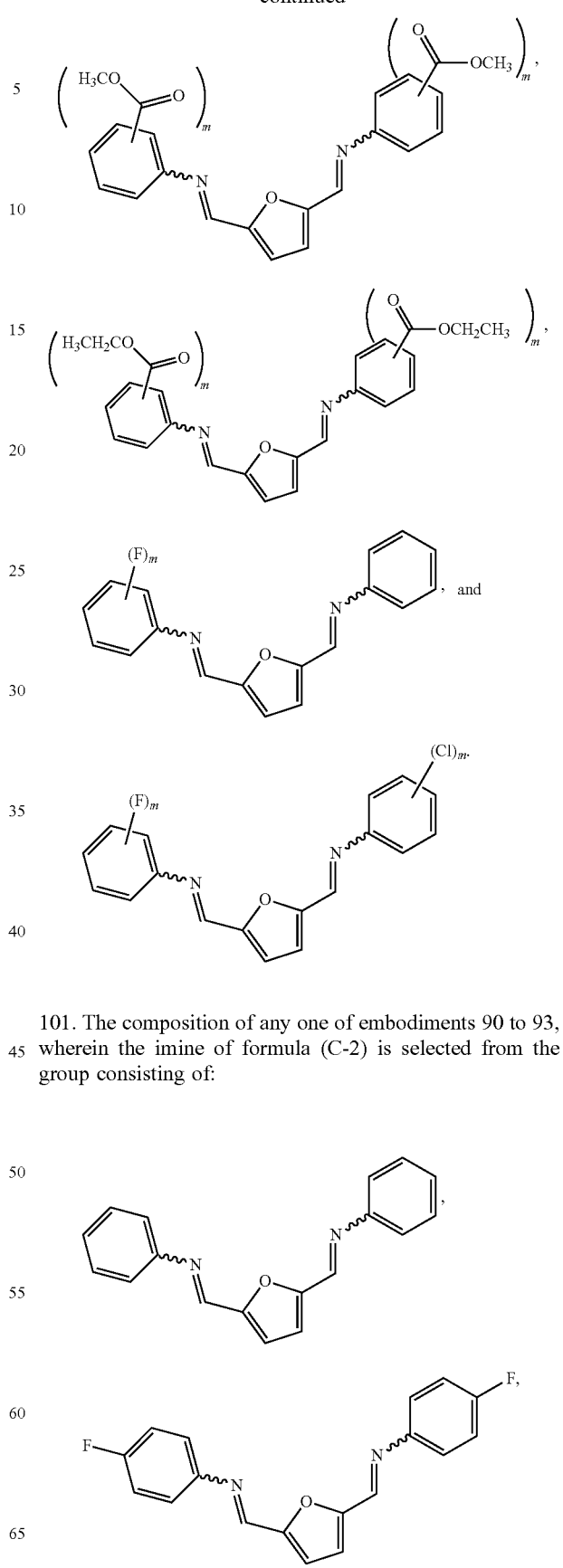
101. The composition of any one of embodiments 90 to 93, wherein the imine of formula (C-2) is selected from the group consisting of:

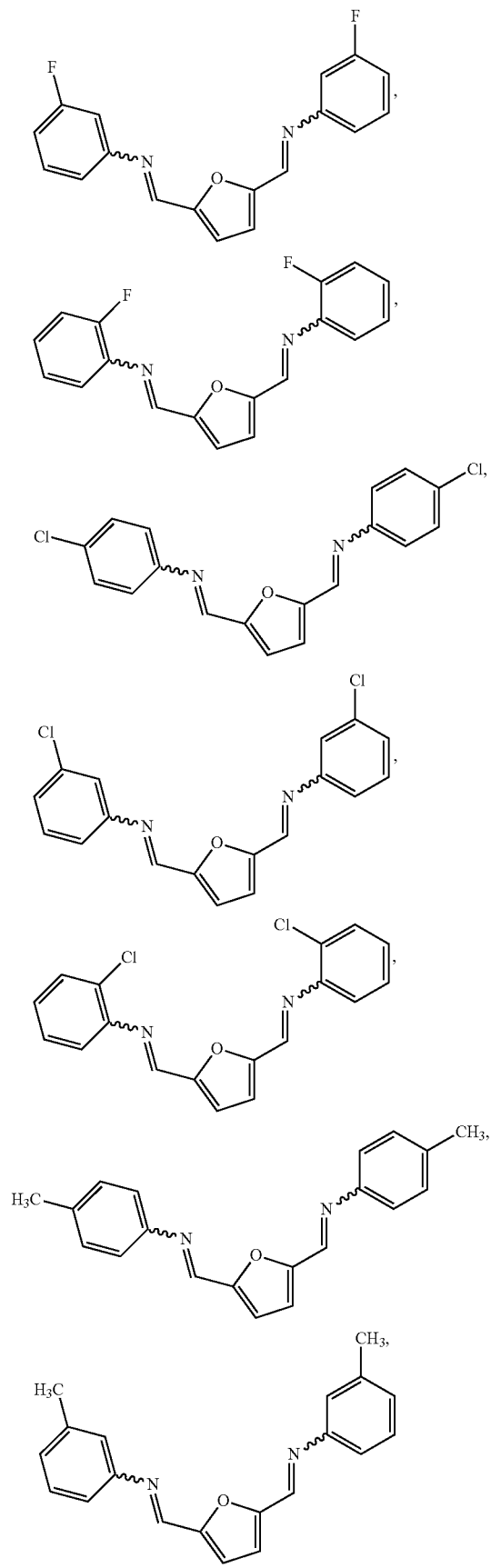
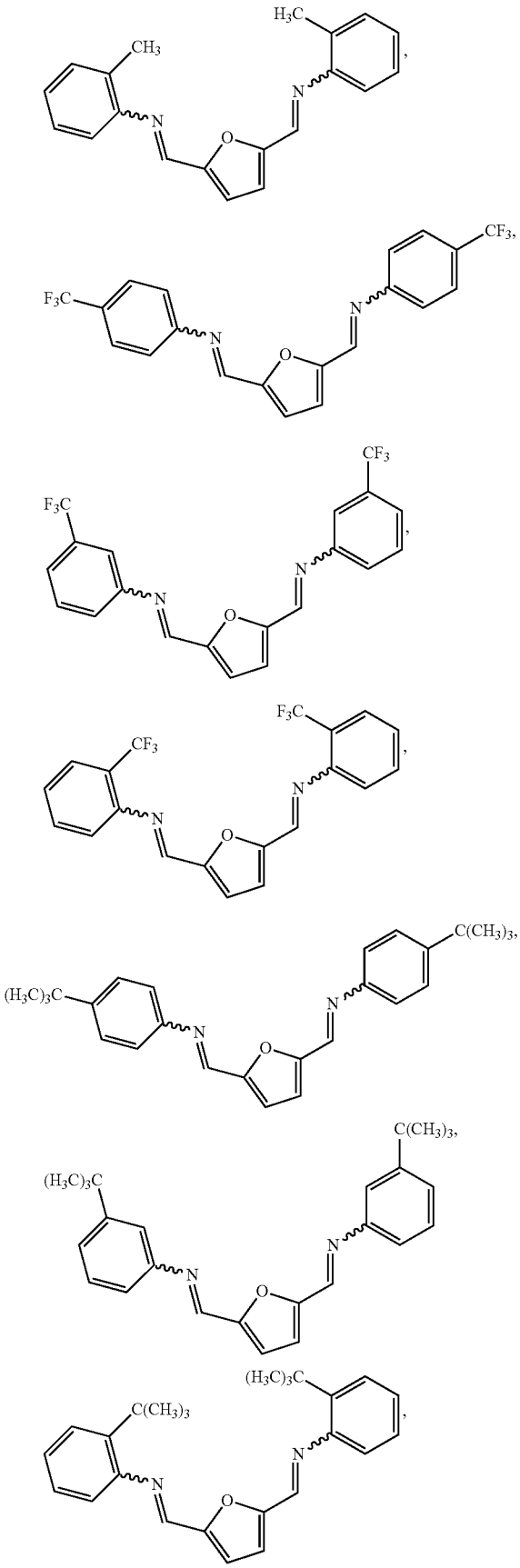

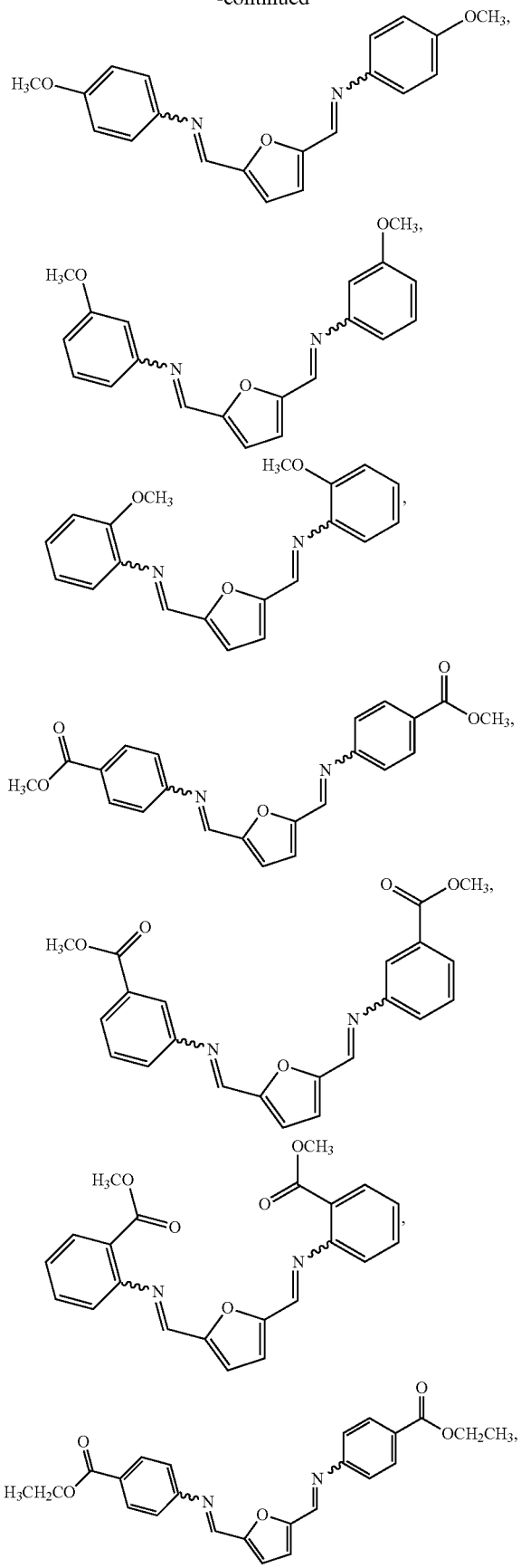

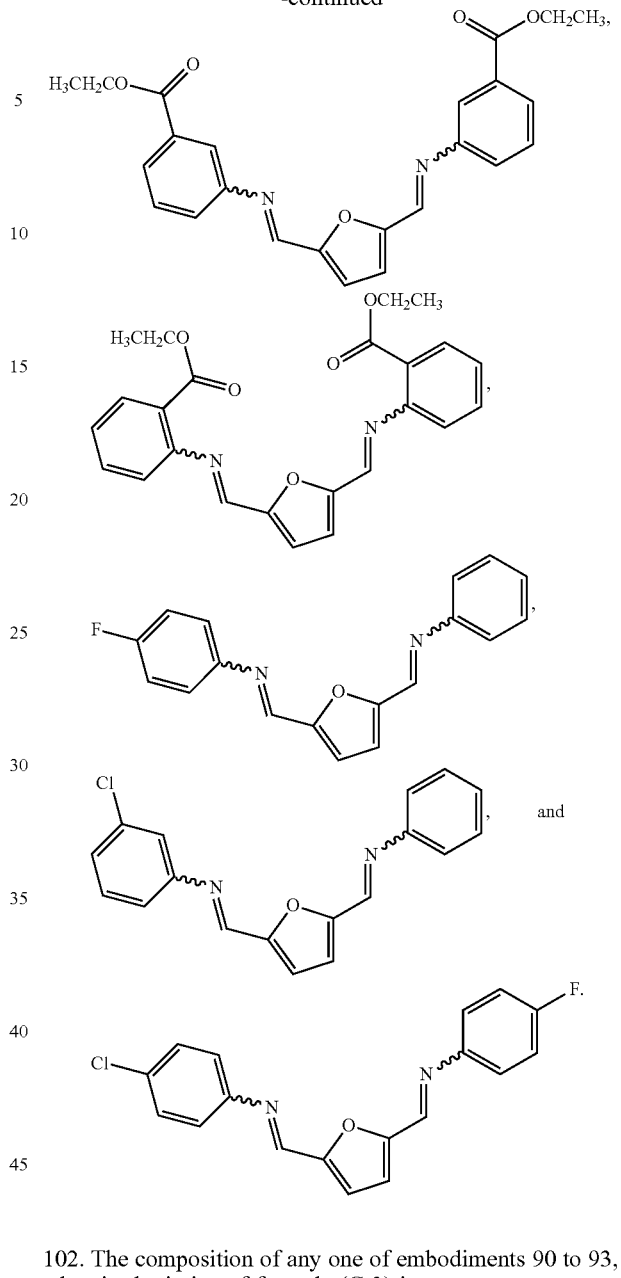

102. The composition of any one of embodiments 90 to 93, wherein the imine of formula (C-3) is

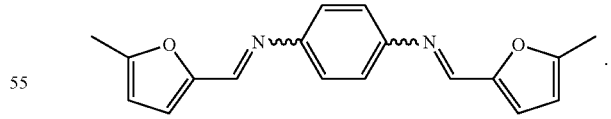

103. The composition of any one of embodiments 90 to 102, wherein the reducing agent is hydrogen or transfer hydrogenation.

104. The composition of any one of embodiments 90 to 102, wherein the reducing agent is cyclohexene or formic acid.

105. The composition of any one of embodiments 90 to 104, wherein the catalyst is palladium catalyst, platinum catalyst, ruthenium catalyst, copper catalyst, or any combinations thereof.

106. The composition of any one of embodiments 90 to 104, wherein the catalyst is palladium on carbon.
107. The composition of any one of embodiments 90 to 106, further comprising one or more alkylfurans of formula (I):

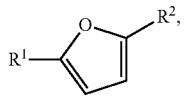

(I)

wherein:
R$^1$ is H or C$_x$ alkyl, wherein x is an integer equal to or greater than 1;
R$^2$ is C$_y$ alkyl, wherein y is an integer equal to or greater than 1.
108. The composition of embodiment 107, wherein the one or more alkylfurans are:

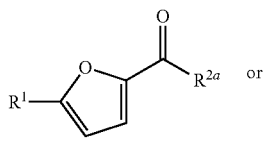

or both.
109. A composition comprising:
a compound of formula (A-1) or (A-2):

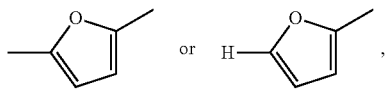

(A-1)

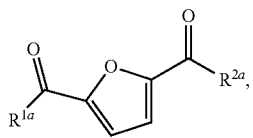

(A-2)

wherein:
R$^1$ is H or C$_x$ alkyl, wherein x is an integer equal to or greater than 1;
R$^{1a}$ is H or C$_{x-1}$ alkyl, provided that R$^{1a}$ is H when x is 1;
R$^{2a}$ is H or C$_{y-1}$ alkyl, wherein y is an integer equal to or greater than 1, provided that R$^{2a}$ is H when y is 1; and
an aniline of formula (B):

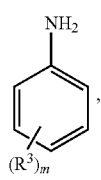

(B)

wherein:
m is 0, 1, 2, 3, 4 or 5; and
each R$^3$ is independently halo, alkyl, haloalkyl, cycloalkyl, alkoxy, or —C(O)O-alkyl.

110. The composition of embodiment 88, wherein the aniline of formula (B) is:

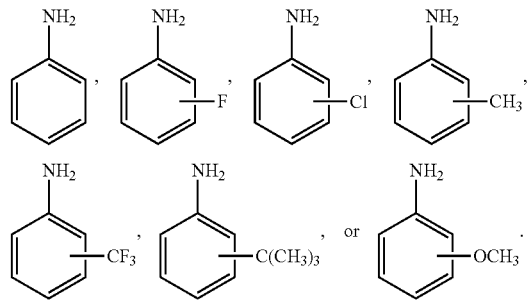

111. The composition of embodiment 88, wherein the aniline of formula (B):

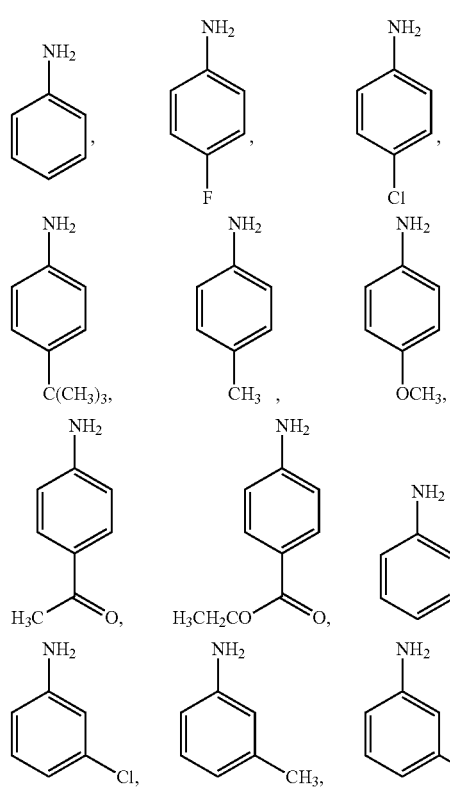

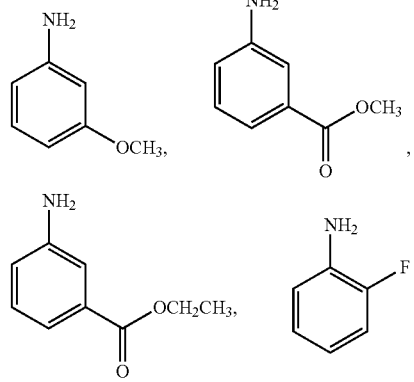

87

-continued

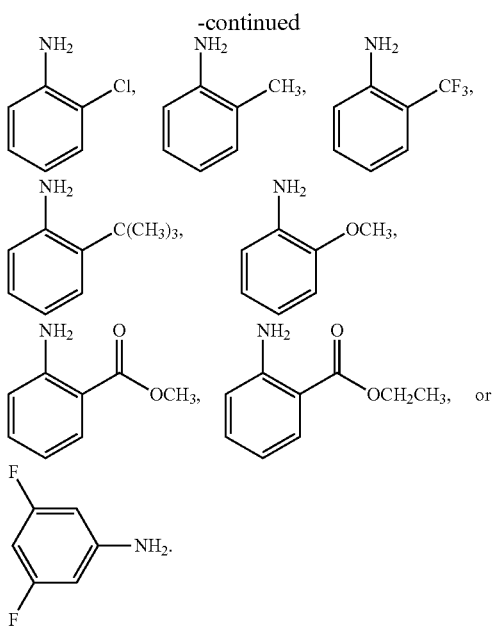

112. The composition of any one of embodiments 88 to 90, further comprising a solvent.
113. The composition of embodiment 91, wherein the solvent has a pKa between 2 to 6.5.
114. The composition of any one of embodiments 88 to 92, further comprising an imine of formula (C-1) or (C-2):

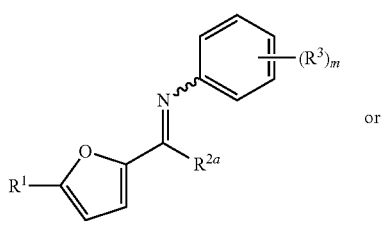
(C-1)

or

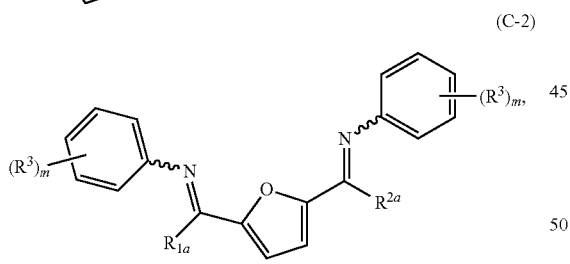
(C-2)

wherein:
R$^1$ is as defined in formula (A-1) or (A-2);
R$^{1a}$ is H or C$_{x-1}$ alkyl, wherein x is as defined in formula (A-1) or (A-2), provided that R$^{1a}$ is H when x is 1;
R$^{2a}$ is H or C$_{y-1}$ alkyl, wherein y is as defined in formula (A-1) or (A-2), provided that R$^{2a}$ is H when y is 1;
m and R$^3$ are as defined in formula (B).
115. The composition of any one of embodiments 88 to 93, further comprising an additional reagent suitable to reduce the formation of one or more ring saturation products.
116. The composition of embodiment 94, wherein the additional reagent is sulfur, pyridine, lithium chloride (LiCl), lithium bromide (LiBr), dimethylamine, triethylamine, diisopropylamine, tertbutylamine, hydrochloric acid (HCl), or sulfuric acid (H$_2$SO$_4$), or any combination thereof.

88

117. A composition comprising:
one or more compounds of formula (A-1) independently having the structure of formula (A-1):

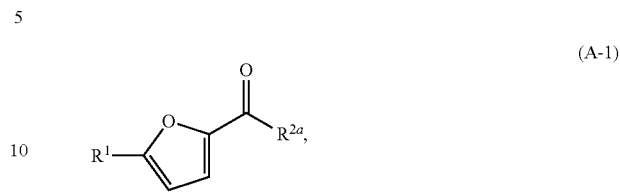
(A-1)

wherein:
R$^1$ is H or C$_x$ alkyl, wherein x is an integer equal to or greater than 1;
R$^{1a}$ is H or C$_{x-1}$ alkyl, provided that R$^{1a}$ is H when x is 1;
R$^{2a}$ is H or C$_{y-1}$ alkyl, wherein y is an integer equal to or greater than 1, provided that R$^{2a}$ is H when y is 1; and
a diaminobenzene of formula (B-1) is:

(B-1)

wherein:
m is 0, 1, 2, 3 or 4; and
each R$^3$ is independently halo, alkyl, haloalkyl, cycloalkyl, alkoxy, or —C(O)O-alkyl.
118. The composition of embodiment 117, wherein the diaminobenzene of formula (B-1) is

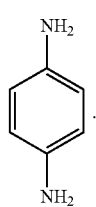

119. The composition of embodiment 117 or 118, further comprising an imine of formula (C-3) or an imine of formula (C-4):

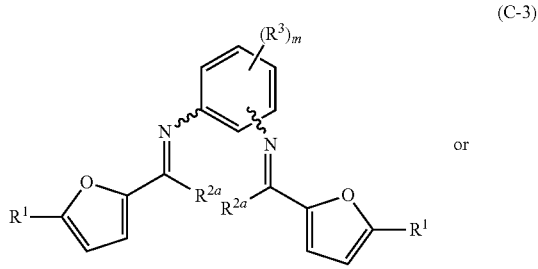
(C-3)

or

89
-continued

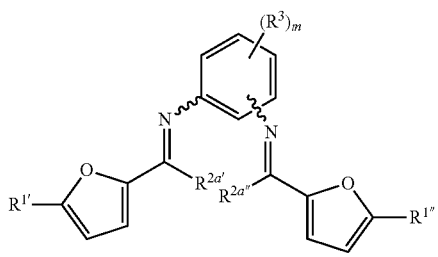

(C-4)

wherein:

R$^1$ and R$^{2a}$ of formula (C-3) are as defined for formula (A-1);

R$^{1'}$, R$^{1''}$, R$^{2a'}$ and R$^{2a''}$ of formula (C-4) are as defined for formula (A-1); and m and R$^3$ are as defined for formula (B-1).

120. The composition of any one of embodiments 117 to 119, wherein R$^1$ is H.

121. The composition of any one of embodiments 117 to 119, wherein R$^1$ is C$_x$ alkyl.

122. The composition of any one of embodiments 117 to 119, wherein x is 1, 2, 3, 4, 5, 6, 7, 8, 9 or 10.

123. The composition of any one of embodiments 117 to 122, wherein y is 1, 2, 3, 4, 5, 6, 7, 8, 9 or 10.

124. The composition of any one of embodiments 117 to 123, wherein m is 0.

125. The composition of any one of embodiments 117 to 123, wherein m is 1 or 2.

126. The composition of any one of embodiments 117 to 125, wherein each R$^3$ is independently chloro, fluoro, methyl, ethyl, propyl, butyl, —CF$_3$, —CHF$_2$, —CH$_2$F, methoxy, ethoxy, propoxy, butoxy, —CO$_2$-methyl, —CO$_2$-ethyl, —CO$_2$-propyl, or —CO$_2$-butyl.

EXAMPLES

The following Examples are merely illustrative and are not meant to limit any aspects of the present disclosure in any way.

90
Example 1

Synthesis of 2,5-Dimethylfuran from 5-Methylfurfural Using Various Aniline Compounds

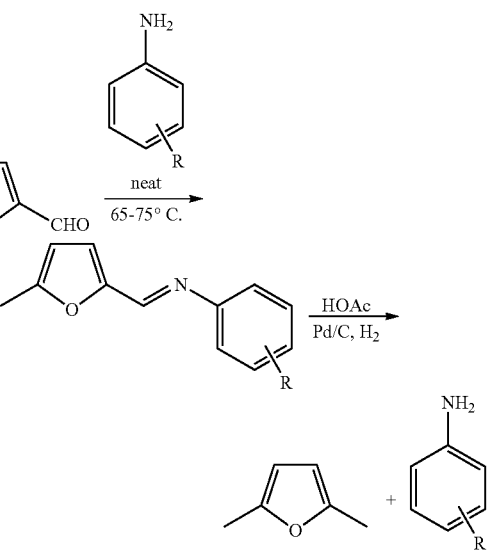

For each aniline compound listed in Table 1 below, the following reaction was performed. 5-Methylfurfural (about 0.25-0.26 g) and 1.1 equivalents of the aniline compound were combined in a vial equipped with a magnetic stirrer. The vial was sealed and purged with argon for 5 min. The vial was placed on a pre-heated oil-bath (72° C.) for 43 minutes, then cooled down to room temperature and opened.

The imine formed was dissolved in 10 mL glacial acetic acid and transferred into a 500 mL glass vessel. Palladium catalyst (10%) was added to the observed orange-red solution. The mixture was hydrogenated in a Parr shaker hydrogenator at 15 psig hydrogen pressure after purging four times with hydrogen. After about 20-30 minutes of reaction, the hydrogenator was stopped and hydrogen was vented. The reaction mixture was diluted by dichloromethane and transferred into a 250 mL volumetric flask and filled up to the mark.

A sample of the reaction mixture was analyzed by $^1$H NMR and GC analysis to determine the yield of the imine and 2,5-dimethylfuran. The yields for the reactions performed are summarized in Table 1 below.

TABLE 1

Aniline compounds used and corresponding yield of imine and 2,5-dimethylfuran

| Aniline Compound | Imine Formation (% conversion) | DMF Formation (% yield) |
|---|---|---|
| (aniline) | (imine structure) | 50 |
| | (100) | |

TABLE 1-continued
Aniline compounds used and corresponding yield of imine and 2,5-dimethylfuran
| Aniline Compound | Imine Formation (% conversion) | DMF Formation (% yield) |
|---|---|---|
| 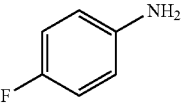 | 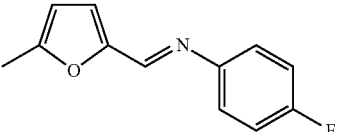 (100) | 70 |
| 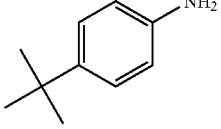 | 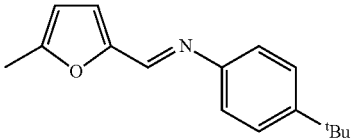 (100) | 72 |
| 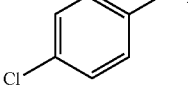 | 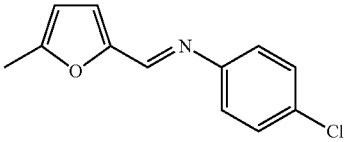 (100) | ND |
| 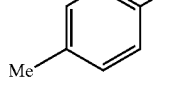 | 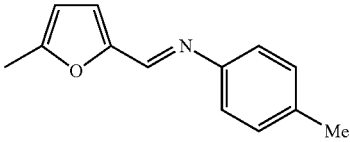 (100) | ND |
| 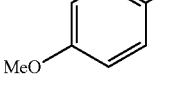 | 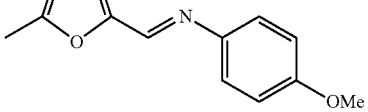 (100) | ND |
|  | 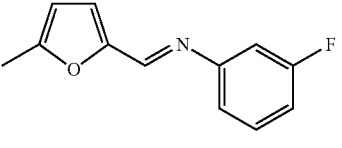 (95) | 68% |
| 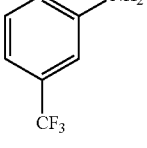 | 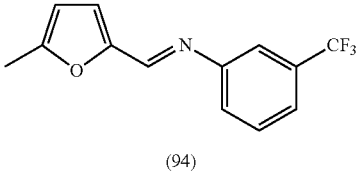 [SMILES: Cc1ccc(/C=N/c2cccc(C(F)(F)F)c2)o1] (94) | ND |
| 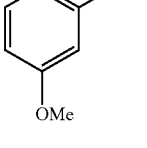 | 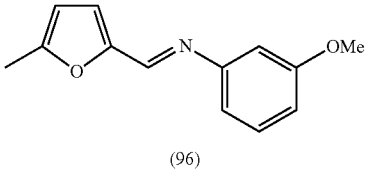 [SMILES: COc1cccc(/N=C/c2ccc(C)o2)c1] (96) | 35 |

TABLE 1-continued

Aniline compounds used and corresponding yield of imine and 2,5-dimethylfuran

| Aniline Compound | Imine Formation (% conversion) | DMF Formation (% yield) |
|---|---|---|
| 2-fluoroaniline | 5-methyl-furfurylidene-(2-fluorophenyl)imine (80) | ND |
| 2-methoxyaniline | 5-methyl-furfurylidene-(2-methoxyphenyl)imine 75% | ND |

ND refers to "no data"

For the $^1$H NMR analysis, the percentage conversion to imine was calculated by the ratio of integrations of the corresponding peaks of imine and 5-methylfurfural.

For the GC analysis, the conversion to imine was calculated by the area of 5-methylfurfural and area of the imine

Example 2

Synthesis and Isolation of Amine from Corresponding Imine

5-Methylfurfural (0.250 g, 2.27 mmol) and aniline (0.224 g, 2.40 mmol) were measured in a 20 mL scintillation vial and a magnetic stir bar was added. The vial was placed on a pre-heated oil-bath (75° C.) and stirred for 30 min. After the reaction, the vial was cooled down to room temperature and orange liquid was dissolved in 20 mL diethyl ether and dried with sodium sulfate (excess). The ether solution was transferred to a 500 mL glass vessel and 35 mg 10% Pd/C was added. The suspension was hydrogenated in a Parr shaker hydrogenator for 40 min at 15 psig hydrogen pressure after purging four times with hydrogen gas. After the reaction, the hydrogen was released and the light yellow ether solution was filtered through a filter paper under vacuum. The solvent was evaporated at room temperature under reduced pressure to yield the corresponding imine as a yellow liquid. The purity of the amine was checked by $^1$H NMR spectra. The amount of amine obtained was 0.390 g (92% yield).

Example 3

Comparison of Effects of Temperature on Synthesis of Imine

Synthesis of imine at 45° C.: 5-Methylfurfural (0.251 g) and p-fluoroaniline (0.265 g) were measured in a 20 mL scintillation vial and a magnetic stirrer was added. The vial was capped and placed in a preheated oil bath 45° C. Samples of the reaction mixture were taken periodically, and were analyzed by $^1$H NMR. The conversion to imine was calculated by the ratio of leftover 5-methylfurfural and formed imine. From the $^1$H NMR data, the conversion after 30 minutes was observed to be about 94%. The conversion to imine after 60 minutes was observed to be about 97%. The conversion after 90 minutes was observed to be about 98%. The conversion after 120 minutes was observed to be about 98%.

Synthesis of imine at room temperature: 5-Methylfurfural (0.254 g) and p-fluoroaniline (0.276 g) were measured in a 20 mL scintillation vial and a magnetic stirrer was added. The vial was capped and placed in a preheated oil bath 45° C. Samples of the reaction mixture were taken periodically, and were analyzed by $^1$H NMR. The conversion to imine was calculated by the ratio of leftover 5-methylfurfural and formed imine. From the $^1$H NMR data, the conversion after 30 minutes was observed to be about 87%. The conversion after 60 minutes was observed to be about 92%.

Example 4

Transfer Hydrogenation of Imine Using Cyclohexene 0.155 g of the imine from the reaction of 5-methylfurfural and p-fluoroaniline was measured in a 10 mL glass pressure tube. The imine was dissolved in 5 mL cyclohexene, to which 10% Pd/C (110 mg) was added. A magnetic stirrer was added to the reaction mixture, which was then purged with argon and sealed. The reaction tube was placed in a pre-heated (105° C.) oil-bath and stirred for 60 minutes. After reaction was observed to be complete, the tube was cooled down to room temperature and opened. A sample of the reaction mixture was analyzed by $^1$H NMR, which showed reduction of imine to amine and also from amine to 2,5-dimethylfuran.

Example 5

Transfer Hydrogenation of Imine Using Formic Acid 0.160 g of the imine from the reaction of 5-methylfurfural and p-fluoroaniline was measured in a 10 mL glass pressure tube. The imine was dissolved in 5 mL formic acid, to which 10% Pd/C (120 mg) was added. A magnetic stirrer was added to the reaction mixture, which was then purged with argon and sealed. The reaction tube was placed in a pre-heated (110° C.) oil-bath and stirred for 60 minutes. After reaction was observed to be complete, the tube was cooled

Example 6

Hydrogenation of Imine in N,N-Dimethylformamide

In a 20 mL scintillation vial, 0.156 g of imine synthesized by condensing 5-methylfurfural and p-fluoroaniline was dissolved in 6 mL N,N-dimethylformamide. 34 mg 10% Pd/C was added to the observed yellow solution. The suspension was transferred to a 250 mL glass vessel used in a Parr shaker hydrogenator. The vessel was purged four times with hydrogen before pressurizing to 15 psig. The suspension was hydrogenated for 25 minutes. After the reaction was observed to be complete, the pressure was released. A sample of the reaction mixture was analyzed by $^1$H NMR. The $^1$H NMR spectrum showed observable peaks for 2,5-dimethylfuran (5.68 ppm, 2.10 ppm).

Example 7

Reaction of 5-Methylfurfural with Aniline Compounds

5-Methylfurfural (0.200 g, 1.81 mmol) and the aniline compound described in Table 2 below (1.81 mmol) were added to a 25 mL round bottomed flask fitted with a magnetic stirrer. A catalytic amount of glacial acetic acid (0.1 mL) was added to the reaction mixture. The flask was purged with argon and capped. The flask was placed in a pre-heated oil bath (75° C.) and reacted for about 45 minutes. Then, the flask was cooled down to room temperature. The cap and the walls of the flask were washed using dichloromethane. Dichloromethane was evaporated under reduced pressure to provide a crude liquid. The $^1$H NMR of the crude liquid was taken. The percentage conversion indicated in Table 2 below was determined by $^1$H NMR.

TABLE 2

Aniline compounds used and corresponding yield of imine

| No. | Aniline Compound | Imine Formation (% conversion) |
|---|---|---|
| 1 | EtO-C(O)-C$_6$H$_4$-NH$_2$ | 5-methyl-furan-CH=N-C$_6$H$_4$-C(O)OEt (70%) |
| 2 | 3,5-difluoroaniline | 3,5-difluoro-C$_6$H$_3$-N=CH-furan-5-methyl (50%) |

Example 8

Reaction of 5-Methylfurfural with Aniline and Diaminobenzyl Compounds to Form Imine Compounds, and Hydrogenation of Imine Compounds to Form 2,5-Dimethylfuran Formation of Imine:

5-Methylfurfural and the aniline compound described in Table 3 below were reacted according to the procedure set forth in Example 7 above, except that acetic acid was not used in the reactions of this Example. Additionally, in the case of benzene-1,4-diamine, toluene was used as a solvent. The percentage conversion indicated in Table 3 below was determined by $^1$H NMR.

TABLE 3

Aniline compounds used and corresponding yield of imine

| No. | Aniline | Imine Formation (% conversion) |
|---|---|---|
| 1 | 2-methylaniline (o-Me-C$_6$H$_4$-NH$_2$) | 5-methyl-furan-CH=N-C$_6$H$_4$-(o-Me) (80%) |

TABLE 3-continued

Aniline compounds used and corresponding yield of imine

| No. | Aniline | Imine Formation (% conversion) |
|---|---|---|
| 2 | 3-methylaniline (Me-C6H4-NH2) | 5-methylfurfurylidene-(3-methylphenyl)imine (100%) |
| 3 | 1,4-phenylenediamine (H2N-C6H4-NH2) | bis(5-methylfurfurylidene)-1,4-phenylenediimine (95%) |

Hydrogenation of Imine Compounds to Form DMF:

The imine formed as described in Table 3 above (0.200 g) was dissolved in 10 mL glacial acetic acid and transferred into a 250 mL glass vessel used in the Parr shaker hydrogenator. The catalyst (10% Pd/C, 20 mg) and the additional reagent described in Table 4 below were added to the hydrogenator. The use of such additional reagent was explored in this Example in order to determine whether the ring saturation product, which may form as a product by palladium-catalyzed hydrogenation of an imine compound, could be minimized or eliminated.

The hydrogenator was purged with hydrogen three times before pressurizing at 15 psig. The reaction was hydrogenated for 35 min. Then, the hydrogen pressure was released, and a sample of the crude reaction mixture was analyzed by $^1$H NMR, in part to check for formation of DMF. The volatiles in the crude reaction mixture were removed under vacuum, and a sample of the resulting mixture was analyzed by $^1$H NMR, in part to identify the presence of a ring saturation product.

TABLE 4

Aniline compounds used and corresponding yield of imine

| No. | Additional Reagent | Observations |
|---|---|---|
| 1 | Sulfur (1 wt %) | No reaction |
| 2 | Pyridine (1 to 5 wt %) | Incomplete reaction, trace DMF observed |
| 3 | LiCl (1 to 5 wt %) | Incomplete reaction, ring saturation observed |
| 4 | LiBr (1 wt %) | Incomplete reaction, ring saturation observed |
| 5 | Dimethylamine (0.1 mL) | Ring saturation observed |
| 6 | Triethylamine (0.1 ml) | Ring saturation observed |
| 7 | Diisopropylamine (0.1 mL) | Ring saturation observed |
| 8 | Tertbutylamine (0.1 mL) | Ring saturation observed |
| 9 | 37% aq. HCl (0.1 mL) | Incomplete reaction, ring saturation observed |
| 10 | 98% aq. H$_2$SO$_4$ (0.1 mL) | Ring saturation observed |

Further, the aniline derivatives used for the imine synthesis reaction were also screened for their chemical stability under palladium-catalyzed hydrogenation conditions. Degradation products of certain aniline derivatives were observed by $^1$H NMR to be formed under catalytic hydrogenation conditions. Such degradation products have $^1$H NMR peaks in both aliphatic (1-3 ppm) and aromatic regions (6.5-7.5 ppm). Table 5 summarizes the stability for aniline derivatives.

TABLE 5

Stability of aniline compounds

| No. | Aniline Compounds | Stability under palladium-catalyzed hydrogenation conditions |
|---|---|---|
| 1 | 4-fluoroaniline (F-C6H4-NH2) | Stable |
| 2 | 4-tert-butylaniline (tBu-C6H4-NH2) | Stable |
| 3 | 4-methoxyaniline (MeO-C6H4-NH2) | Unstable |
| 4 | aniline (C6H5-NH2) | Unstable |
| 5 | 2-methylaniline (o-Me-C6H4-NH2) | Unstable |
| 6 | 4-methylaniline (Me-C6H4-NH2) | Unstable |
| 7 | 2-fluoroaniline (o-F-C6H4-NH2) | Unstable |
| 8 | 3-fluoroaniline (m-F-C6H4-NH2) | Unstable |

What is claimed is:

1. A method for preparing an alkylfuran of formula (I):

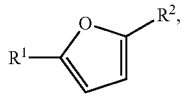

(I)

wherein $R^1$ is H or $C_x$ alkyl, wherein x is an integer equal to or greater than 1;
wherein $R^2$ is $C_y$ alkyl, wherein y is an integer equal to or greater than 1; and
wherein the method comprises:
i) providing an imine of formula (C-1) or (C-2):

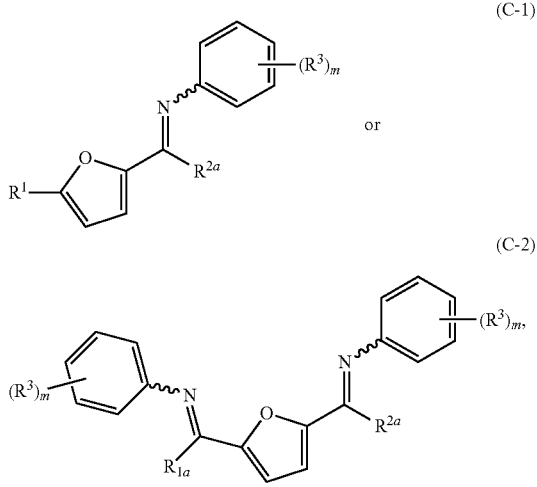

wherein:
$R^1$ is as defined in formula (I);
$R^{1a}$ is H or $C_{x-1}$ alkyl, wherein x is as defined in formula (I), provided that $R^{1a}$ is hydrogen when x is 1;
$R^{2a}$ is H or $C_{y-1}$ alkyl, wherein y is as defined in formula (I), provided that $R^{2a}$ is hydrogen when y is 1;
m is an integer equal to or greater than 0; and
each $R^3$ is independently halo, alkyl, haloalkyl, cycloalkyl, alkoxy, or —C(O)O-alkyl; and
ii) reacting the imine of formula (C-1) or (C-2) with a reducing agent in the presence of a catalyst to produce the alkylfuran of formula (I).

2. The method of claim 1, further comprising reacting a compound of formula (A-1) or (A-2) with an aniline of formula (B) to provide the imine of formula (C-1) or (C-2), wherein:
the compound of formula (A-1) or (A-2) is:

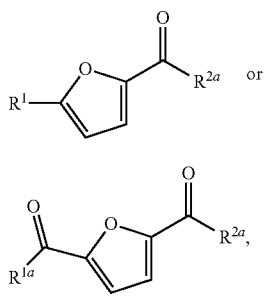

wherein:
$R^1$ is as defined in formula (I);
$R^{1a}$ and $R^{2a}$ are each as defined in formula (C-1) or (C-2); and
the aniline of formula (B) is:

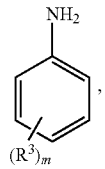

wherein:
m and $R^3$ are as defined in formula (C-1) or (C-2).

3. The method of claim 1, wherein x and y are independently 1 to 10.

4. The method of claim 1, wherein each $R^3$ is independently chloro, fluoro, methyl, ethyl, propyl, butyl, —$CF_3$, —$CHF_2$, —$CH_2F$, methoxy, ethoxy, propoxy, butoxy, —$CO_2$-methyl, —$CO_2$-ethyl, —$CO_2$-propyl, or —$CO_2$-butyl.

5. The method of claim 1, wherein the catalyst is a palladium catalyst.

6. The method of claim 1, wherein the catalyst is palladium on carbon.

7. The method of claim 1, wherein the reducing agent is hydrogen or a hydrogenation donor.

8. The method of claim 1, wherein the reducing agent is hydrogen, and wherein the imine of formula (C-1) or (C-2) is reacted with the hydrogen in the presence of the catalyst and a solvent.

9. The method of claim 8, wherein the solvent has a pKa between 2 and 6.5.

10. The method of claim 1, wherein the compound of formula (A-1) or (A-2) is reacted with the aniline of formula (B) at a temperature of at least 40° C.

11. The method of claim 1, wherein:
the alkylfuran of formula (I) is:

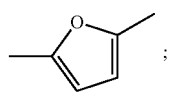

and
the imine of formula (C-1) or (C-2) is:

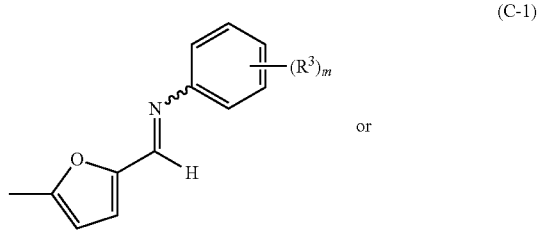

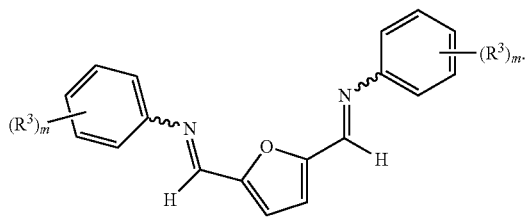
(C-2)

12. A method for preparing 2,5-dimethylfuran, comprising:
reacting an unsubstituted or substituted ((5-methylfuran-2-yl)methylene)aniline with a reducing agent in the presence of a catalyst to produce 2,5-dimethylfuran.

13. The method of claim 12, wherein the ((5-methylfuran-2-yl)methylene)aniline is:
unsubstituted ((5-methylfuran-2-yl)methylene)aniline; or
((5-methylfuran-2-yl)methylene)aniline substituted on the aniline moiety with one to five substituents independently selected from the group consisting of halo, alkyl, haloalkyl, cycloalkyl, alkoxy, and —C(O)O-alkyl.

14. The method of claim 12, wherein the catalyst is a palladium catalyst, a platinum catalyst, a ruthenium catalyst, a copper catalyst or any combination thereof.

15. The method of claim 12, wherein the catalyst is palladium on carbon.

16. The method of claim 12, wherein the unsubstituted or substituted ((5-methylfuran-2-yl)methylene)aniline is reacted with the reducing agent in the presence of the catalyst and a solvent.

17. The method of claim 16, wherein the solvent has a pKa between 2 and 6.5.

18. The method of claim 12, wherein the unsubstituted or substituted ((5-methylfuran-2-yl)methylene)aniline is provided by:
reacting 5-methylfurfural with an unsubstituted or substituted aniline to provide the unsubstituted or substituted ((5-methylfuran-2-yl)methylene)aniline.

19. The method of claim 18, wherein the 5-methylfurfural is reacted with the unsubstituted or substituted aniline at a temperature of at least 40° C.

20. The method of claim 18, wherein the aniline is:
unsubstituted aniline; or
aniline substituted with one to five substituents independently selected from the group consisting of halo, alkyl, haloalkyl, cycloalkyl, alkoxy, and —C(O)O-alkyl.

21. The method of claim 1, wherein $R^1$ is H, and $R^2$ is methyl.

22. The method of claim 1, wherein $R^1$ and $R^2$ are both methyl.

* * * * *